United States Patent
Nakamura et al.

(10) Patent No.: US 9,529,261 B2
(45) Date of Patent: Dec. 27, 2016

(54) COLOR-FORMING COMPOSITION, COLOR-FORMING CURABLE COMPOSITION, LITHOGRAPHIC PRINTING PLATE PRECURSOR AND PLATE MAKING METHOD, AND COLOR-FORMING COMPOUND

(71) Applicant: FUJIFILM Corporation, Tokyo (JP)

(72) Inventors: Koki Nakamura, Shizuoka (JP); Akio Mizuno, Shizuoka (JP); Shota Suzuki, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 14 days.

(21) Appl. No.: 14/466,238

(22) Filed: Aug. 22, 2014

(65) Prior Publication Data

US 2014/0360395 A1    Dec. 11, 2014

Related U.S. Application Data

(63) Continuation of application No. PCT/JP2013/052210, filed on Jan. 31, 2013.

(30) Foreign Application Priority Data

Feb. 23, 2012    (JP) .................................. 2012-037653

(51) Int. Cl.

| | | |
|---|---|---|
| *G03F 7/027* | (2006.01) | |
| *C07D 401/12* | (2006.01) | |
| *C07D 417/12* | (2006.01) | |
| *C07D 277/20* | (2006.01) | |
| *C07D 277/36* | (2006.01) | |
| *C07D 211/94* | (2006.01) | |
| *G03F 7/11* | (2006.01) | |
| *B41C 1/10* | (2006.01) | |
| *G03F 7/038* | (2006.01) | |
| *G03F 7/105* | (2006.01) | |
| *B41N 3/08* | (2006.01) | |
| *C08K 5/38* | (2006.01) | |
| *C08K 5/39* | (2006.01) | |
| *C07F 7/18* | (2006.01) | |

(52) U.S. Cl.
CPC .................. *G03F 7/027* (2013.01); *B41C 1/10* (2013.01); *B41C 1/1016* (2013.01); *B41C 1/1075* (2013.01); *B41N 3/08* (2013.01); *C07D 211/94* (2013.01); *C07D 277/20* (2013.01); *C07D 277/36* (2013.01); *C07D 401/12* (2013.01); *C07D 417/12* (2013.01); *C08K 5/38* (2013.01); *C08K 5/39* (2013.01); *G03F 7/038* (2013.01); *G03F 7/0388* (2013.01); *G03F 7/105* (2013.01); *G03F 7/11* (2013.01); *B41C 2201/02* (2013.01); *B41C 2201/10* (2013.01); *B41C 2210/04* (2013.01); *B41C 2210/08* (2013.01); *B41C 2210/22* (2013.01); *B41C 2210/24* (2013.01); *B41C 2210/26* (2013.01); *C07F 7/1852* (2013.01)

(58) Field of Classification Search
CPC .................................................. B41C 2210/22
See application file for complete search history.

(56) References Cited

U.S. PATENT DOCUMENTS

| | | | |
|---|---|---|---|
| 5,756,356 A | 5/1998 | Yanagi et al. | |
| 7,005,234 B2 | 2/2006 | Hoshi et al. | |
| 7,026,097 B2 | 4/2006 | Hoshi et al. | |
| 8,371,219 B2 | 2/2013 | Suzuki | |
| 2002/0058211 A1* | 5/2002 | Sampei ............. | G03C 1/49845 430/353 |
| 2002/0177074 A1 | 11/2002 | Hoshi et al. | |
| 2003/0054288 A1 | 3/2003 | Shimada et al. | |
| 2003/0064318 A1 | 4/2003 | Huang et al. | |
| 2004/0180289 A1 | 9/2004 | Shimada et al. | |
| 2004/0214105 A1 | 10/2004 | Hoshi et al. | |
| 2007/0056457 A1 | 3/2007 | Iwai et al. | |
| 2010/0212524 A1 | 8/2010 | Suzuki | |

FOREIGN PATENT DOCUMENTS

| | | |
|---|---|---|
| JP | 09-096572 A | 4/1997 |
| JP | 11-277927 A | 10/1999 |

(Continued)

OTHER PUBLICATIONS

Derek H. R. Barton, et al., "A practical decarboxylative hydroxylation of carboxylic acids", Tetrahedron, 1998, vol. 54, No. 24, p. 6751-6756.
Martin Banwell and Jason Smith, "A mild, one-pot method for the conversion of carboxylic acids into the corresponding weinreb amides", Synthetic Communications, 2001, vol. 31. No. 13, p. 2011-2019.

(Continued)

*Primary Examiner* — Matthew G Marini
*Assistant Examiner* — Michael Robinson
(74) *Attorney, Agent, or Firm* — Sughrue Mion, PLLC

(57) ABSTRACT

A color-forming composition contains (A) a radical generator, (B) a compound represented by the following formula (1) and (C) a binder polymer:

(1)

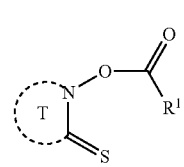

wherein, in the formula (1), $R^1$ represents a group which reacts with a radical generated from the radical generator (A) to be released and forms a dye after the release, and T represents a nitrogen-containing hetero ring.

16 Claims, No Drawings

(56) References Cited

FOREIGN PATENT DOCUMENTS

| | | | |
|---|---|---|---|
| JP | 2000-335129 A | 12/2000 | |
| JP | 2001-277740 A | 10/2001 | |
| JP | 2001-277742 A | 10/2001 | |
| JP | 2002-287334 A | 10/2002 | |
| JP | 2002-341519 A | 11/2002 | |
| JP | 2003-191657 A | 7/2003 | |
| JP | 2006-002107 A | 1/2006 | |
| JP | 2006-030342 A | 2/2006 | |
| JP | 2006-068949 A | 3/2006 | |
| JP | 2007-090850 A | 4/2007 | |
| JP | 2010-221692 A | 10/2010 | |

OTHER PUBLICATIONS

Derek H. R. Barton, Dominique Bridon and Samir Z. Zard, "The invention of radical reactions. Part XVIII. Decarboxylative radical addition to arsenic, antimony, and bismuth phenyl sulphides.—A novel synthesis of nor-alcohols from carboxylic acids", Tetrahedron, 1989, vol. 45, No. 9, p. 2615-2626.

John L. Esker and Martin Newcomb, "N-Acyl-Nalkylcarbamoyloxy radicals: entries to amidyl radicals by decarboxylation and to a-amide radicals by radical translocation", Tetrahedron Letters, 1992, vol. 33, No. 40, p. 5913-5916.

International Search Report for PCT/JP2013/052210 dated May 7, 2013 [PCT/ISA/210].

Written Opinion for PCT/JP2013/052210 dated May 7, 2013 [PCT/ISA/237].

\* cited by examiner

COLOR-FORMING COMPOSITION, COLOR-FORMING CURABLE COMPOSITION, LITHOGRAPHIC PRINTING PLATE PRECURSOR AND PLATE MAKING METHOD, AND COLOR-FORMING COMPOUND

CROSS REFERENCE TO RELATED APPLICATION

This is a continuation of International Application No. PCT/JP2013/052210 filed on Jan. 31, 2013, and claims priority from Japanese Patent Application No. 2012-037653 filed on Feb. 23, 2012, the entire disclosures of which are incorporated herein by reference.

TECHNICAL FIELD

The present invention relates to a color-forming composition capable of providing excellent color formation upon exposure to light, a color-forming curable composition, and a lithographic printing plate precursor in which the color-forming curable composition is applied to an image-recording layer and a plate making method including on-press development using the same, and a novel color-forming compound.

BACKGROUND ART

In general, a lithographic printing plate is composed of an oleophilic image area accepting ink and a hydrophilic non-image area accepting dampening water in the process of printing. Lithographic printing is a printing method utilizing the nature of water and oily ink to repel with each other and comprising rendering the oleophilic image area of the lithographic printing plate to an ink-receptive area and the hydrophilic non-image area thereof to a dampening water-receptive area (ink-unreceptive area), thereby making a difference in adherence of the ink on the surface of the lithographic printing plate, depositing the ink only to the image area, and then transferring the ink to a printing material, for example, paper.

In order to produce the lithographic printing plate, a lithographic printing plate precursor (PS plate) comprising a hydrophilic support having provided thereon an oleophilic photosensitive resin layer (image-recording layer) is heretofore used. Specifically, the PS plate is exposed through a mask, for example, a lith film, and then subjected to development processing, for example, with an alkaline developer to remove the unnecessary image-recording layer corresponding to the non-image area by dissolving while leaving the image-recording layer corresponding to the image area, thereby obtaining the lithographic printing plate.

Due to the recent progress in the technical field, nowadays the lithographic printing plate can be obtained by a CTP (computer-to-plate) technology. Specifically, a lithographic printing plate precursor is directly subjected to scanning exposure using laser or laser diode without using a lith film and developed to obtain a lithographic printing plate.

With the progress described above, the issue on the lithographic printing plate precursor has transferred to improvements, for example, in image-forming property corresponding to the CTP technology, printing property or physical property. Also, with the increasing concern about global environment, as another issue on the lithographic printing plate precursor, an environmental problem on waste liquid discharged accompanying the wet treatment, for example, development processing comes to the front.

In response to the environmental problem, simplification of development or plate making or non-processing has been pursued. As one method of simple plate making, a method referred to as an "on-press development" is practiced. Specifically, according to the method after exposure of a lithographic printing plate precursor, the lithographic printing plate precursor is mounted as it is on a printing machine without conducting conventional development and removal of the unnecessary area of image-recording layer is performed at an early stage of printing process.

In the simplification of plate making operation as described above, a system using a lithographic printing plate precursor capable of being handled in a bright room or under a yellow lamp and a light source is preferred from the standpoint of workability. Thus, as the light source, a semiconductor laser emitting an infrared ray having a wavelength of 760 to 1,200 or a solid laser, for example, YAG laser, is used. An UV laser is also used.

As the lithographic printing plate precursor capable of undergoing on-press development, for instance, a lithographic printing plate precursor having provided on a hydrophilic support, an image-recording layer (heat-sensitive layer) containing microcapsules having a polymerizable compound encapsulated therein is described in Patent Documents 1 and 2. A lithographic printing plate precursor having provided on a support, an image-recording layer (photosensitive layer) containing an infrared absorbing dye, a radical polymerization initiator and a polymerizable compound is described in Patent Document 3. A lithographic printing plate precursor capable of undergoing on-press development having provided on a support, an image-recording layer containing a polymerizable compound and a graft polymer having a polyethylene oxide chain in its side chain or a block polymer having a polyethylene oxide block is described in Patent Document 4.

In general, an operation (plate inspection) for inspection and discrimination of image formed on a printing plate is carried out in order to examine whether the image is recorded on the printing plate as intended, in advance of mounting the printing plate on a printing machine. In a conventional lithographic printing plate precursor subjected to a development processing step, since a color image is ordinarily obtained due to the development processing by means of coloration of the image-recording layer it is easily performed to confirm the image formed before the mounting the printing plate on a printing machine.

With respect to the lithographic printing plate precursor of the on-press development type or non-processing (non-development) type without accompanying the development processing, the image is not recognized on the printing plate in the step of mounting it on a printing machine, and thus the plate inspection cannot be performed. In particular, it is vital in the printing operation to determine whether a registry guide (register mark) which acts as a landmark for the register in multicolor printing is recorded. Therefore, in the lithographic printing plate precursor of the on-press development type or non-processing (non-development) type, a means for confirming the image, that is, color formation or decoloration in the exposed area to form a so-called print-out image is required at the stage of exposure. Further, from the standpoint of improvement in the workability, it is required that the exposed area color-formed or decolored does not change after the lapse of time and the color-formed or decolored state is maintained.

A lithographic printing plate precursor is proposed wherein a compound capable of generating an acid, base or radical by means of light or heat and a compound capable of undergoing color change upon interaction with the acid, base or radical generated are used as a print-out agent (for example, see Patent Document 5). Also, it is proposed to utilize color change of thermally decomposable compound as the print-out agent of a direct-drawing type lithographic printing plate precursor having a heat-sensitive layer (for example, see Patent Document 6). Further, it is proposed to use a thermally decomposable dye having a thermally decomposable temperature of 250° C. or below as the print-out agent (for example, see Patent Document 7).

According to these proposals, although the color formation or decoloration occurs in the exposed area and the plate inspection property increases to some extent, it is still insufficient.

It is described in Patent Document 8 that a print-out image having a good visibility and a level capable of performing plate inspection is obtained by a system containing an infrared absorbing dye of cyanine dye having a 5-membered ring in its methine chain and a radical generator. However, the technique is still insufficient in view of maintaining the good visibility after the lapse of time.

It is described in Patent Document 9 that good visibility is obtained by a compound having a property of decomposing upon heat or light stimulus. It is described that the compound causes change in the π conjugated system at the time of decomposition to form a colored body. However, the visibility according to the technique is still insufficient in comparison with the conventional lithographic printing plate precursor subjected to a development processing step, and a higher color-forming property is required.

PRIOR ART DOCUMENT

Patent Document

Patent Document 1: JP-A-2001-277740
Patent Document 2: JP-A-2001-277742
Patent Document 3: JP-A-2002-287334
Patent Document 4: U.S. Patent Publication No. 2003/0064318
Patent Document 5: JP-A-11-277927
Patent Document 6: JP-A-2000-335129
Patent Document 7: JP-A-2003-191657
Patent Document 8: JP-A-2007-90850
Patent Document 9: JP-A-2010-221692

DISCLOSURE OF THE INVENTION

Problems that the Invention is to Solve

Objects of the invention are as described below.
(1) To provide a color-forming composition and a color-forming curable composition each of which forms high color upon exposure to light and has small fading after the color formation. (2) To provide a lithographic printing plate precursor which forms high color upon exposure to light, which has small fading after the color formation, which has a high plate inspection property, and which provides a lithographic printing plate of high printing durability by plate making. (3) To provide a lithographic printing plate precursor described above which is capable of undergoing on-press development. (4) To provide a plate making method of the lithographic printing plate precursor described above by on-press development. (5) To provide a novel color-forming compound.

Means for Solving the Problems (1) A color-forming composition containing (A) a radical generator, (B) a compound represented by formula (1) shown below and (C) a binder polymer.

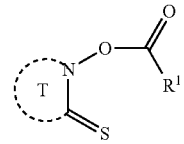

(1)

In formula (1), $R^1$ represents a group which reacts with a radical generated from the radical generator (A) to be released and forms a dye after the release, and T represents a nitrogen-containing hetero ring.

(2) The color-forming composition as described in (1) above, wherein $R^1$ in the compound represented by formula (1) has a structure represented by formula (2) or (3) shown below.

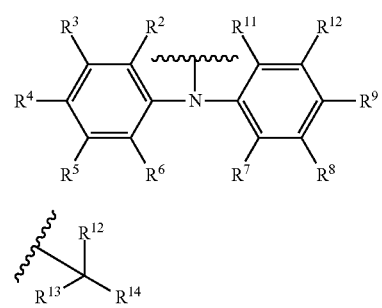

(2)

(3)

In formulae (2) and (3), $R^2$, $R^3$, $R^5$, $R^6$, $R^7$, $R^8$, $R^{10}$ and $R^{11}$ each independently represents a hydrogen atom, an alkyl group, $OR^{15}$, $NR^{16}R^{17}$, $SR^{18}$ or a halogen atom, or $R^5$ and $R^6$, $R^7$ and $R^8$ or $R^6$ and $R^7$ may be connected with each other to form a condensed ring structure, $R^4$ and $R^9$ each independently represents any one of $OR^{15}$, $NR^{19}R^{20}$ and $SR^{18}$, $R^{15}$ and $R^{18}$ each independently represents an alkyl group, $R^{16}$ and $R^{17}$ each independently represents a hydrogen atom or an alkyl group, or $R^{16}$ and $R^{17}$ may from a ring structure, $R^{19}$ and $R^{20}$ each independently represents a hydrogen atom, an alkyl group, an aryl group, an alkylcarbonyl group, an arylcarbonyl group, an aryloxycarbonyl group, an alkoxycarbonyl group, an aminocarbonyl group or an alkylsulfonyl group, or $R^{19}$ and $R^{20}$ may from a ring structure, and $R^{12}$, $R^{13}$ and $R^{14}$ each independently represents an aryl group.

(3) The color-forming composition as described in (1) or (2) above, wherein a maximum absorption wavelength (λmax) of the dye which is formed by releasing from the compound represented by formula (1) is from 500 to 600 nm.

(4) The color-forming composition as described in any one of (1) to (3) above, wherein the compound represented by formula (1) is a compound represented by formula (4) or (5) shown below.

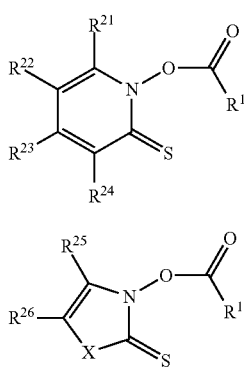

(4)

(5)

In formulae (4) and (5), $R^{21}$, $R^{22}$, $R^{23}$, $R^{24}$, $R^{25}$ and $R^{26}$ each independently represents a hydrogen atom, an alkyl group, an aryl group, $OR^{15}$, $NR^{16}R^{17}$, $SR^{18}$ or a halogen atom, or $R^{21}$ and $R^{22}$, $R^{22}$ and $R^{23}$, $R^{23}$ and $R^{24}$ or $R^{25}$ and $R^{26}$ may be connected with each other to form a condensed ring structure, $R^{15}$ and $R^{18}$ each independently represents an alkyl group, $R^{16}$ and $R^{17}$ each independently represents a hydrogen atom or an alkyl group, or $R^{16}$ and $R^{17}$ may from a ring structure, X represents a dialkylmethylene group, O, $NR^{27}$ or S, $R^{27}$ represents a hydrogen atom, an alkyl group or an aryl group, and $R^1$ has the same meaning as $R^1$ defined in formula (1).

(5) The color-forming composition as described in any one of (1) to (4) above, which further contains (D) a sensitizing dye.
(6) The color-forming composition as described in (5) above, wherein the sensitizing dye (D) is an infrared sensitizing dye.
(7) The color-forming composition as described in any one of (1) to (6) above, wherein the radical generator (A) is an iodonium salt or a sulfonium salt.
(8) A color-forming curable composition, wherein the color-forming composition as described in any one of (1) to (7) above further contains (E) a polymerizable compound.
(9) A lithographic printing plate precursor comprising an image-recording layer containing the color-forming curable composition as described in (8) above on a support.
(10) The lithographic printing plate precursor as described in (9) above, which further comprises a protective layer.
(11) The lithographic printing plate precursor as described in (10) above, wherein the protective layer contains an inorganic stratiform compound.
(12) The lithographic printing plate precursor as described in any one of (9) to (11) above, wherein the image-recording layer contains a hydrophobizing precursor.
(13) A plate making method comprising conducting on-press development processing by any one of a method comprising image-exposing the lithographic printing plate precursor as described in any one of (9) to (12) above to form color in an exposed area, mounting the image-exposed lithographic printing plate precursor on a printing machine and supplying printing ink and dampening water, and a method comprising mounting the lithographic printing plate precursor as described in any one of (9) to (12) above on a printing machine, image-exposing the lithographic printing plate precursor to form color in an exposed area and supplying printing ink and dampening water.
(14) A compound represented by formula (4) or (5) shown below.

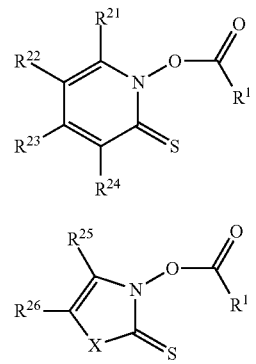

(4)

(5)

In formulae (4) and (5), $R^1$ represents a structure represented by formula (2) or (3) shown below, $R^{21}$, $R^{22}$, $R^{23}$, $R^{24}$, $R^{25}$ and $R^{26}$ each independently represents a hydrogen atom, an alkyl group, an aryl group or a halogen atom, X represents a dialkylmethylene group, O, $NR^{27}$ or S, and $R^{27}$ represents a hydrogen atom, an alkyl group or an aryl group.

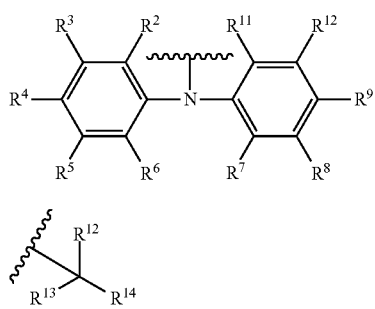

(2)

(3)

In formulae (2) and (3), $R^2$, $R^3$, $R^5$, $R^6$, $R^7$, $R^8$, $R^{10}$ and $R^{11}$ each independently represents a hydrogen atom, an alkyl group or a halogen atom, or $R^5$ and $R^6$, $R^7$ and $R^8$ or $R^6$ and $R^7$ may be connected with each other to form a condensed ring structure, $R^4$ and $R^9$ each independently represents an $NR^{18}R^{19}$ group, $R^{18}$ and $R^{19}$ each independently represents a hydrogen atom, an alkyl group or an alkylsulfonyl group, and $R^{12}$, $R^{13}$ and $R^{14}$ each independently represents a phenyl group having a substituent.

(15) A compound represented by formula (4) or (5) shown below.

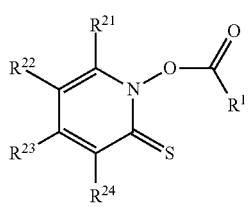

(4)

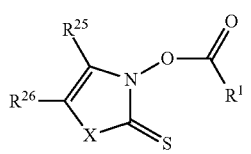

(5)

In formulae (4) and (5), $R^1$ represents a structure represented by formula (2) or (3) shown below, $R^{21}$, $R^{22}$, $R^{23}$ and $R^{26}$ each independently represents a hydrogen atom, $R^{24}$ represents a hydrogen atom or a chlorine atom, $R^{25}$ represents a hydrogen atom or a phenyl group, X represents a dialkylmethylene group, O, $NR^{27}$ or S, and $R^{27}$ represents a hydrogen atom, an alkyl group or an aryl group.

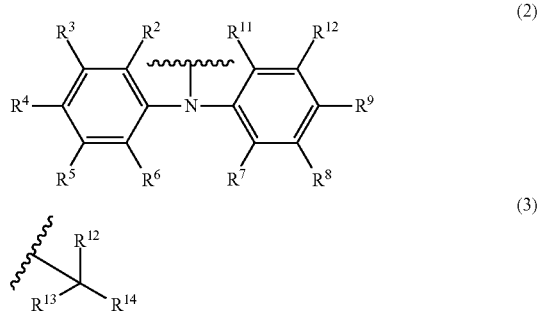

In formulae (2) and (3), $R^2$, $R^3$, $R^5$, $R^6$, $R^7$, $R^8$, $R^{10}$ and $R^{11}$ each independently represents a hydrogen atom or an alkyl group, or $R^5$ and $R^6$, $R^7$ and $R^8$ or $R^6$ and $R^7$ may be connected with each other to form a condensed ring structure, $R^4$ and $R^9$ each independently represents $NR^{18}R^{19}$, $R^{18}$ and $R^{19}$ each independently represents a hydrogen atom, an alkyl group or an alkylsulfonyl group, and $R^{12}$, $R^{13}$ and $R^{14}$ each independently represents a phenyl group having a dialkylamino group in its 4-position.

According to the invention, the solution to the problem of forming high color upon exposure to light can be achieved by using the compound represented by formula (1). The functional mechanism thereof is supposed to be as follows.

A radical generated from the radical generator (A) by function of light, heat or both of them reacts with the compound (B) represented by formula (1) having a specific skeleton to release a leuco dye ($R^1$) from the compound represented by formula (1), and the leuco dye forms color, thereby obtaining a color image. According to the invention, since an optional dye can be incorporated into the compound represented by formula (1) and released therefrom, a sufficient lifetime of the colored body and a high color-forming property can be obtained.

Advantage of the Invention

According to the invention, a color-forming composition and a color-forming curable composition each of which forms high color upon exposure to light and has small fading after the color formation is obtained. Also, a lithographic printing plate precursor, particularly, a lithographic printing plate precursor capable of undergoing on-press development, which forms high color upon exposure to light, which has small fading after the color formation, which has a high plate inspection property, and which provides a lithographic printing plate of high printing durability by plate making, and a plate making method thereof are obtained. Further, a novel color-forming compound is provided.

MODE FOR CARRYING OUT THE INVENTION

[Color-Forming Composition]

The color-forming composition according to the invention is characterized by containing (A) a radical generator, (B) a compound represented by formula (1) shown below and (C) a binder polymer. The color-forming composition according to the invention preferably further contains a sensitizing dye (D), and more preferably further contains a polymerizable compound (E).

(A) Radical Generator

The radical generator (A) which can be used in the invention is a compound which generates a radical by energy of light, heat or both of them and includes, for example, known thermal polymerization initiators, compounds containing a bond having small bond dissociation energy and photopolymerization initiators. As the radical generator according to the invention, known polymerization initiators and compounds containing a bond having small bond dissociation energy can be appropriately selected to use. The compounds which generate a radical may be used individually or in combination of two or more thereof.

The radical generator according to the invention include, for example, (a) an organic halide, (b) a carbonyl compound, (c) an azo compound, (d) an organic peroxide, (e) a metallocene compound, (f) an azide compound, (g) a hexaarylbiimidazole compound, (h) an organic borate compound, (i) a disulfone compound, (j) an oxime ester compound and (k) an onium salt compound.

As the organic halide (a), compounds described in Paragraph Nos. [0022] to [0023] of JP-A-2008-195018 are preferred.

As the carbonyl compound (b), compounds described in Paragraph No. [0024] of JP-A-2008-195018 are preferred.

As the azo compound (c), for example, azo compounds described in JP-A-8-108621 can be used.

As the organic peroxide (d), for example, compounds described in Paragraph No. [0025] of JP-A-2008-195018 are preferred.

As the metallocene compound (e), for example, compounds described in Paragraph No. [0026] of JP-A-2008-195018 are preferred.

As the azide compound (f), a compound, for example, 2,6-bis(4-azidobenzylidene)-4-methylcyclohexanone is exemplified.

As the hexaarylbiimidazole compound (g), for example, compounds described in Paragraph No. [0027] of JP-A-2008-195018 are preferred.

As the organic borate compound (h), for example, compounds described in Paragraph No. [0028] of JP-A-2008-195018 are preferred.

As the disulfone compound (i), for example, compounds described in JP-A-61-166544 and JP-A-2002-328465 are exemplified.

As the oxime ester compound (j), for example, compounds described in Paragraph Nos. to [0030] of JP-A-2008-195018 are preferred.

As the onium salt compound (k), onium salts, for example, diazonium salts described in S. I. Schlesinger, *Photogr. Sci. Eng.*, 18, 387 (1974), T. S. Bal et al., *Polymer*, 21, 423 (1980) and JP-A-5-158230, ammonium salts described in U.S. Pat. No. 4,069,055 and JP-A-4-365049, phosphonium salts described in U.S. Pat. Nos. 4,069,055 and 4,069,056, iodonium salts described in European Patent 104,143, U.S. Patent Publication No. 2008/0311520, JP-A-2-150848, JP-A-2008-195018 and J. V. Crivello et al., *Macromolecules*, 10 (6), 1307 (1977), sulfonium salts described in European Patents 370,693, 233,567, 297,443 and 297,442, U.S. Pat. Nos. 4,933,377, 4,760,013, 4,734, 444 and 2,833,827 and German Patents 2,904,626, 3,604, 580 and 3,604,581, selenonium salts described in J. V. Crivello et al., *J. Polymer Sci., Polymer Chem. Ed.*, 17, 1047

(1979), arsonium salts described in C. S. Wen et al., *Teh, Proc. Conf. Rad. Curing ASIA*, p. 478, Tokyo, October (1988), and azinium salts described in JP-A-2008-195018 are exemplified.

Of the radical generators described above, the oxime ester compound or onium salt, in particular, the iodonium salt, the sulfonium salt or the azinium salt is more preferred from the standpoint of color-forming property. In particular, in the case of utilizing in a lithographic printing plate precursor, the iodonium salt or the sulfonium salt is more preferred. Specific examples of these compounds are set forth below, but the invention should not be construed as being limited thereto.

Examples of the oxime ester compound include 2-acetoxyimino-1-(4-phenylthiophenyl)-1-octanone, 2-benzoyloxyimino-1-(4-phenylthiophenyl)-1-octanone, 2-benzoyloxyimino-1-(4-methylthiophenyl)-1-octanone, 2-phenylozalyloxyimino-1-(4-phenylthiophenyl)-1-octanone, 2-benzoyloxyimino-1-(4-phenylthiophenyl)-1-propanone, 2-benzoyloxyimino-1-(4-phenylthiophenyl)-1,3-butanedione, α-benzoyloxyiminobenzyl 4-morpholinophenyl ketone, α-benzoyloxyiminobenzyl 4-methylthiophenyl ketone, benzyl bis(O-benzoyloxime), acetophenone O-(1-naphthalenesulfinyl)oxime, acetone O-(p-tolyl)sulfonyloxime, acetone O-benzoyloxime, 1-benzoyloxyimino-1-phenylacetonitrile and 1-indanone O-benzoyloxime.

Of the iodonium salts, a diphenyliodonium salt is preferred. In particular, a diphenyliodonium salt substituted with an electron donating group, for example, an alkyl group or an alkoxy group is preferred, and an asymmetric diphenyliodonium salt is more preferred. Specific examples of the iodonium salt include diphenyliodonium hexafluorophosphate, 4-methoxyphenyl-4-(2-methylpropyl)phenyliodonium hexafluorophosphate, 4-(2-methylpropyl)phenyl-p-tolyliodonium hexafluorophosphate, 4-hexyloxyphenyl-2,4,6-trimethoxyphenyliodonium hexafluorophosphate, 4-hexyloxyphenyl-2,4-diethoxyphenyliodonium tetrafluoroborate, 4-octyloxyphenyl-2,4,6-trimethoxyphenyliodonium 1-perfluorobutanesulfonate, 4-octyloxyphenyl-2,4,6-trimethoxyphenyliodonium hexafluorophosphate and bis(4-tert-butylphenyl)iodonium hexafluorophosphate.

Of the sulfonium salts, a triarylsulfonium salt is preferred, particularly, a triarylsulfonium salt substituted with an electron withdrawing group, for example, a halogen atom is preferred, and triarylsulfonium salt substituted with 4 or more halogen atoms is more preferred. Specific examples of the sulfonium salt include triphenylsulfonium hexafluorophosphate, triphenylsulfonium benzoylformate, bis(4-chlorophenyl)phenylsulfonium benzoylformate, bis(4-chlorophenyl)-4-methylphenylsulfonium tetrafluoroborate, tris(4-chlorophenyl)sulfonium 3,5-bis(methoxycarbonyl)benzenesulfonate, tris(4-chlorophenyl)sulfonium hexafluorophosphate and tris(2,4-dichlorophenyl)sulfonium hexafluorophosphate.

Examples of the azinium salt include 1-cyclohexylmethyloxypyridinium hexafluorophosphate, 1-cyclohexyloxy-4-phenylpyridinium hexafluorophosphate, 1-ethoxy-4-phenylpyridinium hexafluorophosphate, 1-(2-ethylhexyloxy)-4-phenylpyridinium hexafluorophosphate, 4-chloro-1-cyclohexylmethyloxypyridinium hexafluorophosphate, 1-ethoxy-4-cyanopyridinium hexafluorophosphate, 3,4-dichloro-1-(2-ethylhexyloxy)pyridinium hexafluorophosphate, 1-benzyloxy-4-phenylpyridinium hexafluorophosphate, 1-phenethyloxy-4-phenylpyridinium hexafluorophosphate, 1-(2-ethylhexyloxy)-4-phenylpyridinium p-toluenesulfonate, 1-(2-ethylhexyloxy)-4-phenylpyridinium perfluorobutanesulfonate, 1-(2-ethylhexyloxy)-4-phenylpyridinium bromide and 1-(2-ethylhexyloxy)-4-phenylpyridinium tetrafluoroborate.

The radical generator according to the invention can be added preferably in an amount from 0.1 to 50% by weight, more preferably from 0.5 to 30% by weight, particularly preferably from 0.8 to 20% by weight, based on the total solid content constituting the color-forming composition, color-forming curable composition or image-recording layer. In the range described above, good color-forming property is obtained and in the case of the lithographic printing plate precursor, good stain resistance in the non-image area at the time of printing is obtained.

(B) Compound Represented by Formula (1)

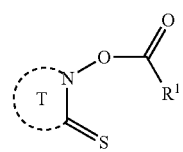

(1)

In formula (1), $R^1$ represents a group which reacts with a radical generated from the radical generator (A) to be released and forms a dye after the release, and T represents a nitrogen-containing hetero ring.

Hereinafter, the compound represented by formula (1) is also referred to as a specific compound.

In the invention, a moiety other than $R^1$ in the specific compound is referred to as a mother nucleus and represented by M. In that case, the specific compound is represented by M-$R^1$. The mother nucleus has a structure wherein —O—CO— is connected to a nitrogen-containing hetero ring represented by T as shown below.

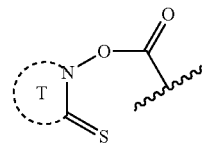

Mother nucleus (M)

$R^1$ in formula (1) represents a group which forms a dye after the release, that is, a group which forms color after the release. The term "forms color" as used herein means that although in a state where the mother nucleus (M) and $R^1$ are connected with a covalent bond there is almost no absorption in a visible light range (>400 nm), after the covalent bond is cleaved upon the reaction with a radical generated from the radical generator to release $R^1$, an intense color is formed or the absorption moves to a longer wavelength. As to a preferred range of absorption after the color formation, a maximum absorption wavelength (λmax) is 450 to 650 nm, more preferably from 500 to 600 nm, from the standpoint of visibility.

Examples of $R^1$ include a group for forming a so-called leuco dye, for example, of an azo dye, an oxonol dye, an arylidene dye, a benzylidene dye, a cinnamylidene dye, a quinone dye, a phenoxyimidazole dye, a pyrimidinetrione dye, a malonanaline dye, an indoaniline dye, a pyrazolinone dye, a triphenylmethane dye or an azine series dye, in which a mother nucleus is connected to a chromophore by a covalent bond (the azine series dye as used herein including a thiazine dye, an oxazine dye and a phenazine dye).

$R^1$ is preferably a group forming any one of an azo dye, a cinnamylidene dye, an indoaniline dye, a triphenylmethane dye and an azine series dye, and more preferably a group forming any one of an indoaniline dye, a triphenylmethane dye and an azine series dye, from the standpoint of color-forming property and production adaptability. Further, a group forming any one of an indoaniline dye, a thiazine dye, an oxazine dye and a phenazine dye, which is represented by formula (2) shown below or a group forming a triphenyl-methane dye, which is represented by formula (3) shown below is most preferred.

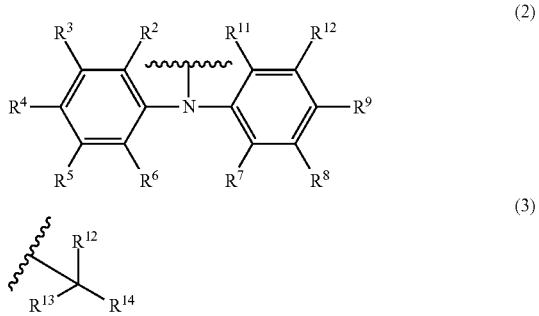

In formulae (2) and (3), $R^2$, $R^3$, $R^5$, $R^6$, $R^7$, $R^8$, $R^{10}$ and $R^{11}$ each independently represents a hydrogen atom, an alkyl group, $OR^{15}$, $NR^{16}R^{17}$, $SR^{18}$ or a halogen atom, or $R^5$ and $R^6$, $R^7$ and $R^8$ or $R^6$ and $R^7$ may be connected with each other to form a condensed ring structure, $R^4$ and $R^9$ each independently represents $OR^{15}$, $NR^{19}R^{20}$ or $SR^{18}$, $R^{15}$ and $R^{18}$ each independently represents an alkyl group, $R^{16}$ and $R^{17}$ each independently represents a hydrogen atom or an alkyl group, or $R^{16}$ and $R^{17}$ may from a ring structure, $R^{19}$ and $R^{20}$ each independently represents a hydrogen atom, an alkyl group, an aryl group, an alkylcarbonyl group, an arylcarbonyl group, an aryloxycarbonyl group, an alkoxycarbonyl group, an aminocarbonyl group or an alkylsulfonyl group, or $R^{19}$ and $R^{20}$ may be connected with each other to from a ring structure, and $R^{12}$, $R^{13}$ and $R^{14}$ each independently represents an aryl group.

The alkyl group represented by any one of $R^2$, $R^3$, $R^5$, $R^6$, $R^7$, $R^8$, $R^{10}$ and $R^{11}$ is preferably an alkyl group having from 1 to 20 carbon atoms, more preferably an alkyl group having from 1 to 10 carbon atoms, and most preferably an alkyl group having from 1 to 4 carbon atoms.

Specific examples of the alkyl group include a methyl group, an ethyl group, a propyl group, a butyl group, a pentyl group, a hexyl group, a heptyl group, an octyl group, a nonyl group, a decyl group, an undecyl group, a dodecyl group, a tridecyl group, a hexadecyl group, an octadecyl group, an eicosyl group, an isopropyl group, an isobutyl group, a sec-butyl group, a tert-butyl group, an isopentyl group, a neopentyl group, a 1-methylbutyl group, an isohexyl group, a 2-ethylhexyl group, 2-methylhexyl group, a cyclohexyl group, a cyclopentyl group and a 2-norbornyl group.

Of the alkyl groups, a methyl group, an ethyl group, a propyl group, a butyl group and a tert-butyl group are particularly preferred.

The aryl group represented by any one of $R^{12}$, $R^{13}$ and $R^{14}$ is preferably an aryl group having from 6 to 30 carbon atoms, more preferably an aryl group having from 6 to 20 carbon atoms, and most preferably an aryl group having from 6 to 12 carbon atoms.

For example, a phenyl group or a naphthyl group is preferred, and the aryl group may have a substituent. Examples of the substituent include an alkyl group, an aryl group, an alkoxy group, an amino group, an alkylthio group, an arylthio group and a halogen atom.

Preferred examples of the substituent are described below.

Specific examples of the alkyl group include a methyl group, an ethyl group, a propyl group, a butyl group, an isopropyl group, an isobutyl group, a sec-butyl group and a tert-butyl group.

Specific examples of the aryl group include a phenyl group, a 1-naphthyl group, a 2-naphthyl group, an o-, m- or p-tolyl group, a p-methoxyphenyl group, a p-dimethylaminophenyl group and a p-methylthiophenyl group.

Specific examples of the alkoxy group include a methoxy group, an ethoxy group, a propoxy group, a butoxy group, an isopropoxy group, an isobutoxy group, a sec-butoxy group and a tert-butoxy group.

The amino group include a dialkylamino group and a monoalkylamino group, and in the case of the dialkylamino group, the alkyl groups may form a ring to be a cyclic amino group. Specific examples of the alkyl group in the amino group include a methyl group, an ethyl group, a propyl group, a butyl group, an isopropyl group, an isobutyl group, a sec-butyl group and a tert-butyl group. Specific examples of the cyclic amino group include a pyrrolidyl group, a piperidyl group and a morpholino group.

Specific examples of the alkylthio group include a methylthio group, an ethylthio group, a propylthio group, a butylthio group, an isopropylthio group, an isobutylthio group, a sec-butylthio group, a tert-butylthio group, a pentylthio group, a hexylthio group, a heptylthio group and an octyl group.

Specific examples of the arylthio group include a phenylthio group, a 1-naphthylthio group, a 2-naphthylthio group, an o-, m- or p-tolylthio group, a p-methoxyphenylthio group and a p-dimethylaminophenylthio group.

Specific examples of the aryl group represented by any one of $R^{12}$, $R^{13}$ and $R^{14}$ include a phenyl group, a biphenyl group, a 1-naphthyl group, a 2-naphthyl group, a 9-fluorenyl group, a terphenyl group, an o-, m- or p-tolyl group, a xylyl group, an o-, m- or p-cumenyl group, a mesityl group, a biphenylenyl group, an indacenyl group, a fluorenyl group, a p-chlorophenyl group, a p-bromophenyl group, a p-fluorophenyl group, an o-chlorophenyl group, an o-bromophenyl group, an o-fluorophenyl group, a p-methoxyphenyl group, a m-methoxyphenyl group, a p-dimethylaminophenyl group, a p-diethylaminophenyl group, a p-morpholinophenyl group, a p-(1-pyrrolidinyl)phenyl group, a p-(1-piperadinyl)phenyl group, a p-methylthiophenyl group, a m-methylthiophenyl group, a p-phenylthiophenyl group, a 2,3-difluorophenyl group, a 2,3-dichlorophenyl group, a 2,4-difluorophenyl group, a 2,4-dichlorophenyl group, a 2,5-difluorophenyl group, a 2,5-dichlorophenyl group, a 2,6-difluorophenyl group, a 2,6-dichlorophenyl group, a 2,4,6-trifluorophenyl group, a 2,4,6-trichlorophenyl group, a 3,4,5-trifluorophenyl group, a 3,4,5-trichlorophenyl group, a 2-methyl-4-dimethylaminophenyl group and a 3-methyl-4-ethylaminophenyl group.

Of the aryl groups, a phenyl group, a p-methoxyphenyl group, a p-dimethylaminophenyl group, a p-morpholinophenyl group and a 2-methyl-4-dimethylaminophenyl group are particularly preferred.

In the case where any one of $R^{15}$, $R^{16}$, $R^{17}$ and $R^{18}$ represents the alkyl group, preferred embodiments thereof are same as the preferred embodiments in the case where any one of $R^2$, $R^3$, $R^5$, $R^6$, $R^7$, $R^8$, $R^{10}$ and $R^{11}$ represents the alkyl group.

In the case where any one of $R^{19}$ and $R^{20}$ represents the alkyl group, preferred embodiments thereof are same as the preferred embodiments in the case where any one of $R^2$, $R^3$, $R^5$, $R^6$, $R^7$, $R^8$, $R^{10}$ and $R^{11}$ represents the alkyl group.

The aryl group represented by any one of $R^{19}$ and $R^{20}$ is preferably an aryl group having from 6 to 30 carbon atoms, more preferably an aryl group having from 6 to 20 carbon atoms, and most preferably an aryl group having from 6 to 12 carbon atoms.

Specific examples of the aryl group include a phenyl group, a biphenyl group, a 1-naphthyl group, a 2-naphthyl group, a 9-fluorenyl group, a terphenyl group, an o-, m- or p-tolyl group, a xylyl group, an o-, m- or p-cumenyl group, a mesityl group, a biphenylenyl group, an indacenyl group, a fluorenyl group, a p-chlorophenyl group, a p-bromophenyl group, a p-fluorophenyl group, an o-chlorophenyl group, an o-bromophenyl group, an o-fluorophenyl group, a p-methoxyphenyl group, a m-methoxyphenyl group, a p-dimethylaminophenyl group, a p-methylthiophenyl group, a m-methylthiophenyl group, a p-phenylthiophenyl group, a 2,3-difluorophenyl group, a 2,3-dichlorophenyl group, a 2,4-difluorophenyl group, a 2,4-dichlorophenyl group, a 2,5-difluorophenyl group, a 2,5-dichlorophenyl group, a 2,6-difluorophenyl group, a 2,6-dichlorophenyl group, a 2,4,6-trifluorophenyl group, a 2,4,6-trichlorophenyl group, a 3,4,5-trifluorophenyl group and a 3,4,5-trichlorophenyl group.

Of the aryl groups, a phenyl group, a p-methoxyphenyl group and a p-dimethylaminophenyl group are particularly preferred.

In the case where any one of $R^{19}$ and $R^{20}$ represents the alkylcarbonyl group, the alkylcarbonyl group is represented by an alkyl group-CO— and preferred embodiments of the alkyl group are same as the preferred embodiments in the case where any one of $R^2$, $R^3$, $R^5$, $R^6$, $R^7$, $R^8$, $R^{10}$ and $R^{11}$ represents the alkyl group.

In the case where any one of $R^{19}$ and $R^{20}$ represents the arylcarbonyl group, the arylcarbonyl group is represented by an aryl group-CO— and preferred embodiments of the aryl group are same as the preferred embodiments in the case where any one of $R^{12}$, $R^{13}$ and $R^{14}$ represents the aryl group.

In the case where any one of $R^{19}$ and $R^{20}$ represents the alkoxycarbonyl group, the alkoxycarbonyl group is represented by an alkyl group-O(CO)— and preferred embodiments of the alkyl group are same as the preferred embodiments in the case where any one of $R^2$, $R^3$, $R^5$, $R^6$, $R^7$, $R^8$, $R^{10}$ and $R^{11}$ represents the alkyl group.

In the case where any one of $R^{19}$ and $R^{20}$ represents the aryloxycarbonyl group, the aryloxycarbonyl group is represented by an aryl group-O(CO)— and preferred embodiments of the aryl group are same as the preferred embodiments in the case where any one of $R^{12}$, $R^{13}$ and $R^{14}$ represents the aryl group.

In the case where any one of $R^{19}$ and $R^{20}$ represents the aminocarbonyl group, the aminocarbonyl group is represented by $R^A R^B N$—(CO)—, wherein $R^A$ and $R^B$ each represents a hydrogen atom, an alkyl group or an aryl group, and preferred embodiments of the alkyl group and aryl group are same as the preferred embodiments in the case where any one of $R^2$, $R^3$, $R^5$, $R^6$, $R^7$, $R^8$, $R^{10}$ and $R^{11}$ represents the alkyl group and in the case where any one of $R^{12}$, $R^{13}$ and $R^{14}$ represents the aryl group, respectively.

In the case where any one of $R^{19}$ and $R^{20}$ represents the alkylsulfonyl group, the alkylsulfonyl group is represented by an alkyl group-$SO_2$— and preferred embodiments of the alkyl group are same as the preferred embodiments in the case where any one of $R^2$, $R^3$, $R^5$, $R^6$, $R^7$, $R^8$, $R^{10}$ and $R^{11}$ represents the alkyl group.

The condensed ring structure formed by connecting $R^5$ and $R^6$ or $R^7$ and $R^8$ is preferably a 5-membered or 6-membered alicyclic ring and a 6-membered aromatic ring, and most preferably a 6-membered aromatic ring.

As to the condensed ring structure formed by connecting $R^6$ and $R^7$, a number of members for forming the condensed ring is preferably 5 or 6, and a 6-membered ring connected with an oxygen atom, —$NR^C$— or a sulfur atom is most preferred. $R^C$ is preferably a hydrogen atom, an alkyl group or an aryl group.

The alkyl group represented by $R^C$ is preferably an alkyl group having from 1 to 20 carbon atoms, more preferably an alkyl group having from 1 to 10 carbon atoms, and most preferably an alkyl group having from 1 to 4 carbon atoms. Specific examples of the alkyl group include a methyl group, an ethyl group, a propyl group, a butyl group, a pentyl group, a hexyl group, a heptyl group, an octyl group, a nonyl group, a decyl group, an undecyl group, a dodecyl group, a tridecyl group, a hexadecyl group, an octadecyl group, an eicosyl group, an isopropyl group, an isobutyl group, a sec-butyl group, a tert-butyl group, an isopentyl group, a neopentyl group, a 1-methylbutyl group, an isohexyl group, a 2-ethylhexyl group, 2-methylhexyl group, a cyclohexyl group, a cyclopentyl group and a 2-norbornyl group. Of the alkyl groups, a methyl group, an ethyl group, a propyl group, a butyl group and a tert-butyl group are particularly preferred.

The aryl group represented by $R^C$ is preferably an aryl group having from 6 to 30 carbon atoms, more preferably an aryl group having from 6 to 20 carbon atoms, and most preferably an aryl group having from 6 to 12 carbon atoms. Specific examples of the aryl group include a phenyl group, a biphenyl group, a 1-naphthyl group, a 2-naphthyl group, an o-, m- or p-tolyl group, a xylyl group, a mesityl group, a p-chlorophenyl group, a p-bromophenyl group, a p-fluorophenyl group, an o-chlorophenyl group, an o-bromophenyl group, an o-fluorophenyl group, a p-methoxyphenyl group, a m-methoxyphenyl group, a p-dimethylaminophenyl group, a p-diethylaminophenyl group, a p-methylthiophenyl group, a m-methylthiophenyl group, a p-phenylthiophenyl group, a 2,3-difluorophenyl group, a 2,3-dichlorophenyl group, a 2,4-difluorophenyl group, a 2,4-dichlorophenyl group, a 2,5-difluorophenyl group, a 2,5-dichlorophenyl group, a 2,6-difluorophenyl group, a 2,6-dichlorophenyl group, a 2,4,6-trifluorophenyl group, a 2,4,6-trichlorophenyl group, a 3,4,5-trifluorophenyl group and a 3,4,5-trichlorophenyl group. Of the aryl groups, a phenyl group, a p-methoxyphenyl group and a p-dimethylaminophenyl group are particularly preferred.

The condensed ring structure by connecting $R^{16}$ and $R^{17}$ or $R^{19}$ and $R^{20}$ is preferably a 5-membered or 6-membered ring.

Preferred specific examples of $R^1$ are set forth below, but the invention should not be construed as being limited thereto. Although when a covalent bond is formed between $R^1$ and the mother nucleus, the covalent bond may be formed at any position in $R^1$ as long as the position is in the dye chromophore, it is preferred to from a covalent bond between the atom indicated by arrow in $R^1$ and the mother nucleus.

TABLE 1

| R¹ | No | λ max |
|---|---|---|
| (2,6-dichloro-4-((4-nitrophenyl)diazenyl)phenoxy, arrow on O) | Z-1 | 482 |
| (3-chloro-4-((2-(methylsulfonyl)-4-nitrophenyl)diazenyl)naphthalen-1-ol, arrow on O) | Z-2 | 489 |
| (naphthalenol with SO₂NHC₁₂H₂₅, MeO₂SHN, azo to phenyl with Cl, SO₂NH₂, arrow on O) | Z-3 | 485 |
| NC–C(CN)=CH–CH=CH–(3,5-dichloro-4-oxyphenyl), arrow on O | Z-4 | 492 |
| EtO₂C–C(CN)=CH–CH=CH–(3,5-dichloro-4-oxyphenyl), arrow on O | Z-5 | 481 |

TABLE 1-continued

| R¹ | No | λ max |
|---|---|---|
| (4-(dimethylamino)naphthalen-1-yl)-N-(4-(dimethylamino)phenyl)amine, arrow on N | Z-6 | 612 |
| (naphthalene with NMe₂ and N-(2-chloro-4-(dimethylamino)phenyl), arrow on N | Z-7 | 580 |
| (naphthalene with NMe₂ and N-phenyl-N'-ethyl-N'-(methylsulfonyl), arrow on N | Z-8 | 589 |
| (1-methoxy-4-(N-(3-methoxy-4-(dimethylamino)phenyl)amino)naphthalene, arrow on N | Z-9 | 620 |

TABLE 2
| R¹ | No | λ max |
|---|---|---|
| 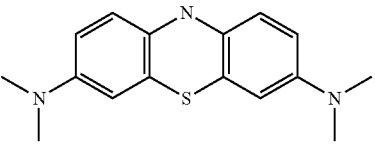 | Z-10 | 640 |
| 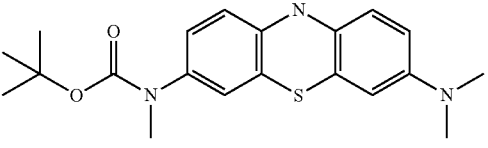 | Z-11 | 582 |
| 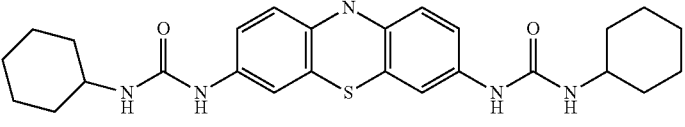 | Z-12 | 485 |
| 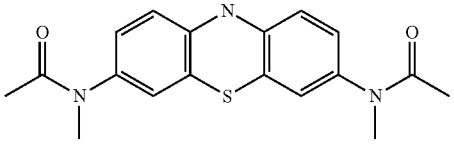 | Z-13 | 487 |
| 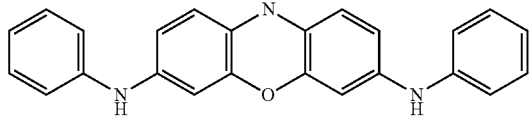 | Z-14 | 620 |
| 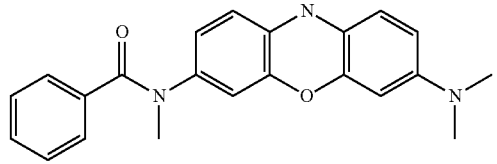 | Z-15 | 587 |
| 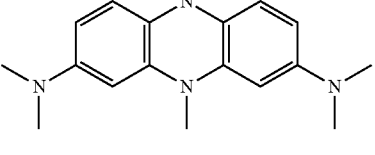 | Z-16 | 565 |

TABLE 2-continued

| R¹ | No | λ max |
|---|---|---|
| (structure) | Z-17 | 578 |
| (structure) | Z-18 | 540 |
| (structure) | Z-19 | 588 |
| (structure) | Z-20 | 620 |
| (structure) | Z-21 | 592 |

TABLE 2-continued

| R¹ | No | λ max |
|---|---|---|
| | Z-22 | 588 |
| | Z-23 | 612 |

The mother nucleus (M) is represented by T-OCO—, and a nitrogen-containing hetero ring represented by T may be any nitrogen-containing hetero ring and is preferably a 4-membered to 8-membered nitrogen-containing heterocyclic group, and more preferably a 5-membered or 6-membered nitrogen-containing heterocyclic group. Preferred 5-membered nitrogen-containing heterocyclic group includes structures represented by formulae (A-1) and (A-2) shown below and preferred 6-membered nitrogen-containing heterocyclic group includes structures represented by formulae (A-3), (A-4) and (A-5) shown below.

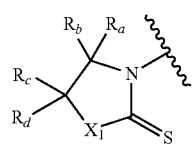
(A-1)

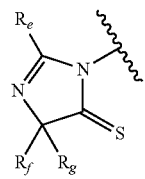
(A-2)

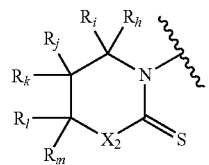
(A-3)

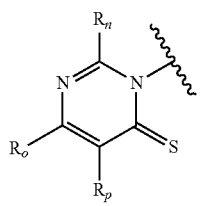
(A-4)

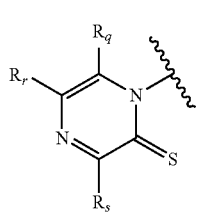
(A-5)

In formulae (A-1) and (A-2), $R_a$, $R_b$, $R_c$, $R_d$, $R_e$, $R_f$ and $R_g$ each independently represents a hydrogen atom, an alkyl group, an aryl group, $OR_t$, $NR_uR_v$, $SR_w$ or a halogen atom, or $R_a$ and $R_c$ may be directly connected to form a carbon-carbon double bond in the ring or may be connected with each other to form a condensed ring structure. $X_1$ represents a connecting group represented by —$CR_xR_y$—, —O—, —$NR_z$— or —S—. $R_t$, $R_w$, $R_x$ and $R_y$ each independently represents a hydrogen atom, an alkyl group or an aryl group, $R_u$, $R_v$ and $R_z$ each independently represents a hydrogen atom, an alkyl group, an aryl group, an alkylcarbonyl group, an arylcarbonyl group, an alkoxycarbonyl group or an alkylsulfonyl group, or $R_u$ and $R_v$ may be connected with each other to form a condensed ring structure.

In formulae (A-3), (A-4) and (A-5), $R_h$, $R_i$, $R_j$, $R_k$, $R_l$, $R_m$, $R_n$, $R_o$, $R_p$, $R_q$, $R_r$ and $R_s$ each independently represents a hydrogen atom, an alkyl group, an aryl group, $OR_t$, $NR_uR_v$, $SR_w$ or a halogen atom, or the substituents on the same carbon atom ($R_h$ and $R_i$, $R_j$ and $R_k$ or $R_l$ and $R_m$) are combined with each other to form a carbonyl group or a thiocarbonyl group in the ring. $X_2$ represents a connecting group represented by —$CR_xR_y$—, >C=O, >C=S, —O—, —$NR_z$— or —S—. $R_h$ and $R_j$, $R_j$ and $R_l$ or $R_l$ and the substituent $R_x$, $R_y$ or $R_z$ of $X_2$ may be directly connected to form a carbon-carbon double bond in the ring or may be connected with each other to form a condensed ring structure.

Of the nitrogen-containing heterocyclic groups, heterocyclic groups represented by formulae (a) and (b) shown below are most preferred.

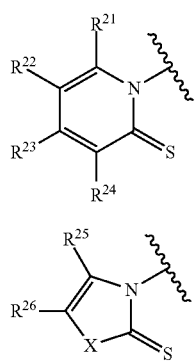

In formulae (a) and (b), $R^{21}$, $R^{22}$, $R^{23}$, $R^{24}$, $R^{25}$ and $R^{26}$ each independently represents a hydrogen atom, an alkyl group, $OR^{15}$, $NR^{16}R^{17}$, $SR^{18}$ or a halogen atom, or $R^{21}$ and $R^{22}$, $R^{22}$ and $R^{23}$, $R^{23}$ and $R^{24}$ or $R^{25}$ and $R^{26}$ may be connected with each other to form a condensed ring structure. $R^{15}$ and $R^{18}$ each independently represents an alkyl group, $R^{16}$ and $R^{17}$ each independently represents a hydrogen atom or an alkyl group, or $R^{16}$ and $R^{17}$ may from a ring structure. X represents a dialkylmethylene group, O, $NR^{27}$ or S, and $R^{27}$ represents a hydrogen atom, an alkyl group or an aryl group.

In the case where any one of $R^{21}$, $R^{22}$, $R^{23}$, $R^{24}$, $R^{25}$, $R^{26}$ and $R^{27}$ represents the alkyl group, preferred embodiments thereof are same as the preferred embodiments in the case where any one of $R^2$, $R^3$, $R^5$, $R^6$, $R^7$, $R^8$, $R^{10}$ and $R^{11}$ in formula (2) represents the alkyl group.

The aryl group represented by any one of $R^{21}$, $R^{22}$, $R^{23}$, $R^{24}$, $R^{25}$, $R^{26}$ and $R^{27}$ is preferably an aryl group having from 6 to 30 carbon atoms, more preferably an aryl group having from 6 to 20 carbon atoms, and most preferably an aryl group having from 6 to 12 carbon atoms.

Specific examples of the aryl group include a phenyl group, a biphenyl group, a 1-naphthyl group, a 2-naphthyl group, a 9-fluorenyl group, a terphenyl group, an o-, m- or p-tolyl group, a xylyl group, an o-, m- or p-cumenyl group, a mesityl group, a biphenylenyl group, an indacenyl group, a fluorenyl group, a p-chlorophenyl group, a p-bromophenyl group, a p-fluorophenyl group, an o-chlorophenyl group, an o-bromophenyl group, an o-fluorophenyl group, a p-methoxyphenyl group, a m-methoxyphenyl group, a p-dimethylaminophenyl group, a p-methylthiophenyl group, a m-methylthiophenyl group, a p-phenylthiophenyl group, a 2,3-difluorophenyl group, a 2,3-dichlorophenyl group, a 2,4-difluorophenyl group, a 2,4-dichlorophenyl group, a 2,5-difluorophenyl group, a 2,5-dichlorophenyl group, a 2,6-difluorophenyl group, a 2,6-dichlorophenyl group, a 2,4,6-trifluorophenyl group, a 2,4,6-trichlorophenyl group, a 3,4,5-trifluorophenyl group and a 3,4,5-trichlorophenyl group.

Of the aryl groups, a phenyl group, a p-fluorophenyl group and a p-chlorophenyl group are particularly preferred.

X is preferably a dialkylmethylene group, O, $NR^{27}$ or S, and particularly preferably O or S. The condensed ring structure formed by connecting $R^{21}$ and $R^{22}$, $R^{22}$ and $R^{23}$, $R^{23}$ and $R^{24}$ or $R^{25}$ and $R^{26}$ is preferably a 5-membered or 6-membered alicyclic ring and a 6-membered aromatic ring, and most preferably a 6-membered aromatic ring. The condensed ring structure formed by connecting $R^{16}$ and $R^{17}$ is preferably a 5-membered or 6-membered ring.

In the case where any one of $R^{15}$, $R^{16}$, $R^{17}$ and $R^{18}$ represents the alkyl group, preferred embodiments thereof are same as the preferred embodiments in the case where any one of $R^2$, $R^3$, $R^5$, $R^6$, $R^7$, $R^8$, $R^{10}$ and $R^{11}$ represents the alkyl group.

Preferred specific examples of the mother nucleus (M) are set forth below, but the invention should not be construed as being limited thereto.

TABLE 3

| M(Mother Nucleus) | No |
|---|---|
|  | M-1 |
|  | M-2 |
|  | M-3 |
|  | M-4 |
|  | M-5 |

TABLE 3-continued
| M(Mother Nucleus) | No |
|---|---|
| 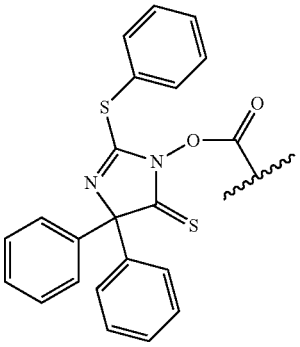 [SMILES: *C(=O)ON1C(=S)C(c2ccccc2)(c2ccccc2)N=C1Sc1ccccc1] | M-6 |
| 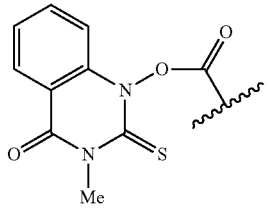 [SMILES: *C(=O)On1c(=S)n(C)c(=O)c2ccccc21] | M-7 |
| 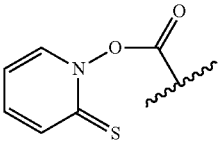 [SMILES: *C(=O)On1ccccc1=S] | M-8 |
| 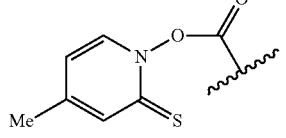 | M-9 |
| 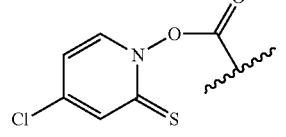 | M-10 |
| 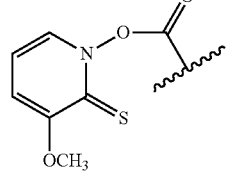 | M-11 |
| 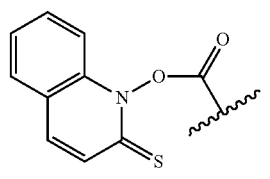 [SMILES: *C(=O)On1c(=S)ccc2ccccc21] | M-12 |
TABLE 3-continued
| M(Mother Nucleus) | No |
|---|---|
| 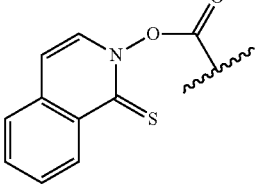 | M-13 |
| 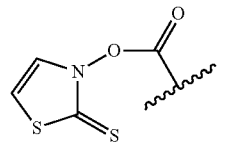 [SMILES: *C(=O)On1ccsc1=S] | M-14 |
| 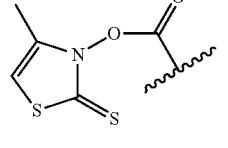 | M-15 |
| 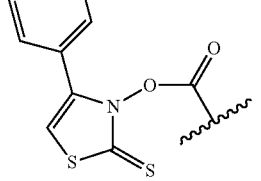 | M-16 |
| 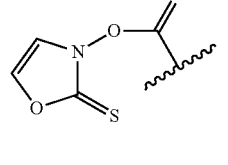 | M-17 |
| 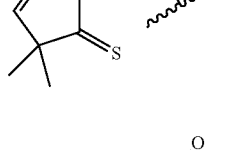 | M-18 |
| 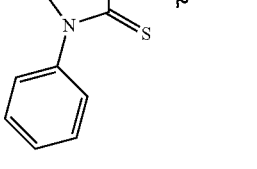 | M-19 |

TABLE 3-continued

| M(Mother Nucleus) | No |
|---|---|
| 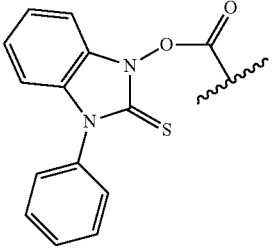 [SMILES: *C(=O)On1c(=S)n(-c2ccccc2)c2ccccc21] | M-20 |

The specific compound according to the invention is preferably a compound represented by formula (4) or (5) shown below.

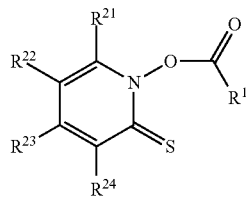

(4)

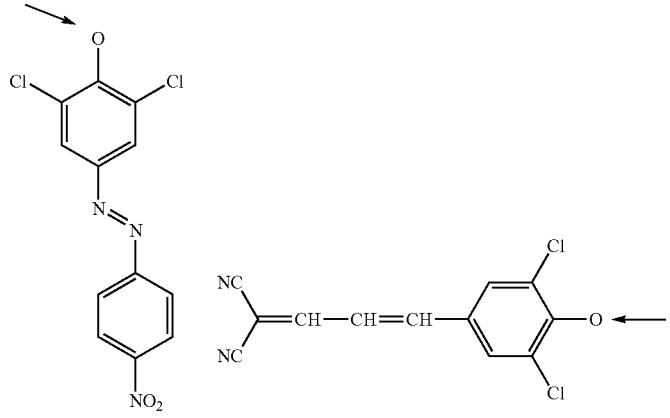

(5)

In formulae (4) and (5), $R^1$, $R^{21}$, $R^{22}$, $R^{23}$, $R^{24}$, $R^{25}$, $R^{26}$ and X have the same meanings as $R^1$ described above and $R^1$, $R^{21}$, $R^{22}$, $R^{23}$, $R^{24}$, $R^{25}$, $R^{26}$ and X in formulae (a) and (b) respectively, and the preferred embodiments are also same as in $R^1$ and formulae (a) and (b). $R^{21}$ and $R^{22}$, $R^{22}$ and $R^{23}$, $R^{23}$ and $R^{24}$ or $R^{25}$ and $R^{26}$ may be connected with each other to form a condensed ring structure.

As the specific compound, compounds in which the respective preferred embodiments of the mother nucleus structure M and $R^1$ are combined are most preferred.

Specific examples of the specific compound are set forth as the combinations of mother nuclei (M-1 to M-19) and $R^1$ (Z-1 to Z-21) in the tables below. A numeral in the tables indicates a number of the specific compound. The invention should not be construed as being limited thereto.

TABLE 4

|  | Z-1 | Z-4 |
|---|---|---|
| M-1 | 1 | 2 |
| M-4 | 5 | 6 |
| M-6 | 9 | 10 |
| M-8 | 13 | 14 |
| M-10 | 17 | 18 |
| M-11 | 21 | 22 |
| M-14 | 25 | 26 |
| M-15 | 29 | 30 |
| M-16 | 33 | 34 |
| M-17 | 37 | 38 |
| M-19 | 41 | 42 |

TABLE 4-continued
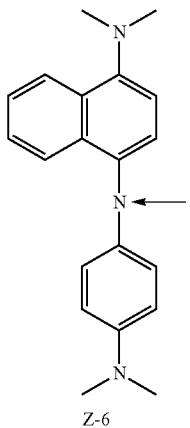 [SMILES: CN(C)c1ccc(Nc2ccc(N(C)C)c3ccccc23)cc1]
| | Z-6 | Z-10 |
|---|---|---|
| M-1 | 3 | 4 |
| M-4 | 7 | 8 |
| M-6 | 11 | 12 |
| M-8 | 15 | 16 |
| M-10 | 19 | 20 |
| M-11 | 23 | 24 |
| M-14 | 27 | 28 |
| M-15 | 31 | 32 |
| M-16 | 35 | 36 |
| M-17 | 39 | 40 |
| M-19 | 43 | 44 |
TABLE 5
| | Z-13 | Z-15 |
|---|---|---|
| M-1 | 45 | 46 |
| M-4 | 49 | 50 |
| M-6 | 53 | 54 |
| M-8 | 57 | 58 |
| M-10 | 61 | 62 |
| M-11 | 65 | 66 |
| M-14 | 69 | 70 |
| M-15 | 73 | 74 |
| M-16 | 77 | 78 |
| M-17 | 81 | 82 |
| M-19 | 85 | 86 |

TABLE 5-continued
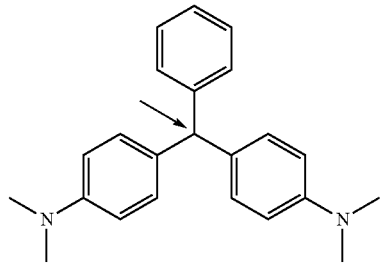
| | Z-20 | Z-8 |
|---|---|---|
| M-1 | 47 | 48 |
| M-4 | 51 | 52 |
| M-6 | 55 | 56 |
| M-8 | 59 | 60 |
| M-10 | 63 | 64 |
| M-11 | 67 | 68 |
| M-14 | 71 | 72 |
| M-15 | 75 | 76 |
| M-16 | 79 | 80 |
| M-17 | 83 | 84 |
| M-19 | 87 | 88 |
TABLE 6
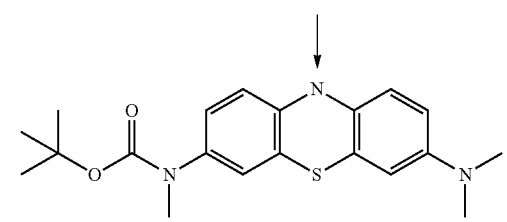
| | Z-11 | Z-16 |
|---|---|---|
| M-1 | 89 | 90 |
| M-4 | 93 | 94 |
| M-6 | 97 | 98 |
| M-8 | 101 | 102 |
| M-10 | 105 | 106 |
| M-11 | 109 | 110 |
| M-14 | 113 | 114 |
| M-15 | 117 | 118 |
| M-16 | 121 | 122 |
| M-17 | 125 | 126 |
| M-19 | 129 | 130 |

TABLE 6-continued

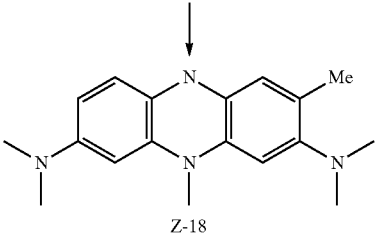

| | Z-18 | Z-21 |
|---|---|---|
| M-1 | 91 | 92 |
| M-4 | 95 | 96 |
| M-6 | 99 | 100 |
| M-8 | 103 | 104 |
| M-10 | 107 | 108 |
| M-11 | 111 | 112 |
| M-14 | 115 | 116 |
| M-15 | 119 | 120 |
| M-16 | 123 | 124 |
| M-17 | 127 | 128 |
| M-19 | 131 | 132 |

Although the specific compound described above can be contained in an optional amount in the color-forming composition, the content thereof is preferably from 0.1 to 50% by weight, more preferably from 0.5 to 30% by weight, still more preferably from 1 to 20% by weight, based on the total solid content of the color-forming composition.

The specific compound according to the invention can be obtained by an ordinary synthesis method according to a synthesis scheme shown below.

The synthesis method is a method in which intermediate (1) having the mother nucleus and a compound corresponding to $HR^1$ are subjected to a reaction in tetrahydrofuran (THF) or toluene at room temperature in the presence of a base.

(Synthesis scheme)

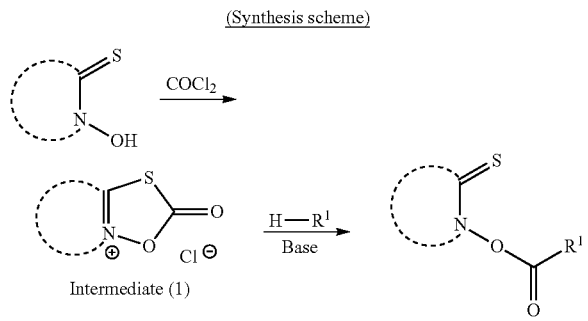

Intermediate (1)

(C) Binder Polymer

The binder polymer which can be used in the invention can be employed those heretofore known without limitation, and polymers having a film-forming property are preferred. Among them, an acrylic resin, a polyvinyl acetal resin and a polyurethane resin are preferred.

In particular, in the case of applying the color-forming composition according to the invention to a lithographic printing plate precursor, as a preferred binder polymer, a polymer having a crosslinkable functional group for improving film strength of the image area in its main chain or side chain, preferably in its side chain, as described in JP-A-2008-195018 is exemplified. Due to the crosslinkable functional group, crosslinkage is formed between the polymer molecules to facilitate curing.

As the crosslinkable functional group, an ethylenically unsaturated group, for example, a (meth)acryl group, a vinyl group or an allyl group, or an epoxy group is preferred. The crosslinkable functional group can be introduced into the polymer by a polymer reaction or copolymerization. For instance, a reaction between an acrylic polymer or polyurethane having a carboxyl group in its side chain and glycidyl methacrylate or a reaction between a polymer having an epoxy group and a carboxylic acid containing an ethylenically unsaturated group, for example, methacrylic acid can be utilized.

The content of the crosslinkable group in the binder polymer is preferably from 0.1 to 10.0 mmol, more preferably from 1.0 to 7.0 mmol, most preferably from 2.0 to 5.5 mmol, based on 1 g of the binder polymer.

In the case of using the color-forming composition in the lithographic printing plate precursor, it is preferred to use the binder polymer according to a development method.

<Binder Polymer for Alkali Development>

Although the chemical structure of the binder polymer is not particularly limited, from the standpoint of solubility in an alkaline processing solution, that is, development property, an organic polymer having an acid group is preferred and particularly, an organic polymer having a carboxylic acid or salt thereof is more preferred.

As the binder polymer which can be used in a color-forming composition for lithographic printing plate precursor of alkali development type, an aqueous alkali-soluble or swellable organic polymer having a carboxylic acid is exemplified. Useful examples of such an organic polymer include addition polymers having a carboxylic acid group in their side chains, for example, polymers described in JP-B-59-44615, JP-B-54-34327, JP-B-58-12577, JP-B-54-25957, JP-A-54-92723, JP-A-59-53836 and JP-A-59-71048, specifically, methacrylic acid copolymers, acrylic acid copolymers, itaconic acid copolymers, crotonic acid copolymers, maleic acid copolymers and partially esterified maleic acid copolymers. As the binder polymer, a copolymer containing a monomer unit derived from a (meth)acrylate and having a carboxylic acid (salt) group is preferred.

Also, an acidic cellulose derivative having a carboxylic acid group in its side chain and a product obtained by adding a cyclic acid anhydride to an addition polymer having a hydroxy group are useful. Further, polyurethane resins described in JP-B-7-120040, JP-B-7-120041, JP-B-7-120042, JP-B-8-12424, JP-A-63-287944, JP-A-63-287947, JP-A-1-271741 and JP-A-11-352691 are also useful as the aqueous alkali-soluble or swellable binder. As the binder polymer for use in the invention, an acrylic resin, a methacrylic resin or a urethane resin is preferably employed.

One preferred example of material for the binder polymer for alkali development is a copolymer having (a) a monomer unit having a carboxylic acid group (including its salt) and (b) a monomer unit for imparting a radical crosslinking property.

The monomer unit (a) having a carboxylic acid group is not particularly limited and structures described in JP-A-2002-40652 and Paragraph Nos. [0059] to [0075] of JP-A-2005-300650 are preferably used.

The monomer unit (b) for imparting a radical crosslinking property is not particularly limited and structures described in Paragraph Nos. [0041] to [0053] of JP-A-2007-248863 are preferably used.

The binder polymer for alkali development may contain a monomer unit derived from an ethylenically unsaturated compound which contains neither the monomer unit (a) having a carboxylic acid group nor the monomer unit (b) for imparting a radical crosslinking property as a copolymerization component.

As such a monomer unit, a monomer unit derived from a (meth)acrylate or (meth)acrylamide is preferred. Particularly, a monomer unit derived from amide group (meth)acrylamide described in Paragraph Nos. [0061] to [0084] of JP-A-2007-272134 is preferably used. The content of such a monomer unit is preferably from 5 to 50 units, more preferably from 5 to 35 units, still more preferably from 5 to 25 units, when the total number of monomer units is taken as 100.

In the color-forming composition according to the invention, in addition to the addition polymer containing a combination of the monomer units described above, a urethane resin having a crosslinkable group in its side chain can also be used as the binder polymer. The term "crosslinkable group" as used herein means a group capable of crosslinking the binder polymer upon a chemical reaction which is caused in the image-recording layer, when the lithographic printing plate precursor is exposed to light. A chemical structure of the crosslinkable group is not particularly limited as long as the crosslinkable group has such a function and, for example, an ethylenically unsaturated group is preferred as a functional group capable of undergoing an addition polymerization reaction. Also, functional groups described in Paragraph Nos. [0130] to of JP-A-2007-17948 are exemplified.

The polyurethane resin having a crosslinkable group in its side chain particularly preferably used in the invention can be obtained by a polyaddition reaction of (i) a diisocyanate compound, (ii) a diol compound having a carboxyl group, (iii) a diisocyanate compound having a crosslinkable group and, if desired, (iv) a diol compound containing no carboxyl group and (v) a compound having an amino group.

The compounds of (i), (ii) and (iii) above include compounds represented by formulae (4) to (10) and specific examples described in Paragraph Nos. [0142] to [0167] of JP-A-2007-17948. The compound of (iv) above include compounds represented by formula (A'), formulae (a) to (e), formulae (11) to (22) and specific compounds described in Paragraph Nos. [0180] to [0225] of JP-A-2007-17948. The compound of (v) above include compounds represented by formulae (31) and (32) and specific compounds described in Paragraph Nos. [0227] to [0230] of JP-A-2007-17948. In addition to the polyurethane resin described above, a polyurethane resin obtained by introducing a crosslinkable group into polyurethane having a carboxyl group by a polymer reaction as described in JP-A-2003-270775 may also be exemplified.

The binder polymer for use in the invention preferably has an appropriate molecular weight in order to maintain the development property of the image-recording layer of lithographic printing plate precursor. The weight average molecular weight (Mw) thereof is preferably from 5,000 to 300,000, and more preferably from 20,000 to 150,000.

Although the binder polymer can be incorporated into the color-forming composition in an optional amount, the content of the binder polymer in the color-forming composition is preferably from 10 to 90% by weight, and more preferably from 30 to 80% by weight.

<Binder Polymer for On-Press Development>

As the binder polymer for on-press development, a binder polymer having an alkylene oxide group is preferred. The binder polymer having an alkylene oxide group for use in the color-forming composition according to the invention may have a poly(alkylene oxide) moiety in the main chain thereof or in the side chain thereof, or may be a graft polymer having a poly(alkylene oxide) in its side chain or a block copolymer composed of a block constituted by a repeating unit containing a poly(alkylene oxide) and a block constituted by a repeating unit not containing an (alkylene oxide).

In the case where the alkylene oxide group is present in the main chain, a polyurethane resin is preferred. In the case where the alkylene oxide group is present in the side chain, a polymer constituting its main chain includes an acrylic resin, a polyvinyl acetal resin, a polyurethane resin, a polyurea resin, a polyimide resin, a polyamide resin, an epoxy resin, a methacrylic resin, a polystyrene resin, a novolac type phenolic resin, a polyester resin, a synthesis rubber and a natural rubber. In particular, an acrylic resin is preferred.

The alkylene oxide is preferably an alkylene oxide having from 2 to 6 carbon atoms, and particularly preferably an ethylene oxide or a propylene oxide.

A repeating number of alkylene oxide in the poly(alkylene oxide) moiety is from 2 to 120, preferably in a range from 2 to 70, and more preferably in a range from 2 to 50.

It is preferred that the repeating number of alkylene oxide is 120 or less because both the printing durability as to abrasion and the printing durability as to ink receptivity are not decreased.

The poly(alkylene oxide) moiety is preferably introduced into an side chain of the binder as a structure represented by formula (5) shown below. More preferably, it is introduced into a side chain of an acrylic resin as a structure represented by formula (5) shown below.

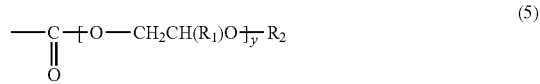

(5)

In formula (5), y represents a number from 2 to 120, preferably in a range from 2 to 70, and more preferably in a range from 2 to 50. $R_1$ represents a hydrogen atom or an alkyl group. $R_2$ represents a hydrogen atom or an organic group. The organic group is preferably an alkyl group having from 1 to 6 carbon atoms and includes a methyl group, an ethyl group, an n-propyl group, an isopropyl group, an n-butyl group, a sec-butyl group, an isobutyl group, a tert-butyl group, an n-pentyl group, an isopentyl group, a neopentyl group, an n-hexyl group, an isohexyl group, a 1,1-dimethylbutyl group, a 2,2-dimethylbutyl group, a cyclopentyl group and a cyclohexyl group.

In formula (5), $R_1$ is preferably a hydrogen atom or a methyl group and most preferably a hydrogen atom. $R_2$ is most preferably a hydrogen atom or a methyl group.

The binder polymer may have a crosslinking property in order to improve the film strength of the image area. In order to impart the crosslinking property to the binder polymer, a crosslinkable functional group, for example, an ethylenically unsaturated bond is introduced into a main chain or side chain of the polymer. The crosslinkable functional group may be introduced by copolymerization.

Examples of the polymer having an ethylenically unsaturated bond in the main chain thereof include poly-1,4-butadiene and poly-1,4-isoprene.

Examples of the polymer having an ethylenically unsaturated bond in the side chain thereof include a polymer of an ester or amide of acrylic acid or methacrylic acid, which is a polymer wherein the ester or amido residue (R in —COOR or —CONHR) has an ethylenically unsaturated bond.

Examples of the residue (R described above) having an ethylenically unsaturated bond include —$(CH_2)_n$CR$^1$=CR$^2$R$^3$, —$(CH_2O)_n$CH$_2$CR$^1$=CR$^2$R$^3$, —$(CH_2CH_2O)_n$CH$_2$CR$^1$=CR$^2$R$^3$, —$(CH_2)_n$NH—CO—O—CH$_2$CR$^1$=CR$^2$R$^3$, —$(CH_2)_n$—O—CO—CR$^1$=CR$^2$R$^3$ and —$(CH_2CH_2O)_2$—X (wherein $R^1$ to $R^3$ each represents a hydrogen atom, a halogen atom or an alkyl group having from 1 to 20 carbon atoms, an aryl group, an alkoxy group or an aryloxy group, or $R^1$ and $R^2$ or $R^1$ and $R^3$ may be combined with each other to form a ring. n represents an integer from 1 to 10. X represents a dicyclopentadienyl residue).

Specific examples of the ester residue include —CH$_2$CH=CH$_2$ (described in JP-B-7-21633), —CH$_2$CH$_2$O—CH$_2$CH=CH$_2$, —CH$_2$C(CH$_3$)=CH$_2$, —CH$_2$CH=CH—C$_6$H$_5$, —CH$_2$CH$_2$OCOCH=CH—C$_6$H$_5$, —CH$_2$CH$_2$—NHCOO—CH$_2$CH=CH$_2$ and —CH$_2$CH$_2$O—X (wherein X represents a dicyclopentadienyl residue).

Specific examples of the amido residue include —CH$_2$CH=CH$_2$, —CH$_2$CH$_2$—Y (wherein Y represents a cyclohexene residue) and —CH$_2$CH$_2$—OCO—CH=CH$_2$.

The binder polymer having a crosslinking property is cured, for example, by addition of a free radical (a polymerization initiating radical or a growing radical of a polymerizable compound in the process of polymerization) to the crosslinkable functional group of the polymer and undergoing addition polymerization between the polymers directly or through a polymerization chain of the polymerizable compound to form crosslinkage between the polymer molecules. Alternately, it is cured by generation of a polymer radical upon extraction of an atom (for example, a hydrogen atom on a carbon atom adjacent to the functional crosslinkable group) in the polymer by a free radial and connecting the polymer radicals with each other to form cross-linkage between the polymer molecules.

The content of the crosslinkable group (content of the radical polymerizable unsaturated double bond determined by iodine titration) in the binder polymer is preferably from 0.1 to 10.0 mmol, more preferably from 1.0 to 7.0 mmol, most preferably from 2.0 to 5.5 mmol, based on 1 g of the polymer compound. In the range described above, good sensitivity and good preservation stability are obtained.

Specific examples (1) to (11) of the binder polymer for on-press development used in the invention are set forth below, but the invention should not be construed as being limited thereto. In the exemplified compounds described below, a numerical value appended to each repeating unit (numerical value appended to a repeating unit of a main chain) indicates a mole percent of the repeating unit. A numerical value appended to a repeating unit of a side chain indicates a repeating number of the repeating unit.

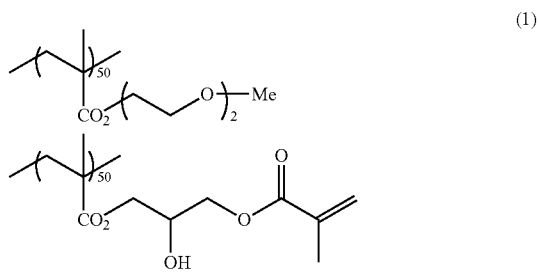

(1)

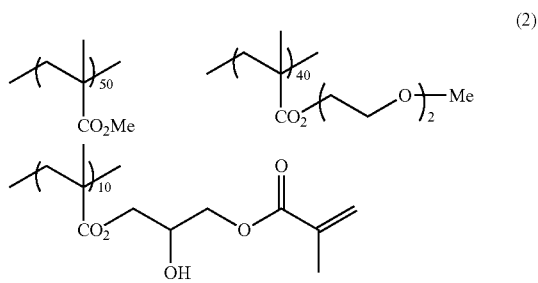

(2)

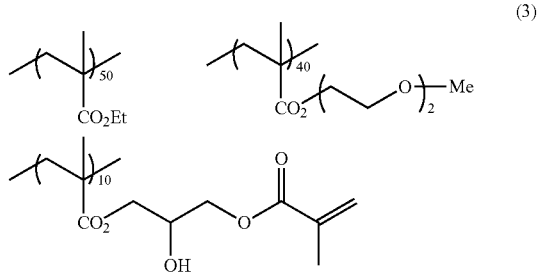

(3)

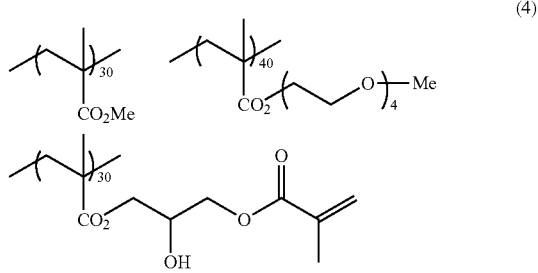

(4)

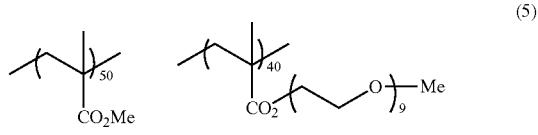

(5)

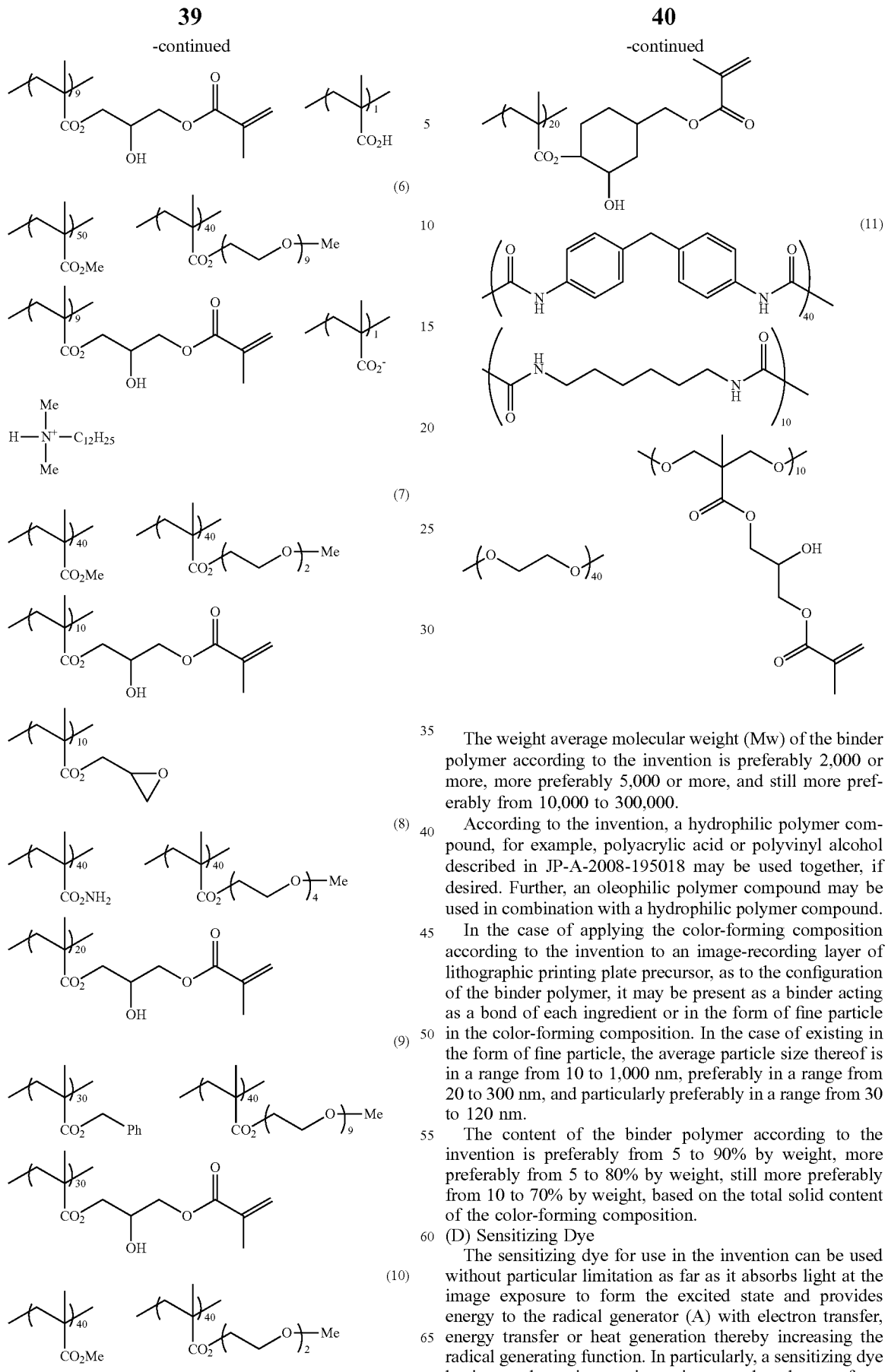

The weight average molecular weight (Mw) of the binder polymer according to the invention is preferably 2,000 or more, more preferably 5,000 or more, and still more preferably from 10,000 to 300,000.

According to the invention, a hydrophilic polymer compound, for example, polyacrylic acid or polyvinyl alcohol described in JP-A-2008-195018 may be used together, if desired. Further, an oleophilic polymer compound may be used in combination with a hydrophilic polymer compound.

In the case of applying the color-forming composition according to the invention to an image-recording layer of lithographic printing plate precursor, as to the configuration of the binder polymer, it may be present as a binder acting as a bond of each ingredient or in the form of fine particle in the color-forming composition. In the case of existing in the form of fine particle, the average particle size thereof is in a range from 10 to 1,000 nm, preferably in a range from 20 to 300 nm, and particularly preferably in a range from 30 to 120 nm.

The content of the binder polymer according to the invention is preferably from 5 to 90% by weight, more preferably from 5 to 80% by weight, still more preferably from 10 to 70% by weight, based on the total solid content of the color-forming composition.

(D) Sensitizing Dye

The sensitizing dye for use in the invention can be used without particular limitation as far as it absorbs light at the image exposure to form the excited state and provides energy to the radical generator (A) with electron transfer, energy transfer or heat generation thereby increasing the radical generating function. In particularly, a sensitizing dye having an absorption maximum in a wavelength range from 300 to 450 nm or an infrared sensitizing dye having an absorption maximum in a wavelength range from 750 to 1,400 nm is preferably used.

Examples of the sensitizing dye having an absorption maximum in a wavelength range from 350 to 450 nm include dyes, for example, merocyanines, benzopyranes, coumarins, aromatic ketones, anthracenes, styryls and oxazoles.

Of the sensitizing dyes having an absorption maximum in a wavelength range from 350 to 450 nm, a more preferred dye is a dye represented by formula (I) shown below from the standpoint of high sensitivity.

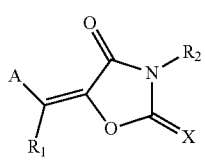
(I)

In formula (I), A represents an aryl group which may have a substituent or a heteroaryl group which may have a substituent, X represents an oxygen atom, a sulfur atom or $N(R_3)$, and $R_1$, $R_2$ and $R_3$ each independently represents a monovalent non-metallic atomic group, or A and $R_1$ or $R_2$ and $R_3$ may be combined with each other to form an aliphatic or aromatic ring.

The formula (I) will be described in more detail below. The monovalent non-metallic atomic group represented by any one of $R_1$, $R_2$ and $R_3$ preferably represents a hydrogen atom, a substituted or unsubstituted alkyl group, a substituted or unsubstituted alkenyl group, a substituted or unsubstituted aryl group, a substituted or unsubstituted heteroaryl group, a substituted or unsubstituted alkoxy group, a substituted or unsubstituted alkylthio group, a hydroxy group or a halogen atom.

As specific examples of the sensitizing dye, compounds described in Paragraph Nos. [0047] to [0053] of JP-A-2007-58170 are preferably used.

Further, sensitizing dyes represented by formulae (II) and (III) shown below can also be used.

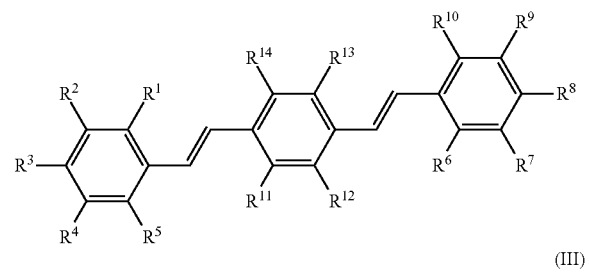
(II)

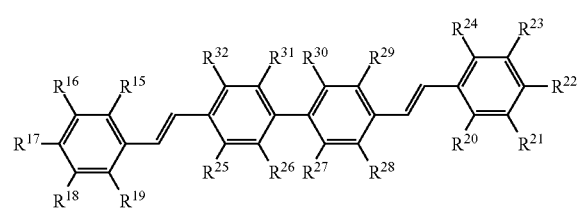
(III)

In formula (II), $R^1$ to $R^{14}$ each independently represents a hydrogen atom, an alkyl group, an alkoxy group, a cyano group or a halogen atom, provided that at least one of $R^1$ to $R^{10}$ represents an alkoxy group having 2 or more carbon atoms.

In formula (III), $R^{15}$ to $R^{32}$ each independently represents a hydrogen atom, an alkyl group, an alkoxy group, a cyano group or a halogen atom, provided that at least one of $R^{15}$ to $R^{24}$ represents an alkoxy group having 2 or more carbon atoms.

As specific examples of the sensitizing dyes, compounds described in EP-A-1,349,006 and WO 2005/029187 are preferably used.

Further, sensitizing dyes described in JP-A-2006-189604, JP-A-2007-171406, JP-A-2007-206216, JP-A-2007-206217, JP-A-2007-225701, JP-A-2007-225702, JP-A-2007-316582 and JP-A-2007-328243 can also be preferably used.

Next, the infrared sensitizing dye having an absorption maximum in a wavelength range from 750 to 1,400 (hereinafter, also referred to as an "infrared absorbing agent") is described below. The infrared absorbing agent used is preferably a dye or pigment.

As the dye, commercially available dyes and known dyes described in literatures, for example, *Senryo Binran*, compiled by The Society of Synthetic Organic Chemistry, Japan (1970) can be utilized. Specifically, dyes, for example, azo dyes, metal complex azo dyes, pyrazolone azo dyes, naphthoquinone dyes, anthraquinone dyes, phthalocyanine dyes, carbonium dyes, quinoneimine dyes, methine dyes, cyanine dyes, squarylium dyes, pyrylium salts or metal thiolate complexes are exemplified.

Of the dyes, cyanine dyes, squarylium dyes, pyrylium dyes, nickel thiolate complexes and indolenine cyanine dyes are particularly preferred. The cyanine dyes and indolenine cyanine dyes are more preferred. As a particularly preferred example of the dye, a cyanine dye represented by formula (IV) shown below is exemplified.

Formula (IV)

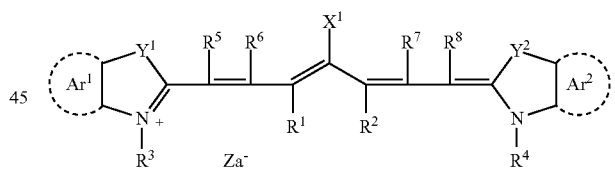

In formula (IV), $X^1$ represents a hydrogen atom, a halogen atom, $-N(R^9)(R^{10})$, $-X^2-L^1$ or a group shown below. $R^9$ and $R^{10}$, which may be the same or different, each represents an aromatic hydrocarbon group having from 6 to 10 carbon atoms, which may have a substituent, an alkyl group having from 1 to 8 carbon atoms or a hydrogen atom, or $R^9$ and $R^{10}$ may be combined with each other to from a ring, and preferably represents a phenyl group. $X^2$ represents an oxygen atom or a sulfur atom, $L^1$ represents a hydrocarbon group having from 1 to 12 carbon atoms, an aromatic cyclic group containing a hetero atom (a nitrogen atom, a sulfur atom, an oxygen atom, a halogen atom or a selenium atom) or a hydrocarbon group having from 1 to 12 carbon atoms and containing a hetero atom. Xa$^-$ in the formula below has the same meaning as Za$^-$ defined hereinafter. $R^a$ represents a hydrogen atom or a substituent selected from an alkyl group, an aryl group, a substituted or unsubstituted amino group and a halogen atom.

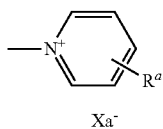

$R^1$ and $R^2$ in formula (IV) each independently represents a hydrocarbon group having from 1 to 12 carbon atoms. In view of the preservation stability of a solution of polymerizable composition, it is preferred that $R^1$ and $R^2$ each represents a hydrocarbon group having two or more carbon atoms. Also, $R^1$ and $R^2$ may be combined with each other to form a ring, and in the case of forming the ring, to form a 5-membered ring or 6-membered ring is particularly preferred.

$Ar^1$ and $Ar^2$, which may be the same or different, each represents an aryl group which may have a substituent. Preferred examples of the aryl group include a benzene ring group and a naphthalene ring group. Preferred examples of the substituent include a hydrocarbon group having 12 or less carbon atoms, a halogen atom and an alkoxy group having 12 or less carbon atoms. $Y^1$ and $Y^2$, which may be the same or different, each represents a sulfur atom or a dialkylmethylene group having 12 or less carbon atoms. $R^3$ and $R^4$, which may be the same or different, each represents a hydrocarbon group having 20 or less carbon atoms, which may have a substituent. Preferred examples of the substituent include an alkoxy group having 12 or less carbon atoms, a carboxyl group and a sulfo group. $R^5$, $R^6$, $R^7$ and $R^8$, which may be the same or different, each represents a hydrogen atom or a hydrocarbon group having 12 or less carbon atoms. In view of ease in availability of raw materials, a hydrogen atom is preferred. $Za^-$ represents a counter anion. However, $Za^-$ is not necessary when the cyanine dye represented by formula (IV) has an anionic substituent in the structure thereof and neutralization of charge is not needed. $Za^-$ is preferably a halide ion, a perchlorate ion, a tetrafluoroborate ion, a hexafluorophosphate ion or a sulfonate ion, and particularly preferably a perchlorate ion, a hexafluorophosphate ion or an arylsulfonate ion in view of the preservation stability of a solution of the polymerizable composition.

Specific examples of the cyanine dye represented by formula (IV) include compounds described in Paragraph Nos. [0017] to [0019] of JP-A-2001-133969 and compounds described in Paragraph Nos. [0016] to [0021] of JP-A-2002-23360 and Paragraph Nos. [0012] to [0037] of JP-A-2002-40638, preferably compounds described in Paragraph Nos. [0034] to [0041] of JP-A-2002-278057 and Paragraph Nos. [0080] to [0086] of JP-A-2008-195018, and particularly preferably compounds described in Paragraph Nos. [0035] to [0043] of JP-A-2007-90850.

Also, compounds described in Paragraph Nos. [0008] to [0009] of JP-A-5-5005 and Paragraph Nos. [0022] to [0025] of JP-A-2001-222101 can be preferably used.

The infrared absorbing dye may be used only one kind or in combination of two or more kinds thereof, and it may also be used together with an infrared absorbing agent other than the infrared absorbing dye, for example, a pigment. As the pigment, compounds described in Paragraph Nos. [0072] to [0076] of JP-A-2008-195018 are preferred.

The content of the sensitizing dye is preferably from 0.05 to 30 parts by weight, more preferably from 0.1 to 20 parts by weight, particularly preferably from 0.2 to 10 parts by weight, per 100 parts by weight of the total solid content of the color-forming composition.

(E) Polymerizable Compound

The polymerizable compound (E) for use in the composition according to the invention is an addition-polymerizable compound having at least one ethylenically unsaturated double bond and it is selected from compounds having at least one, preferably two or more, terminal ethylenically unsaturated double bonds. The polymerizable compound has a chemical form, for example, a monomer, a prepolymer, specifically, a dimer, a trimer or an oligomer, or a mixture thereof. The composition containing the polymerizable compound (E) according to the invention is a color-forming curable composition having a function of polymerization curing in addition to the color-forming property.

Examples of the monomer include unsaturated carboxylic acids (for example, acrylic acid, methacrylic acid, itaconic acid, crotonic acid, isocrotonic acid or maleic acid) and esters or amides thereof. Preferably, esters of an unsaturated carboxylic acid with a polyhydric alcohol compound and amides of an unsaturated carboxylic acid with a polyvalent amine compound are used. An addition reaction product of an unsaturated carboxylic acid ester or amide having a nucleophilic substituent, for example, a hydroxy group, an amino group or a mercapto group, with a monofunctional or polyfunctional isocyanate or an epoxy compound, or a dehydration condensation reaction product of the unsaturated carboxylic acid ester or amide with a monofunctional or polyfunctional carboxylic acid is also preferably used. Moreover, an addition reaction product of an unsaturated carboxylic acid ester or amide having an electrophilic substituent, for example, an isocyanate group or an epoxy group with a monofunctional or polyfunctional alcohol, amine or thiol, or a substitution reaction product of an unsaturated carboxylic acid ester or amide having a releasable substituent, for example, a halogeno group or a tosyloxy group with a monofunctional or polyfunctional alcohol, amine or thiol is also preferably used. In addition, compounds in which the unsaturated carboxylic acid described above is replaced by an unsaturated phosphonic acid, styrene, vinyl ether or the like can also be used. These compounds are described in references including JP-T-2006-508380, JP-A-2002-287344, JP-A-2008-256850, JP-A-2001-342222, JP-A-9-179296, JP-A-9-179297, JP-A-9-179298, JP-A-2004-294935, JP-A-2006-243493, JP-A-2002-275129, JP-A-2003-64130, JP-A-2003-280187 and JP-A-10-333321.

Specific examples of the monomer, which is an ester of a polyhydric alcohol compound with an unsaturated carboxylic acid, include, as an acrylic acid ester, for example, ethylene glycol diacrylate, 1,3-butanediol diacrylate, tetramethylene glycol diacrylate, propylene glycol diacrylate, trimethylolpropane triacrylate, hexanediol diacrylate, tetraethylene glycol diacrylate, pentaerythritol tetraacrylate, sorbitol triacrylate, isocyanuric acid ethylene oxide (EO) modified triacrylate and polyester acrylate oligomer. As a methacrylic acid ester, for example, tetramethylene glycol dimethacrylate, neopentyl glycol dimethacrylate, trimethylolpropane trimethacrylate, ethylene glycol dimethacrylate, pentaerythritol trimethacrylate, bis[p-(3-methacryloxy-2-hydroxypropoxy)phenyl]dimethylmethane and bis[p-(methacryloxyethoxy)phenyl]dimethylmethane are exemplified. Specific examples of the monomer, which is an amide of a polyvalent amine compound with an unsaturated carboxylic acid, include methylene bisacrylamide, methylene bismethacrylamide, 1,6-hexamethylene bisacrylamide, 1,6-hexamethylene bismethacrylamide, diethylenetriamine trisacrylamide, xylylene bisacrylamide and xylylene bismethacrylamide.

Urethane type addition-polymerizable compounds produced using an addition reaction between an isocyanate and a hydroxy group are also preferably used and specific examples thereof include vinylurethane compounds having two or more polymerizable vinyl groups per molecule obtained by adding a vinyl monomer containing a hydroxy group represented by formula (6) shown below to a polyisocyanate compound having two or more isocyanate groups per molecule, described in JP-B-48-41708.

$$CH_2=C(R^4)COOCH_2CH(R^5)OH \qquad (6)$$

wherein $R^4$ and $R^5$ each independently represents H or $CH_3$.

Also, urethane acrylates as described in JP-A-51-37193, JP-B-2-32293, JP-B-2-16765, JP-A-2003-344997 and JP-A-2006-65210, urethane compounds having an ethylene oxide skeleton described in JP-B-58-49860, JP-B-56-17654, JP-B-62-39417, JP-B-62-39418, JP-A-2000-250211 and JP-A-2007-94138, and urethane compounds having a hydrophilic group described in U.S. Pat. No. 7,153,632, JP-T-8-505958, JP-A-2007-293221 and JP-A-2007-293223 are preferably used.

Details of the method of using the polymerizable compound, for example, selection of the structure, individual or combination use or addition amount, can be optionally determined in accordance with the use of the final color-forming composition. The polymerizable compound is used preferably in a range from 5 to 75% by weight, more preferably in a range from 10 to 70% by weight, particularly preferably in a range from 15 to 60% by weight, based on the total solid content of the color-forming curable composition.

(F) Organic Base

The color-forming composition according to the invention preferably contains an organic base in order to increase the color-forming property of dye released in the case where the specific compound in which $R^1$ is an azo dye or a cinnamylidene dye (for example, Z-1 to Z-5) is used. The organic base which can be used in the invention is preferably an amine compound, and an N-arylalkylamine compound which is an electron-donating compound may also be used. As the amine compound, a trialkylamine is preferred from the standpoint of basicity.

Specifically, triethylamine, tripropylamine, tributylamine, trihexylamine, trioctylamine, tridecylamine and tridodecylamine are exemplified.

The content of the organic base is preferably from 0.05 to 50% by weight, more preferably from 0.1 to 30% by weight, still more preferably from 0.5 to 20% by weight, based on the total solid content of the color-forming composition.

[Application of Color-Forming Composition and Color-Forming Curable Composition]

The color-forming composition and color-forming curable composition may contain additives other than those described above in accordance with the intended use. The composition is dissolved or dispersed in an appropriate solvent and the resulting solution is coated, for example, on a support and dried to form a layer of the color-forming composition, thereby preparing an image-forming material. The image-forming material includes an image-forming material which utilizes color formation upon image exposure, for example, a lithographic printing plate precursor, a printed circuit board, a color filter or a photomask, and an image-forming material which utilizes color formation and polymerization curing. In particular, the color-forming composition is preferably used in the production of lithographic printing plate precursor.

The image-forming material is exposed by a light source matching the photosensitive wavelength range of the composition used. As the light source, for example, a super high-pressure mercury lamp, an InGaN semiconductor laser or a solid laser or semiconductor laser emitting an infrared ray is exemplified.

[Lithographic Printing Plate Precursor]

The lithographic printing plate precursor according to the invention comprises on a support, an image-recording layer containing the color-forming curable composition described above. The lithographic printing plate precursor according to the invention may have, if desired, an undercoat layer between the support and the image-recording layer, or a protective layer on the image-recording layer.

Hereinafter, the constituting elements of the lithographic printing plate precursor are described.

[Image-Recording Layer]

The image-recording layer of lithographic printing plate precursor is required to have development aptitude and printing aptitude. Therefore, the color-forming curable composition for the image-recording layer may contain a hydrophobizing precursor and other components described below, in addition to the constituting component described above.

(G) Hydrophobizing Precursor

In the invention, a hydrophobizing precursor can be used in order to improve the on-press development property. The hydrophobizing precursor according to the invention means a fine particle capable of converting the image-recording layer to be hydrophobic when heat is applied. The fine particle is preferably at least one fine particle selected from hydrophobic thermoplastic polymer fine particle, thermoreactive polymer fine particle, polymer fine particle having a polymerizable group, microcapsule having a hydrophobic compound encapsulated and microgel (crosslinked polymer fine particle). Among them, polymer fine particle having a polymerizable group and microgel are preferred.

As the hydrophobic thermoplastic polymer fine particle, hydrophobic thermoplastic polymer fine particles described, for example, in Research Disclosure, No. 333003, January (1992), JP-A-9-123387, JP-A-9-131850, JP-A-9-171249, JP-A-9-171250 and European Patent 931,647 are preferably exemplified.

Specific examples of the polymer constituting the polymer fine particle include a homopolymer or copolymer of a monomer, for example, ethylene, styrene, vinyl chloride, methyl acrylate, ethyl acrylate, methyl methacrylate, ethyl methacrylate, vinylidene chloride, acrylonitrile, vinyl carbazole or an acrylate or methacrylate having a polyalkylene structure and a mixture thereof. Among them, polystyrene, a copolymer containing styrene and acrylonitrile and polymethyl methacrylate are more preferred.

The average particle size of the hydrophobic thermoplastic polymer fine particle for use in the invention is preferably from 0.01 to 2.0 μm.

The thermo-reactive polymer fine particle for use in the invention includes polymer fine particle having a thermo-reactive group and forms a hydrophobized region by cross-linkage due to thermal reaction and change in the functional group involved therein.

As the thermo-reactive group of the polymer fine particle having a thermo-reactive group for use in the invention, although a functional group performing any reaction can be used as long as a chemical bond is formed, a polymerizable group is preferred. For instance, an ethylenically unsaturated group (for example, an acryloyl group, a methacryloyl group, a vinyl group or an allyl group) performing a radical polymerization reaction, a cationic polymerizable group (for example, a vinyl group, a vinyloxy group, an epoxy group or an oxetanyl group), an isocyanate group performing an addition reaction or a blocked form thereof, an epoxy group, a vinyloxy group and a functional group having an active hydrogen atom (for example, an amino group, a hydroxy group or a carboxyl group) as the reaction partner thereof, a carboxyl group performing a condensation reaction and a hydroxyl group or an amino group as the reaction partner thereof, and an acid anhydride performing a ring opening addition reaction and an amino group or a hydroxyl group as the reaction partner thereof are preferably exemplified.

As the microcapsule for use in the invention, microcapsule having all or part of the constituting components of the image-recording layer encapsulated as described, for example, in JP-A-2001-277740 and JP-A-2001-277742 is exemplified. The constituting components of the image-recording layer may be present outside the microcapsules. It is a more preferred embodiment of the image-recording layer containing microcapsules that the hydrophobic constituting components are encapsulated in microcapsules and the hydrophilic components are present outside the microcapsules.

According to the invention, an embodiment containing a crosslinked resin particle, that is, a microgel may be used. The microgel can contain a part of the constituting components of the image-recording layer at least one of in the inside and on the surface thereof. In particular, an embodiment of a reactive microgel containing a radical polymerizable group on the surface thereof is preferred in view of the image-forming sensitivity and printing durability.

In order to conduct microencapsulation or microgelation of the constituting component of the image-recording layer, known methods can be used.

The average particle size of the microcapsule or microgel is preferably from 0.01 to 3.0 μm, more preferably from 0.05 to 2.0 μm, particularly preferably from 0.10 to 1.0 μm. In the range described above, good resolution and good time lapse stability can be achieved.

The content of the hydrophobizing precursor is preferably in a range from 5 to 90% by weight based on the total solid content of the image-recording layer.

(H) Other Components

The image-recording layer according to the invention may further contain other components, if desired.

(1) Hydrophilic Low Molecular Weight Compound

The image-recording layer according to the invention may contain a hydrophilic low molecular weight compound in order to improve the on-press development property without accompanying the decrease in the printing durability.

The hydrophilic low molecular weight compound includes a water-soluble organic compound, for example, a glycol, e.g., ethylene glycol, diethylene glycol, triethylene glycol, propylene glycol, dipropylene glycol or tripropylene glycol, or an ether or ester derivative thereof, a polyol, e.g., glycerol, pentaerythritol or tris(2-hydroxyethyl)isocyanurate, an organic amine, e.g., triethanol amine, diethanol amine or monoethanol amine, or a salt thereof, an organic sulfonic acid, e.g., an alkyl sulfonic acid, toluene sulfonic acid or benzene sulfonic acid, or a salt thereof, an organic sulfamic acid, e.g., an alkyl sulfamic acid, or a salt thereof, an organic sulfuric acid, e.g., an alkyl sulfuric acid or an alkyl ether sulfuric acid, or a salt thereof, an organic phosphonic acid, e.g., phenyl phosphonic acid, or a salt thereof, an organic carboxylic acid, e.g., tartaric acid, oxalic acid, citric acid, malic acid, lactic acid, gluconic acid or an amino acid, or a salt thereof and a betaine.

According to the invention, it is preferred that at least one compound selected from a polyol, an organic sulfate, an organic sulfonate and a betaine is incorporated.

Specific examples of the organic sulfonate include an alkylsulfonate, for example, sodium n-butylsulfonate, sodium n-hexylsulfonate, sodium 2-ethylhexylsulfonate, sodium cyclohexylsulfonate or sodium n-octylsulfonate; an alkylsulfonate containing an ethylene oxide chain, for example, sodium 5,8,11-trioxapentadecane-1-sulfonate, sodium 5,8,11-trioxaheptadecane-1-sulfonate, sodium 13-ethyl-5,8,11-trioxaheptadecane-1-sulfonate or sodium 5,8,11,14-tetraoxatetracosane-1-sulfonate; an arylsulfonate, for example, sodium benzenesulfonate, sodium p-toluenesulfonate, sodium p-hydroxybenzenesulfonate, sodium p-styrenesulfonate, sodium isophthalic acid dimethyl-5-sulfonate, sodium 1-naphtylsulfonate, sodium 4-hydroxynaphtylsulfonate, disodium 1,5-naphtyldisulfonate or trisodium 1,3,6-naphtyltrisulfonate; and compounds described in Paragraph Nos. [0026] to [0031] of JP-A-2007-276454 and Paragraph Nos. [0020] to [0047] of JP-A-2009-154525. The salt may also be a potassium salt or a lithium salt.

The organic sulfate includes a sulfate of alkyl, alkenyl, alkynyl, aryl or heterocyclic monoether of polyethylene oxide. The number of ethylene oxide unit is preferably from 1 to 4. The salt is preferably a sodium salt, a potassium salt or a lithium salt. Specific examples thereof include compounds described in Paragraph Nos. [0034] to [0038] of JP-A-2007-276454.

As the betaine, a compound wherein a number of carbon atoms included in a hydrocarbon substituent on the nitrogen atom is from 1 to 5 is preferred. Specific examples thereof include trimethylammonium acetate, dimethylpropylammonium acetate, 3-hydroxy-4-trimethylammoniobutyrate, 4-(1-pyridinio)butyrate, 1-hydroxyethyl-1-imidazolioacetate, trimethylammonium methanesulfonate, dimethylpropylammonium methanesulfonate, 3-trimethylammonio-1-porpanesulfonate and 3-(1-pyridinio)-1-porpanesulfonate.

Since the hydrophilic low molecular weight compound has a small structure of hydrophobic portion and almost no surface active function, degradations of the hydrophobicity and film strength in the image area due to penetration of dampening water into the exposed area (image area) of the image-recording layer are prevented and thus, the ink receptivity and printing durability of the image-recording layer can be preferably maintained.

The addition amount of the hydrophilic low molecular weight compound in the image-recording layer is preferably from 0.5 to 20% by weight, more preferably from 1 to 15% by weight, still more preferably from 2 to 10% by weight, based on the total solid content of the image-recording layer. In the range described above, good on-press development property and good printing durability are achieved.

The hydrophilic low molecular weight compounds may be used individually or as a mixture of two or more thereof.

(2) Oil-Sensitizing Agent

In order to improve the ink receptivity, an oil-sensitizing agent, for example, a phosphonium compound, a nitrogen-containing low molecular weight compound or an ammonium group-containing polymer can be used in the image-recording layer according to the invention. In particular, in the case where an inorganic stratiform compound is incorporated into a protective layer, the oil-sensitizing agent functions as a surface covering agent of the inorganic stratiform compound and prevents deterioration of the ink receptivity during printing due to the inorganic stratiform compound.

As preferred examples of the phosphonium compound, phosphonium compounds described in JP-A-2006-297907 and JP-A-2007-50660 are exemplified. Specific examples of the phosphonium compound include tetrabutylphosphonium iodide, butyltriphenylphosphonium bromide, tetraphenylphosphonium bromide, 1,4-bis(triphenylphosphonio)butane di(hexafluorophosphate), 1,7-bis(triphenylphosphonio)heptane sulfate and 1,9-bis(triphenylphosphonio)nonane naphthalene-2,7-disulfonate.

As the nitrogen-containing low molecular weight compound, an amine salt and a quaternary ammonium salt are exemplified. Also, an imidazolinium salt, a benzimidazolinium salt, a pyridinium salt and a quinolinium salt are exemplified. Of the nitrogen-containing low molecular weight compounds, the quaternary ammonium salt and pyridinium salt are preferably used. Specific examples the nitrogen-containing low molecular weight compound include tetramethylammonium hexafluorophosphate, tetrabutylammonium hexafluorophosphate, dodecyltrimethylammonium p-toluenesulfonate, benzyltriethylammonium hexafluorophosphate, benzyldimethyloctylammonium hexafluorophosphate, benzyldimethyldodecylammonium hexafluorophosphate and compounds described in Paragraph Nos. [0021] to [0037] of JP-A-2008-284858 and Paragraph Nos. [0030] to [0057] of JP-A-2009-90645.

The ammonium group-containing polymer may be any polymer containing an ammonium group in its structure and is preferably a polymer containing from 5 to 80% by mole of (meth)acrylate having an ammonium group in its side chain as a copolymerization component. Specific examples thereof include compounds described in Paragraph Nos. [0089] to [0105] of JP-A-2009-208458.

As to the ammonium group-containing polymer, its reduced specific viscosity value (unit: ml/g) determined according to the measuring method described in JP-A-2009-208458 is preferably in a range from 5 to 120, more preferably in a range from 10 to 110, and particularly preferably in a range from 15 to 100. When the reduced specific viscosity value described above is calculated in terms of weight average molecular weight (Mw), from 10,000 to 150,000 is preferred, from 17,000 to 140,000 is more preferred, and 20,000 to 130,000 is particularly preferred.

Specific examples of the ammonium group-containing polymer are set forth below. (1) 2-(Trimethylammonio)ethyl methacrylate p-toluenesulfonate/3,6-dioxaheptyl methacrylate copolymer (molar ratio: 10/90, Mw: 45,000) (2) 2-(Trimethylammonio)ethyl methacrylate hexafluorophosphate/3,6-dioxaheptyl methacrylate copolymer (molar ratio: 20/80, Mw: 60,000) (3) 2-(Ethyldimethylammonio)ethyl methacrylate p-toluenesulfonate/hexyl methacrylate copolymer (molar ratio: 30/70, Mw: 45,000) (4) 2-(Trimethylammonio)ethyl methacrylate hexafluorophosphate/2-ethylhexyl methacrylate copolymer (molar ratio: 20/80, Mw: 60,000) (5) 2-(Trimethylammonio)ethyl methacrylate methylsulfate/hexyl methacrylate copolymer (molar ratio: 40/60, Mw: 70,000) (6) 2-(Butyldimethylammonio)ethyl methacrylate hexafluorophosphate/3,6-dioxaheptyl methacrylate copolymer (molar ratio: 25/75, Mw: 65,000) (7) 2-(Butyldimethylammonio)ethyl acrylate hexafluorophosphate/3,6-dioxaheptyl methacrylate copolymer (molar ratio: 20/80, Mw: 65,000) (8) 2-(Butyldimethylammonio)ethyl methacrylate 13-ethyl-5,8,11-trioxa-1-heptadecanesulfonate/3,6-dioxaheptyl methacrylate copolymer (molar ratio: 20/80, Mw: 75,000) (9) 2-(Butyldimethylammonio)ethyl methacrylate hexafluorophosphate/3,6-dioxaheptyl methacrylate/ 2-hydroxy-3-methacryloyloxypropyl methacrylate copolymer (molar ratio: 15/80/5, Mw: 65,000)

The content of the oil-sensitizing agent is preferably from 0.01 to 30.0% by weight, more preferably from 0.1 to 15.0% by weight, still more preferably from 1 to 10% by weight, based on the total solid content of the image-recording layer.

(3) Other Components

Other components, for example, a surfactant, a coloring agent, a print-out agent, a polymerization inhibitor, a higher fatty acid derivative, a plasticizer, an inorganic fine particle, an inorganic stratiform compound, a co-sensitizer or a chain transfer agent may further be added to the image-recording layer. Specifically, compounds and addition amounts thereof described, for example, in Paragraph Nos. [0114] to [0159] of JP-A-2008-284817, Paragraph Nos. [0023] to [0027] of JP-A-2006-91479 and Paragraph No. [0060] of U.S. Patent Publication No. 2008/0311520 are preferably used.

(Formation of Image-Recording Layer)

The image-recording layer according to the invention is formed by dispersing or dissolving each of the necessary components described above in a known solvent to prepare a coating solution and coating the solution on a support by a known method, for example, bar coater coating and drying as described, for example, in Paragraph Nos. [0142] to [0143] of JP-A-2008-195018. The coating amount (solid content) of the image-recording layer formed on the support after coating and drying may be varied according to the intended purpose but is in general preferably from 0.3 to 3.0 g/m$^2$. In the range described above, good sensitivity and good film property of the image-recording layer can be achieved.

[Undercoat Layer]

In the lithographic printing plate precursor according to the invention, it is preferred to provide an undercoat layer (also referred to as an intermediate layer) between the image-recording layer and the support. The undercoat layer strengthens adhesion between the support and the image-recording layer in the exposed area and makes removal of the image-recording layer from the support easy in the unexposed area, thereby contributing improvement in the development property without accompanying degradation of the printing durability. Further, in the case of infrared laser exposure, since the undercoat layer acts as a heat insulating layer, decrease in sensitivity due to diffusion of heat generated upon the exposure into the support is prevented.

As a compound for use in the undercoat layer, a polymer having an adsorbing group capable of adsorbing to a surface of support and a hydrophilic group is exemplified. A polymer having a crosslinkable group as well as the adsorbing group and hydrophilic group is preferred for the purpose of improving an adhesion property to the image-recording layer. The compound may be a low molecular weight compound or a polymer compound. The compounds may be used in mixture of two or more thereof, if desired.

As the polymer compound, a copolymer of a monomer having an adsorbing group, a monomer having a hydrophilic group and a monomer having a crosslinkable group is preferred.

As the adsorbing group capable of adsorbing to a surface of support, a phenolic hydroxy group, a carboxyl group, $-PO_3H_2$, $-OPO_3H_2$, $-CONHSO_2-$, $-SO_2NHSO_2-$ or $-COCH_2COCH_3$ is preferred. As the hydrophilic group, a sulfo group, a salt thereof or a salt of carboxyl group is preferred. As the crosslinkable group, for example, a methacryl group or an allyl group is preferred.

The polymer compound may contain a crosslinkable group introduced by a salt formation between a polar substituent of the polymer compound and a compound containing a substituent having a counter charge to the polar substituent of the polymer compound and an ethylenically unsaturated bond and may also be further copolymerized with a monomer other than those described above, preferably a hydrophilic monomer.

Specifically, a silane coupling agent having an addition-polymerizable ethylenic double bond reactive group described in JP-A-10-282679 and a phosphorus compound having an ethylenic double bond reactive group described in JP-A-2-304441 are preferably exemplified. Low molecular weight compounds or polymer compounds having a crosslinkable group (preferably an ethylenically unsaturated bond group), a functional group capable of interacting with a surface of support and a hydrophilic group described in JP-A-2005-238816, JP-A-2005-125749, JP-A-2006-239867 and JP-A-2006-215263 are also preferably used.

Polymer compounds having an adsorbing group capable of adsorbing to a surface of support, a hydrophilic group and a crosslinkable group described in JP-A-2005-125749 and JP-A-2006-188038 are more preferred.

The content of the unsaturated double bond in the polymer compound for undercoat layer is preferably from 0.1 to 10.0 mmol, most preferably from 0.2 to 5.5 mmol, based on 1 g of the polymer compound.

The weight average molecular weight of the polymer compound for undercoat layer is preferably 5,000 or more, and more preferably from 10,000 to 300,000.

The undercoat layer according to the invention may contain a chelating agent, a secondary or tertiary amine, a polymerization inhibitor or a compound containing an amino group or a functional group having polymerization inhibition ability and a group capable of interacting with a surface of aluminum support (for example, 1,4-diazabicyclo [2,2,2]octane (DABCO), 2,3,5,6-tetrahydroxy-p-quinone, chloranil, sulfophthalic acid, hydroxyethylethylenediaminetriacetic acid, dihydroxyethylethylenediaminediacetic acid or hydroxyethyliminodiacetic acid) in addition to the compound for the undercoat layer described above in order to prevent the occurrence of stain due to the lapse of time.

The undercoat layer is coated according to a known method. The coating amount (solid content) of the undercoat layer is preferably from 0.1 to 100 mg/m$^2$, and more preferably from 1 to 30 mg/m$^2$.

[Protective Layer]

In the lithographic printing plate precursor according to the invention, it is preferred to provide a protective layer (an overcoat layer) on the image-recording layer. The protective layer has a function for preventing, for example, occurrence of scratch in the image-recording layer or ablation caused by exposure with high illuminance laser, in addition to the function for restraining an inhibition reaction against the image formation by means of oxygen blocking.

With respect to the protective layer having such properties, there are described, for example, in U.S. Pat. No. 3,458,311 and JP-B-55-49729. As a polymer having low oxygen permeability for use in the protective layer, any water-soluble polymer and water-insoluble polymer can be appropriately selected to use. The polymers may be used in mixture of two or more thereof, if desired. Specifically, for example, polyvinyl alcohol, a modified polyvinyl alcohol, polyvinyl pyrrolidone, a water-soluble cellulose derivative and poly(meth)acrylonitrile are exemplified.

As the modified polyvinyl alcohol, an acid-modified polyvinyl alcohol having a carboxyl group or a sulfo group is preferably used. Specifically, modified polyvinyl alcohols described in JP-A-2005-250216 and JP-A-2006-259137 are preferably exemplified.

The protective layer according to the invention preferably contains an inorganic stratiform compound in order to enhancing the oxygen blocking property. The inorganic stratiform compound is a particle having a thin tabular shape and includes, for instance, mica, for example, natural mica or synthetic mica, talc represented by the following formula: $3MgO.4SiO.H_2O$, taeniolite, montmorillonite, saponite, hectorite and zirconium phosphate.

The inorganic stratiform compound preferably used in the invention is a mica compound. As the mica compound, mica, for example, natural mica represented by the following formula: A $(B,C)_{2\text{-}5}$ $D_4$ $O_{10}$ $(OH, F, O)_2$, (wherein A represents any one of K, Na and Ca, B and C each represents any one of Fe(II), Fe(III), Mn, Al, Mg and V, and D represents Si or Al) or synthetic mica is exemplified.

Of the micas, examples of the natural mica include muscovite, paragonite, phlogopite, biotite and lepidolite. Examples of the synthetic mica include non-swellable mica, for example, fluorphlogopite $KMg_3(AlSi_3O_{10})F_2$ or potassium tetrasilic mica $KMg_{2.5}(Si_4O_{10})F_2$, and swellable mica, for example, Na tetrasilic mica $NaMg_{2.5}(Si_4O_{10})F_2$, Na or Li teniolite (Na, Li)$Mg_2Li(Si_4O_{10})F_2$, or montmorillonite based Na or Li hectorite (Na, Li)$_{1/8}Mg_{2/5}Li_{1/8}(Si_4O_{10})F_2$. Synthetic smectite is also useful.

Of the mica compounds, fluorine based swellable mica is particularly useful in the invention. Specifically, the swellable synthetic mica has a stratiform structure comprising a unit crystal lattice layer having thickness of approximately from 10 to 15 angstroms, and metallic atom substitution in the lattices thereof is remarkably large in comparison with other clay minerals. As a result, the lattice layer results in lack of positive charge and in order to compensate it, a cation, for example, Li$^+$, Na$^+$, Ca$^{2+}$ or Mg$^{2+}$, is adsorbed between the lattice layers. The cation existing between the lattice layers is referred to as an exchangeable cation and is exchangeable with various cations. In particular, in the case where the cation between the lattice layers is Li+ or Na$^+$, because of a small ionic radius, a bond between the stratiform crystal lattices is week, and the inorganic stratiform compound greatly swells upon contact with water. When share is applied under such a condition, the stratiform crystal lattices are easily cleaved to form a stable sol in water. The swellable synthetic mica has strongly such tendency and is particularly preferably used in the invention.

With respect to the shape of the mica compound, the thinner the thickness or the larger the plane size, as long as smoothness of coated surface and transmission of actinic radiation are not damaged, the better from the standpoint of control of diffusion. Therefore, an aspect ratio of the mica compound is ordinarily 20 or more, preferably 100 or more, particularly preferably 200 or more. The aspect ratio is a ratio of major axis to thickness of particle and can be determined, for example, from a projection drawing of particle by a microphotography. The larger the aspect ratio, the greater the effect obtained.

As to the particle size of the mica compound, an average major axis is from 0.3 to 20 μm, preferably from 0.5 to 10 μm, particularly preferably from 1 to 5 μm. An average thickness of the particle is 0.1 μm or less, preferably 0.05 μm or less, particularly preferably 0.01 μm or less. Specifically, for example, in the swellable synthetic mica which is the representative compound, the thickness is approximately from 1 to 50 nm and the plane size (major axis) is approximately from 1 to 20 μm.

The content of the inorganic stratiform compound is preferably from 0 to 60% by weight, more preferably from 3 to 50% by weight, based on the total solid content of the protective layer. In the case where a plural kind of the mica compounds is used together, it is preferred that the total amount of the mica compounds is in the range described above.

In the range described above, the oxygen blocking property is increased and good sensitivity is obtained. Also, deterioration of the ink receptivity can be prevented.

Also, the protective layer may contain known additives, for example, a plasticizer for imparting flexibility, a surfactant for improving coating property or an inorganic fine particle for controlling a surface slipping property. Further, the oil-sensitizing agent described with respect to the image-recording layer may also be incorporated into the protective layer.

The protective layer can be coated by a known method. The coating amount of the protective layer is preferably in a range from 0.01 to 10 g/m$^2$, more preferably in a range from 0.02 to 3 g/m$^2$, most preferably in a range from 0.02 to 1 g/m$^2$, in terms of the coating amount after drying.

[Support]

As the support for use in the lithographic printing plate precursor according to the invention, a known support is employed. Particularly, an aluminum plate subjected to roughening treatment and anodizing treatment according to a known method is preferred.

Also, an enlarging treatment or a sealing treatment of micropores of the anodized film described in JP-A-2001-253181 and JP-A-2001-322365 or a surface hydrophilizing treatment, for example, with an alkali metal silicate as described in U.S. Pat. Nos. 2,714,066, 3,181,461, 3,280,734 and 3,902,734 or polyvinyl phosphonic acid as described in U.S. Pat. Nos. 3,276,868, 4,153,461 and 4,689,272 may be appropriately selected and applied to the aluminum plate, if desired.

The support preferably has a center line average roughness of 0.10 to 1.2 μm.

The support according to the invention may have a backcoat layer containing an organic polymer compound described in JP-A-5-45885 or an alkoxy compound of silicon described in JP-A-6-35174, provided on the back surface thereof, if desired.

[Plate Making Method]

The plate making method of the lithographic printing plate precursor according to the invention is preferably a method including at least a process of image exposure of the lithographic printing plate precursor (hereinafter, also referred to as a "exposure process") and a process of development processing of the exposed lithographic printing plate precursor with a processing solution (hereinafter, also referred to as a "development process").

<Exposure Process>

Although the lithographic printing plate precursor for use in the invention can be subjected to image recording by a method of scanning exposure of digital data by laser, for example, visible laser or infrared laser or a method of exposing through a transparent original having an image recorded using a light source, for example, a halogen lamp or a high-pressure mercury lamp, the method of scanning exposure of digital data by laser, for example, visible laser or infrared laser is preferred.

The wavelength of the exposure light source is desirably from 300 to 450 nm or from 750 to 1,400 nm. In the case of exposing with light of 300 to 450 nm, the lithographic printing plate precursor having an image-recording layer containing a sensitizing dye having an absorption maximum in such a wavelength range is used. In the case of exposing with light of 750 to 1,400 nm, the lithographic printing plate precursor containing an infrared absorbing agent which is a sensitizing dye having an absorption maximum in such a wavelength range is used. As the light source of 300 to 450 nm, a semiconductor laser is preferably used. As the light source of 750 to 1,400 nm, a solid laser or semiconductor laser emitting an infrared ray is preferably used. The exposure mechanism may be any of an internal drum system, an external drum system and a flat bed system.

<Development Process>

After the exposure, the lithographic printing plate precursor for use in the invention is developed with water or a developer having pH from 2 to 14 (developer processing) or developed with dampening water and ink on a printing machine (on-press development).

The developer processing is ordinarily practiced according to the following processes: (1) removing the non-image area with a developer, (2) conducting gumming solution treatment and (3) drying in a drying process. Although the lithographic printing plate precursor for use in the invention can be developed according to the ordinary processes described above (conventional development), it is preferred to conduct processes (1) and (2) simultaneously (simple development). In any of the development methods, a water washing process for removing a protective layer may be provided before process (1). The development of process (1) is conducted according to a conventional manner at temperature approximately from 0 to 60° C., preferably approximately from 15 to 40° C., using, for example, a method wherein the lithographic printing plate precursor subjected to the exposure treatment is immersed in a developer and rubbed with a brush or a method wherein a developer is sprayed to the lithographic printing plate precursor subjected to the exposure treatment by a spray and the lithographic printing plate precursor is rubbed with a brush.

In the case of the conventional development, a water washing process for removing an excess developer may be provided between process (1) and process (2). The developer used in process (1) is preferably a known alkali developer.

In the case of the simple development, it is preferred that after the development and gumming treatment, an excess developer is removed using a squeeze roller and then drying is conducted.

The developer for use in the simple development is an aqueous solution having pH from 2 to 11. An aqueous solution containing water as the main component (containing 60% by weight or more of water) is preferred. In particular, an aqueous solution containing a surfactant (for example, an anionic, nonionic, cationic or amphoteric surfactant) or an aqueous solution containing a water-soluble polymer compound is preferred. An aqueous solution containing both the surfactant and the water-soluble polymer compound is also preferred. The pH of the developer is preferably from 5 to 10.7, more preferably from 6 to 10.5, and most preferably from 7.5 to 10.3.

The anionic surfactant for use in the developer for the simple development is not particularly limited and includes, for example, fatty acid salts, abietic acid salts, hydroxyalkanesulfonic acid salts, alkanesulfonic acid salts, dialkylsulfosuccinic acid salts, straight-chain alkylbenzenesulfonic acid salts, branched alkylbenzenesulfonic acid salts, alkylnaphthalenesulfonic acid salts, alkyldiphenylether (di)sulfonic acid salts, alkylphenoxy polyoxyethylene propylalkylsulfonic acid salts, polyoxyethylene alkylsulfophenyl ether salts, N-methylalkyl-N-oleyltaurine sodium salts, N-alkylsulfosuccinic acid monoamide disodium salts, petroleum sulfonic acid salts, sulfated castor oil, sulfated beef tallow oil, sulfate ester slats of fatty acid alkyl ester, alkyl sulfate ester salts, polyoxyethylene alkyl ether sulfate ester salts, fatty acid monoglyceride sulfate ester salts, polyoxyethylene alkyl phenyl ether sulfate ester salts, polyoxyethylene styryl phenyl ether sulfate ester salts, alkyl phosphate ester salts, polyoxyethylene alkyl ether phosphate ester salts, polyoxyethylene alkyl phenyl ether phosphate ester salts, partially saponified products of styrene-maleic anhydride copolymer, partially saponified products of olefin-maleic anhydride copolymer and naphthalene sulfonate formalin condensates. Of the compounds, alkylbenzenesulfonic acid salts, alkylnaphthalenesulfonic acid salts and alkyldiphenylether (di)sulfonic acid salts are particularly preferably used.

The cationic surfactant for use in the developer for the simple development is not particularly limited and conventionally known cationic surfactants can be used. Examples of the cationic surfactant include alkylamine salts, quaternary ammonium salts, alkylimidazolinium salts, polyoxyethylene alkyl amine salts and polyethylene polyamine derivatives.

The nonionic surfactant for use in the developer for the simple development is not particularly limited and includes, for example, polyethylene glycol type higher alcohol ethylene oxide adducts, alkylphenol ethylene oxide adducts, alkylnaphthol ethylene oxide adducts, phenol ethylene oxide adducts, naphthol ethylene oxide adducts, fatty acid ethylene oxide adducts, polyhydric alcohol fatty acid ester ethylene oxide adducts, higher alkylamine ethylene oxide adducts, fatty acid amide ethylene oxide adducts, ethylene oxide addacts of fat, polypropylene glycol ethylene oxide adducts, dimethylsiloxane-ethylene oxide block copolymers, dimethylsiloxane-(propylene oxide-ethylene oxide) block copolymers, fatty acid esters of polyhydric alcohol type glycerol, fatty acid esters of pentaerythritol, fatty acid esters of sorbitol and sorbitan, fatty acid esters of sucrose, alkyl ethers of polyhydric alcohols and fatty acid amides of alkanolamines. Of the compounds, those having an aromatic ring and an ethylene oxide chain are preferred and alkyl-substituted or unsubstituted phenol ethylene oxide adducts and alkyl-substituted or unsubstituted naphthol ethylene oxide adducts are more preferred.

The amphoteric surfactant for use in the developer for the simple development is not particularly limited and includes, for example, amine oxide type, for example, alkyldimethylamine oxide, betaine type, for example, alkyl betaine, and amino acid type, for example, sodium salt of alkylamino fatty acid. In particular, alkyldimethylamine oxide which may have a substituent, alkyl carboxy betaine which may have a substituent and alkyl sulfo betaine which may have a substituent are preferably used. As specific examples thereof, compounds represented by formula (2) described in Paragraph Nos. [0255] to [0278] of JP-A-2008-203359, compounds represented by formulae (I), (II) and (VI) described in Paragraph Nos. [0028] to [0052] of JP-A-2008-276166 and compounds described in Paragraph Nos. [0022] to [0029] of JP-A-2009-47927 may be used.

Two or more kinds of the surfactants may be used in combination. The proportion of the surfactant contained in the developer is preferably from 0.01 to 20% by weight, and more preferably from 0.1 to 10% by weight.

Further, in the plate making process of preparing a lithographic printing plate from the lithographic printing plate precursor according to the invention, the lithographic printing plate precursor may be heated its entire surface before or during the exposure or between the exposure and the development, if desired. By the heating, the image-forming reaction in the image-recording layer is accelerated and advantages, for example, improvement in the sensitivity and printing durability and stabilization of the sensitivity are achieved. For the purpose of increasing the image strength and printing durability, it is also effective to perform entire after-heating or entire exposure of the image after the development. Ordinarily, the heating before the development is preferably performed under a mild condition of 150° C. or lower. When the temperature is too high, a problem may arise sometimes in that the unexposed area is also cured. On the other hand, the heating after the development can be performed using very strong conditions. Ordinarily, the heat treatment is carried out in a temperature range from 100 to 500° C. When the temperature is too low, a sufficient effect of strengthening the image may not be obtained, whereas when it is excessively high, problems of deterioration of the support and thermal decomposition of the image area may occur sometimes.

The lithographic printing plate precursor according to the invention can also be subjected to plate making by an on-press development method. The on-press development method includes a process in which the lithographic printing plate precursor is imagewise exposed and a printing process in which oily ink and an aqueous component are supplied to the exposed lithographic printing plate precursor without undergoing any development processing to perform printing, and it is characterized in that the unexposed area of the lithographic printing plate precursor is removed in the course of the printing process. The imagewise exposure may be performed on a printing machine after the lithographic printing plate precursor is mounted on the printing machine or may be separately performed using a platesetter or the like. In the latter case, the exposed lithographic printing plate precursor is mounted as it is on a printing machine without undergoing a development processing process. Then, the printing operation is initiated using the printing machine with supplying oily ink and an aqueous component and at an early stage of the printing the on-press development is carried out. Specifically, the image-recording layer in the unexposed area is removed and the hydrophilic surface of support is revealed therewith to form the non-image area. As the oily ink and aqueous component, printing ink and dampening water for conventional lithographic printing can be employed, respectively.

While either the dampening water or printing ink may be supplied at first on the surface of lithographic printing plate precursor, it is preferred to supply the printing ink at first in view of preventing the dampening water from contamination with the component of the image-recording layer removed.

Thus, the lithographic printing plate precursor according to the invention is subjected to the on-press development on an offset printing machine and used as it is for printing a large number of sheets.

EXAMPLES

The invention will be described in more detail with reference to the following examples, but the invention should not be construed as being limited thereto. With respect to the polymer compounds used in the examples, unless otherwise particularly defined, a molecular weight means a weight average molecular weight (Mw) and a ratio of repeating units is indicated in mole percent.

I. Synthesis Method of Specific Compound According to Invention

I-1. Synthesis Method of Intermediate (1)

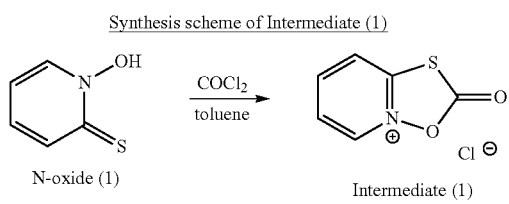

To a solution of COCl$_2$ (20% by weight toluene solution, 69.3 g (140 mmol)) and 100 g of toluene was added dropwise a solution of N-oxide (1) (8.25 g (65 mmol)) and 20 g of toluene at room temperature over a period of 30 minutes. After the completion of the dropwise addition, the mixture was stirred for 30 minutes, and the precipitate generated was washed with toluene and collected by filtration to obtain Intermediate (1) (10.6 g (55.9 mmol)). Yield: 86%.

The structure of Intermediate (1) obtained was identified by NMR. The identification result is shown below.

($^1$H-NMR 300 MHz deuterated dimethylsulfoxide): 8.00 (dd, 1H), 8.07 (d, 1H), 8.58 (dd, 1H), 8.57 (d, 1H)

I-2. Synthesis Method of Specific Compound 1

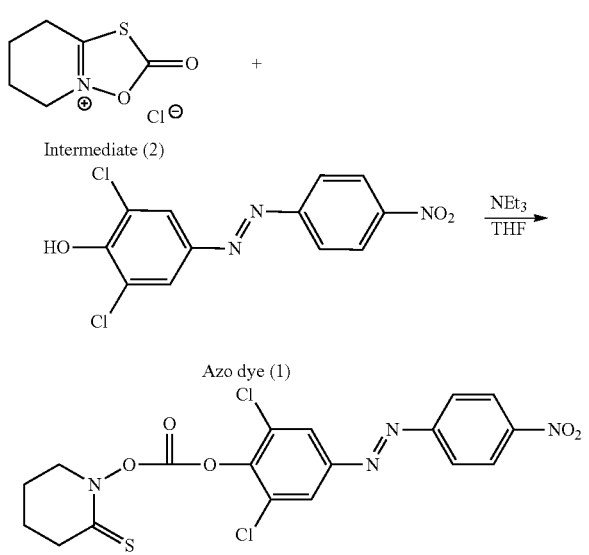

A tetrahydrofuran solution (50 g) of 38.7 g (0.200 mol) of Intermediate (2) synthesized in the same manner as in Synthesis method of Intermediate (1) described above was added dropwise to a tetrahydrofuran mixed solution (50 ml) in which 62.4 g (0.200 mol) of Azo dye (1) synthesized in the same manner as in the method described in the literature shown below and 23.4 g (0.232 mol) of triethylamine had been dissolved. After the completion of dropwise addition, the solution was stirred at 60° C. for one hour. The reaction solution was added dropwise to distilled water (2,000 g) to deposit a solid. The solid obtained was recrystallized from ethanol to obtain 61 g (0.130 mol) of Specific compound 1. Yield: 65%.

The structure of the product obtained was identified by NMR. The identification result is shown below.

($^1$H-NMR 300 MHz)

Intermediate (2) (deuterated dimethylsulfoxide): 1.08~1.24 (m 4H), 2.01~2.22 (m, 2H), 4.08~4.23 (m, 2H)

Specific compound I (deuterated chloroform): 1.06~1.24 (m 4H), 2.03~2.24 (m, 2H), 2.51~2.69 (m, 2H), 7.94 (s, 2H), 7.85 (d, 2H), 8.30 (d, 2H)

Note: Literature for synthesis of Azo dye (1): *Arg. Biol. Chem.*, Vol. 34, No. 7, 1014-1019 (1970)

I-3. Synthesis Method of Specific Compound 13

Synthesis scheme of Specific compound 13

Using 37.9 g (0.200 mol) of Intermediate (1) and 62.4 g (0.200 mol) of Azo dye (1), 64.2 g (0.138 mol) of Specific compound 13 was obtained in the same manner as in the synthesis method of Specific compound I according to the synthesis scheme described above. Yield: 69%. The structure of the product obtained was identified by NMR. The identification result is shown below.

($^1$H-NMR 300 MHz deuterated chloroform): 6.05 (dd 1H), 7.45 (dd 1H), 7.51 (dd 1H), 7.90 (dd 1H), 7.94 (s, 2H), 7.85 (d, 2H), 8.30 (d, 2H)

I-4. Synthesis Method of Specific Compound 60

Synthesis scheme of Specific compound 60

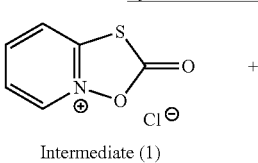

-continued

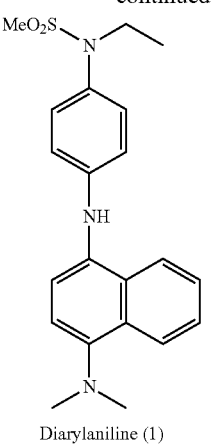

Diarylaniline (1)

$\xrightarrow{\text{NEt}_3}{\text{THF}}$

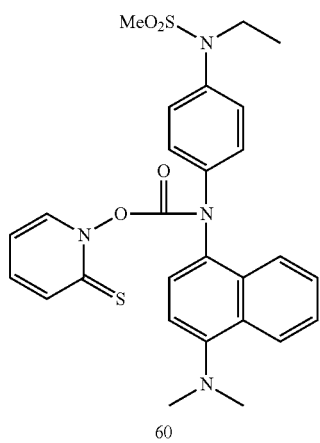

60

Using 37.9 g (0.200 mol) of Intermediate (1) and 76.7 g (0.200 mol) of Diarylaniline (1) synthesized by the method described below, 64.3 g (0.120 mol) of Specific compound 60 was obtained in the same manner as in the synthesis method of Specific compound I according to the synthesis scheme described above. Yield: 60%. The structure of the product obtained was identified by NMR. The identification result is shown below.

($^1$H-NMR 300 MHz deuterated chloroform): 1.15 (t, 3H), 3.06 (s, 6H), 3.10 (q, 2H), 3.32 (s, 3H), 6.05 (d, 1H), 6.58 (d, 2H), 6.79 (d, 1H), 6.85 (d, 1H), 7.44 (dd, 1H), 7.49~7.55 (m, 3H), 7.60 (d, 2H), 7.90 (dd, 1H), 8.01 (d, 1H), 8.05 (d, 1H)

*Synthesis of Diarylaniline (1)

Synthesis scheme

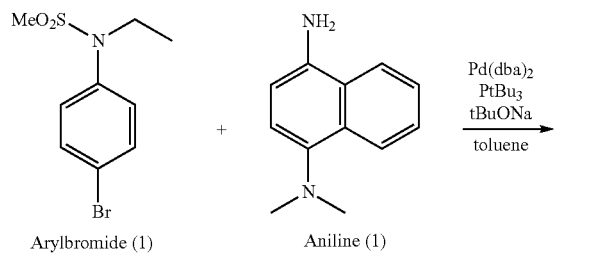

Arylbromide (1)      Aniline (1)

-continued

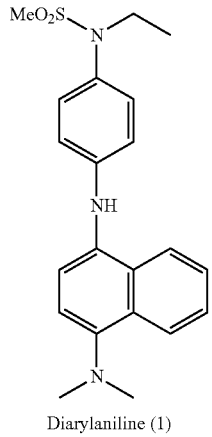

Diarylaniline (1)

Under nitrogen atmosphere, 1.86 g (6.7 mmol) of Arylbromide (1), 2.5 g (13.4 mmol) of Aniline (1), 0.16 g (0.280 mmol) of bis(dibenzylideneacetone) palladium (Pd(dba)$_2$), 0.05 g (0.250 mmol) of tri-tert-butylphosphine (PtBu$_3$) and 2.2 g (23.1 mmol) of sodium tert-butoxide were dissolved in 35 g of toluene, followed by refluxing with heating for 2 hours. After the heating, the precipitate generated was removed by filtration and the filtrate obtained was concentrated to obtain a solid. The solid was recrystallized from ethanol-hexane under nitrogen atmosphere to obtain 2.23 g (5.83 mmol) of Diarylaniline (1). Yield: 87%.

I-5. Synthesis method of Specific compound 103

Synthesis scheme of Specific compound 103

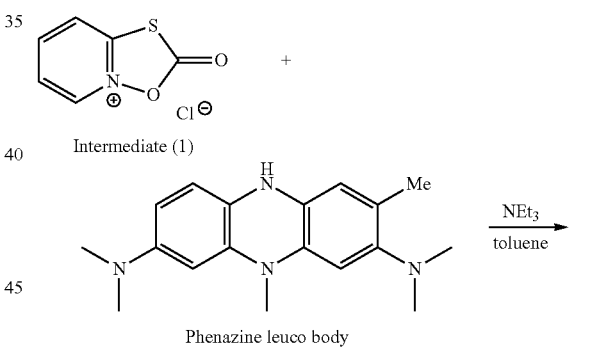

Intermediate (1)

Phenazine leuco body

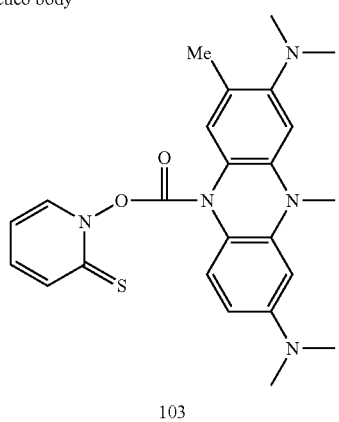

103

Using 37.9 g (0.200 mol) of Intermediate (1) and 59.3 g (0.200 mol) of Phenazine leuco body (1) synthesized by the method described below, synthesis was conducted in toluene in the same manner according to the synthesis scheme described above to obtain 48.5 g (0.108 mol) of Specific compound 103. Yield: 54%. The structure of the product obtained was identified by NMR. The identification result is shown below.

($^1$H-NMR 300 MHz deuterated chloroform): 2.12 (s, 3H), 3.06 (s, 6H), 3.09 (s, 6H), 3.20 (s, 3H), 5.73 (s, 1H), 5.85 (s, 1H), 6.04 (d, 1H), 6.21 (d, 1H), 7.33 (s, 1H), 7.41 (d, 1H), 7.47 (dd, 1H), 7.51 (d, 1H), 7.91 (dd, 1H)

*Synthesis of Phenazine Leuco Body (1)

Synthesis scheme

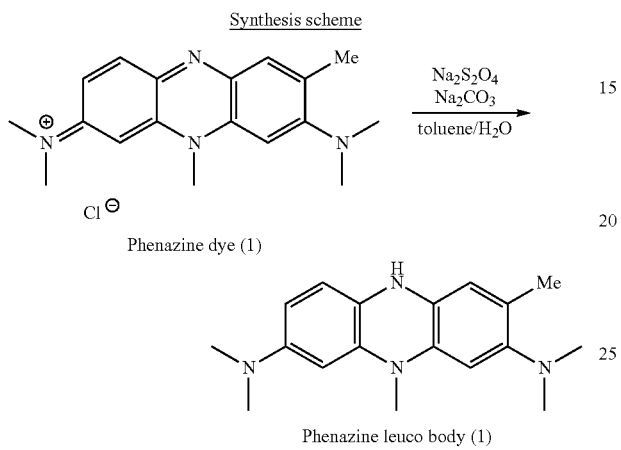

Phenazine dye (1)

Phenazine leuco body (1)

Under nitrogen atmosphere, a mixture of 6.61 g (20.0 mmol) of Phenazine dye (1) synthesized in the same manner as in the method described in the literature shown below, 10.44 g (60.0 mmol) of $Na_2S_2O_4$ and 6.36 g (60.0 mmol) of $Na_2CO_3$ was reacted in a two layer system of toluene (500 g) and water (500 g) at room temperature for 2 hours. The aqueous layer was removed by liquid separation operation to obtain a toluene solution of Phenazine leuco body (1).

Note: Literature for synthesis of Phenazine dye (1): *Molecules*, Vol. 8, No. 6, 505-519 (2003)

I-6. Synthesis Method of Specific Compound 104

Synthesis scheme of Specific compound 104

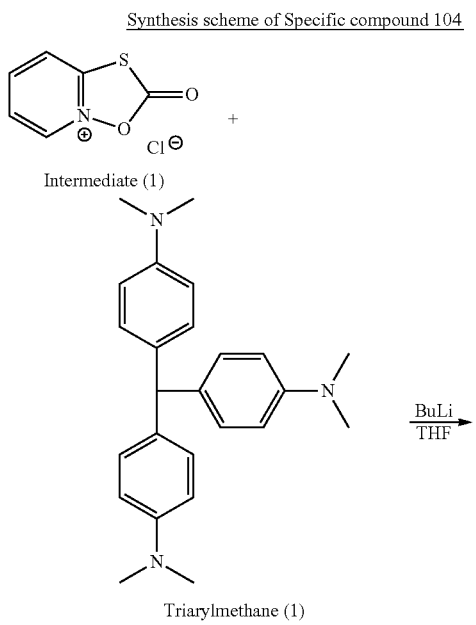

Intermediate (1)

Triarylmethane (1)

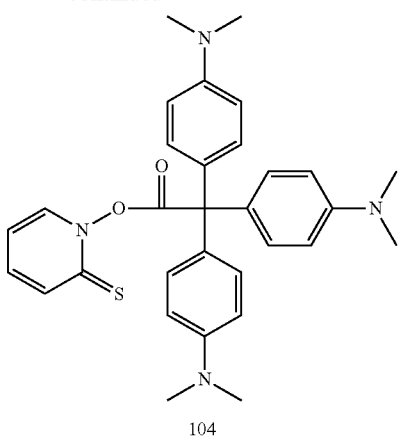

104

Under nitrogen atmosphere, 184 g (0.200 mol) of a normalbutyl lithium hexane solution (about 1.6 mol/L, specific gravity: 0.68) was added dropwise to a tetrahydrofuran (50 mL) solution of 74.6 g (0.200 mol) of Triarylmethane (1) cooled at −78° C. while maintaining an inner temperature of −60° C. or below and after the completion of the dropwise addition, the solution was stirred under the same temperature condition for one hour. To the solution was added dropwise a tetrahydrofuran (50 g) solution of 41.7 g (0.220 mol) of Intermediate (1) under the same temperature condition over a period of one hour. After the completion of dropwise addition, the mixture was raised to room temperature over a period of 6 hours or more and stirred for 12 hours. Thereafter, the reaction was quenched with water, the reaction mixture was extracted with ethyl acetate, and the organic layer was washed with water and then with an aqueous saturated sodium chloride solution and dried over magnesium sulfate. The organic solvent was distilled off and a solid obtained was recrystallized from ethanol to obtain 55.2 g (0.105 mol) of Specific compound 104. Yield: 53%.

The structure of the product obtained was identified by NMR. The identification result is shown below.

($^1$H-NMR 300 MHz deuterated chloroform): 3.06 (s, 18H), 6.05 (d, 1H), 6.64 (d, 6H), 7.05 (d, 6H), 7.45 (dd, 1H), 7.50 (d, 1H), 7.90 (dd, 1H)

I-7. Synthesis Method of Specific Compound 107

Synthesis scheme of Specific compound 107

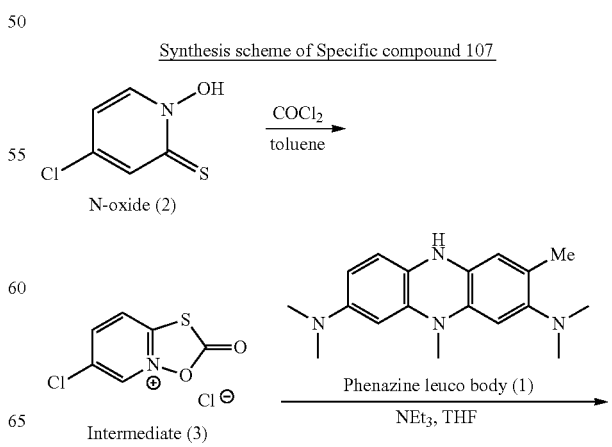

N-oxide (2)

Intermediate (3)

Phenazine leuco body (1)

$\xrightarrow{NEt_3, THF}$

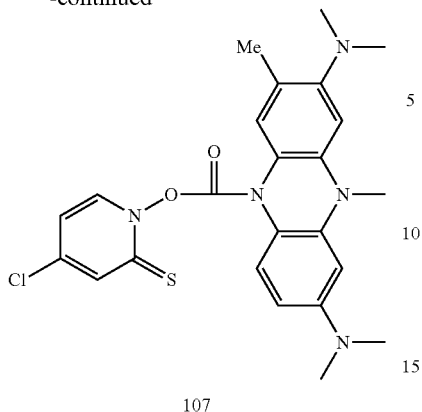

107

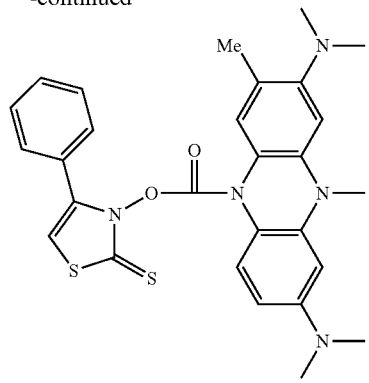

123

Using 54.3 g (0.200 mol) of Intermediate (3) synthesized in the same manner as in Synthesis method of Intermediate (1) described above using as a starting material, N-oxide (2) synthesized in the same manner as in the method described in the literature shown below and 59.3 g (0.200 mol) of Phenazine leuco body (1), synthesis was conducted in toluene in the same manner according to the synthesis scheme described above to obtain 43.0 g (0.088 mmol) of Specific compound 107. Yield: 44%.

Note: Literature for synthesis of N-oxide (2): *J. Org. Chem.*, 74(19), pp 7441-7448, (2009)

The structure of the product obtained was identified by NMR. The identification result is shown below.

($^1$H-NMR 300 MHz)

Intermediate (3) (deuterated dimethylsulfoxide): 7.21 (d, 1H), 7.35 (s, 1H), 8.43 (d, 1H)

Specific compound 107 (deuterated chloroform): 2.10 (s, 3H), 3.04 (s, 6H), 3.06 (s, 6H), 3.22 (s, 3H), 5.73 (s, 1H), 5.80 (s, 1H), 6.05 (d, 1H), 6.21 (d, 1H), 6.25 (s, 1H), 7.33 (s, 1H), 7.36 (d, 1H), 7.41 (d, 1H)

I-8. Synthesis Method of Specific Compound 123

Synthesis scheme of Specific compound 123

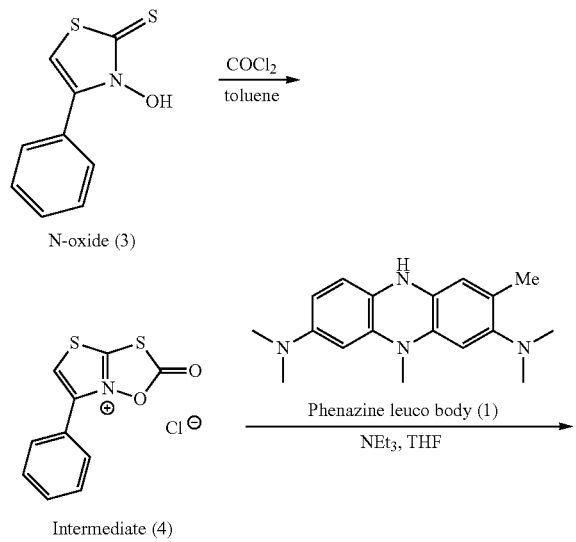

According to the synthesis scheme described above, using 54.3 g (0.200 mol) of Intermediate (4) synthesized in the same manner as in Synthesis method of Intermediate (1) described above using as a starting material, N-oxide (3) and 59.3 g (0.200 mol) of Phenazine leuco body (1), synthesis was conducted in toluene in the same manner to obtain 52.3 g (0.098 mmol) of Specific compound 123. Yield: 49%.

The structure of the product obtained was identified by NMR. The identification result is shown below.

($^1$H-NMR 300 MHz)

Intermediate (4) (deuterated dimethylsulfoxide): 7.41 (d, 1H), 7.51 (t, 2H), 7.79 (d, 2H), 8.06 (s, 1H)

Specific compound 107 (deuterated chloroform): 2.11 (s, 3H), 3.04 (s, 6H), 3.06 (s, 6H), 3.22 (s, 3H), 5.73 (s, 1H), 5.80 (s, 1H), 6.21 (d, 1H), 7.06 (s, 1H), 7.30 (s, 1H), 7.35 (d, 1H), 7.40 (t, 2H), 7.44 (d, 1H), 7.71 (d, 2H)

II. Ultraviolet Ray Color-Forming Composition Film

II-1. Production of Color-Forming Composition Films A-1 to A-2 and A-5

Color-forming composition solution (1) shown below was prepared, coated on a polyester film having a thickness of 0.18 mm using a bar so as to have a dry coating amount of 1.0 g/m² and dried in an oven at 100° C. for 60 seconds to produce Color-forming composition films A-1 to A-2 and A-5 (for Examples 1 to 2 and Example 5), respectively.

<Color-Forming Composition Solution (1)>

| | |
|---|---|
| Binder polymer (1) having structure shown below | 0.636 g |
| Radical generator (compound shown in Table 7) | 0.150 g |
| Specific compound according to invention (compound shown in Table 7) | 0.030 g |
| Fluorine-based surfactant (1) having structure shown below | 0.008 g |
| 2-Butanone | 1.091 g |
| 1-Methoxy-2-propanol | 8.609 g |
| Trinormalbutylamine | 0.051 g |

The structures of Binder polymer (1), Radical generators (1) to (3) and Fluorine-based surfactant (1) are shown below.

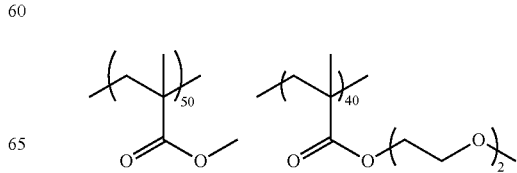

-continued

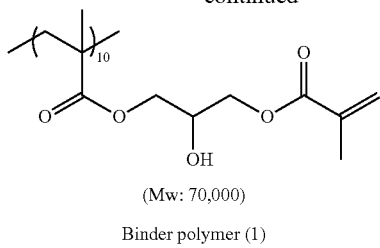

(Mw: 70,000)

Binder polymer (1)

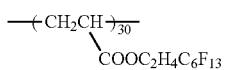

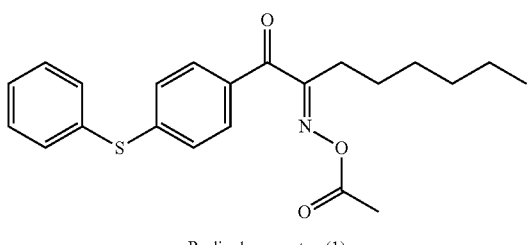

(Mw: 13,000)

Fluorine-based surfactant (1)

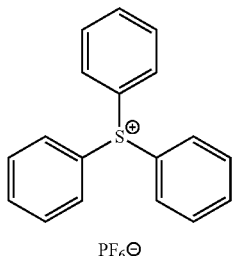

Radical generator (1)

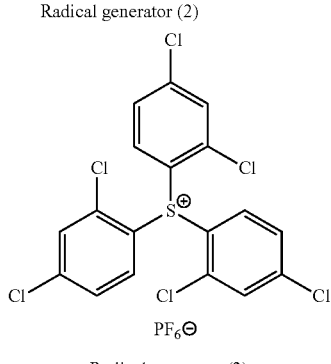

PF$_6^\ominus$

Radical generator (2)

Radical generator (3)

II-2. Production of Color-Forming Composition Films A-3 to A-4 and A-6 to A-26

Color-forming composition films A-3 to A-4 and A-6 to A-26 (for Examples 3 to 4 and Examples 6 to 26) were produced in the same manner as above except for using a color-forming composition solution in which the trinormal-butylamine in Color-forming composition solution (1) was not added, respectively.

II-3. Production of Color-forming composition film A'-1

Color-forming composition film A'-1 (for Comparative Example 1) was produced in the same manner as above except for not adding the radical generator in Color-forming composition film A-3.

II-4. Production of Color-forming composition film A'-2

Color-forming composition film A'-2 (for Comparative Example 2) was produced in the same manner as above except for using Comparative compound (1) shown below in place of Specific compound 3 in Color-forming composition film A-3.

Comparative compound (1)

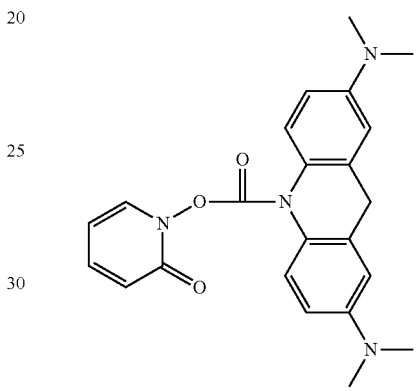

II-5. Production of Color-forming composition film A'-3

Color-forming composition solution (2) shown below was prepared, coated on a polyester film having a thickness of 0.18 mm using a bar so as to have a dry coating amount of 1.0 g/m$^2$ and dried in an oven at 100° C. for 60 seconds to produce Color-forming composition film A'-3 (for Comparative Example 3).

<Color-Forming Composition Solution (2)>

| | |
|---|---|
| Binder polymer (1) shown above | 0.636 g |
| Comparative compound (2) having structure shown below | 0.030 g |
| Fluorine-based surfactant (1) shown above | 0.008 g |
| 2-Butanone | 1.091 g |
| 1-Methoxy-2-propanol | 8.609 g |

The structure of Comparative compound (2) is shown below. Ts represents a tosyl group.

Comparative compound (2)

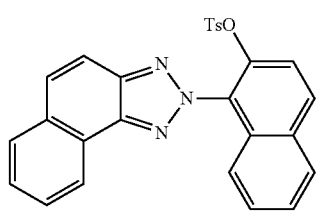

II-6. Evaluation of color-forming property of color-forming composition film

The color-forming composition film obtained was exposed using PS Light S Type (metal halide lamp, 2 KW, produced by Fujifilm Corp.) for 20 seconds at a distance of one meter.

Just after the exposure and at 2 hours lapse after the exposure kept in a dark place under room temperature condition, the color formation was measured. Also, the color-forming composition film was subjected to a forced time lapse test under conditions of 60° C. and 70% RH for 3 days and the color formation thereof just after the exposure was measured.

The color formation was measured using an L value (luminance) of L*a*b* color system and difference (ΔL) between an L value of the exposed area and an L value of the unexposed area was determined. As the value of ΔL is larger, it is meant that the color-forming property is more excellent. The measurement was conducted according to SCE (specular competent exclude) system using a spectral colorimeter CM2600d and an operation soft CM-S100 W each produced by Konica Minolta, Inc. The results are shown in Table 7.

color-forming property because the maximum absorption wavelength (λmax) of dye is present in a range from 500 to 600 nm. Further, it can be seen that the radical generator (A) is indispensable in the color-forming composition according to the invention in order to exhibit the high color-forming property.

III. Long Wavelength Responding (Visible Light) Color-Forming Composition

III-1. Production of Color-Forming Composition Films B-1 to B-2 and B-5

Color-forming composition solution (3) shown below was prepared, coated on a polyester film having a thickness of 0.18 mm using a bar so as to have a dry coating amount of 1.0 g/m$^2$ and dried in an oven at 100° C. for 60 seconds to produce Color-forming composition films B-1 to A-2 and B-5 (for Examples 27, 28 and 31), respectively.

<Color-Forming Composition Solution (3)>

| | |
|---|---|
| Binder polymer (1) shown above | 0.636 g |
| Radical generator (compound shown in Table 8) | 0.150 g |

TABLE 7

| | Color-forming Composition | Specific Compound | Radical Generator | Color-forming Property (ΔL) | | |
|---|---|---|---|---|---|---|
| | | | | Just after Exposure | After 2 Hours Lapse | After Forced Time Lapse Test |
| Example 1 | A-1 | 1 | 3 | 6 | 5.5 | 5.5 |
| Example 2 | A-2 | 2 | 3 | 6 | 5.5 | 5.5 |
| Example 3 | A-3 | 3 | 3 | 8 | 7.5 | 7.5 |
| Example 4 | A-4 | 4 | 3 | 7.5 | 7 | 7 |
| Example 5 | A-5 | 13 | 3 | 6.5 | 6 | 6 |
| Example 6 | A-6 | 15 | 3 | 8 | 7.5 | 7.5 |
| Example 7 | A-7 | 16 | 3 | 8 | 7.5 | 7.5 |
| Example 8 | A-8 | 35 | 3 | 8.5 | 8 | 8 |
| Example 9 | A-9 | 36 | 3 | 8.5 | 8 | 8 |
| Example 10 | A-10 | 47 | 3 | 8 | 7.5 | 7.5 |
| Example 11 | A-11 | 48 | 3 | 10 | 9.5 | 9.5 |
| Example 12 | A-12 | 59 | 3 | 8 | 7.5 | 7.5 |
| Example 13 | A-13 | 60 | 3 | 11 | 10.5 | 10.5 |
| Example 14 | A-14 | 79 | 3 | 8 | 7.5 | 7.5 |
| Example 15 | A-15 | 80 | 3 | 11 | 10.5 | 10.5 |
| Example 16 | A-16 | 90 | 3 | 12 | 11.5 | 11.5 |
| Example 17 | A-17 | 91 | 3 | 12.5 | 12 | 12 |
| Example 18 | A-18 | 92 | 3 | 11.5 | 11 | 11 |
| Example 19 | A-19 | 103 | 1 | 13 | 12.5 | 12.5 |
| Example 20 | A-20 | 103 | 2 | 14 | 13.5 | 13.5 |
| Example 21 | A-21 | 103 | 3 | 14.5 | 14 | 14 |
| Example 22 | A-22 | 104 | 3 | 12 | 11.5 | 11.5 |
| Example 23 | A-23 | 107 | 3 | 13 | 12.5 | 12.5 |
| Example 24 | A-24 | 108 | 3 | 12 | 11.5 | 11.5 |
| Example 25 | A-25 | 123 | 3 | 13 | 12.5 | 12.5 |
| Example 26 | A-26 | 124 | 3 | 12 | 11.5 | 11.5 |
| Comparative Example 1 | A'-1 | 3 | — | 2 | 1.5 | 1.5 |
| Comparative Example 2 | A'-2 | Comparative Compound (1) | 3 | 0.5 | 0 | 0 |
| Comparative Example 3 | A'-3 | Comparative Compound (2) | — | 5 | 4.5 | 4.5 |

From the results shown in Table 7, it can be seen that the color-forming composition film according to the invention exhibits the good color-forming property. In particular, of the specific compounds according to the invention, in the case where the dye released from R$^1$ is an indoaniline dye, a triphenylmethane dye or an azine series dye, higher color-forming property is obtained than the case where the dye released from R$^1$ is an azo dye or a cinnamylidene dye. It is also apparent that of the compounds, the compounds in which R$^1$ is Z-8, Z-16, Z-18 and Z-21 have the high -continued

| | |
|---|---|
| Specific compound according to invention (compound shown in Table 8) | 0.030 g |
| Sensitizing dye (1) having structure shown below | 0.08 g |
| Fluorine-based surfactant (1) shown above | 0.008 g |
| 2-Butanone | 1.091 g |
| 1-Methoxy-2-propanol | 8.609 g |
| Trinormalbutylamine | 0.051 g |

The structure of Sensitizing dye (1) is shown below.

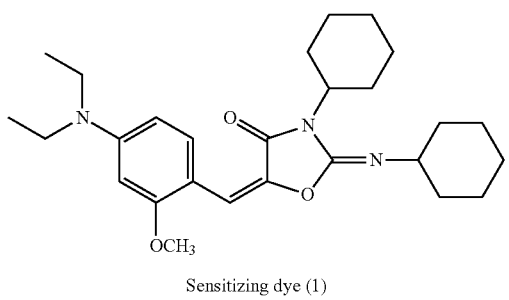 [SMILES: CCN(CC)c1ccc(/C=C2/OC(=NC3CCCCC3)N(C3CCCCC3)C2=O)c(OC)c1]

Sensitizing dye (1)

III-2. Production of Color-Forming Composition Films B-3, B-4 and B-6 to B-26

Color-forming composition films B-3, B-4 and B-6 to B-26 (for Examples 29, 30 and 32 to 52) were produced in the same manner as above except for using a color-forming composition solution in which the trinormalbutylamine in Color-forming composition solution (3) was not added, respectively.

III-3. Production of Color-Forming Composition Film B'-1

Color-forming composition film B'-1 (for Comparative Example 4) was produced in the same manner as above except for not adding the radical generator in Color-forming composition film B-3.

III-4. Production of Color-Forming Composition Film B'-2

Color-forming composition film B'-2 (for Comparative Example 5) was produced in the same manner as above except for using Comparative compound (1) in place of the specific compound in Color-forming composition film B-3.

III-5. Production of Color-Forming Composition Film B'-3

Color-forming composition solution (4) shown below was prepared, coated on a polyester film having a thickness of 0.18 mm using a bar so as to have a dry coating amount of 1.0 g/m² and dried in an oven at 100° C. for 60 seconds to produce Color-forming composition film B'-3 (for Comparative Example 6).

<Color-Forming Composition Solution (4)>

| | |
|---|---|
| Binder polymer (1) shown above | 0.636 g |
| Comparative compound (2) shown above | 0.030 g |
| Sensitizing dye (1) shown above | 0.08 g |
| Fluorine-based surfactant (1) shown above | 0.008 g |
| 2-Butanone | 1.091 g |
| 1-Methoxy-2-propanol | 8.609 g |

III-6. Evaluation of Color-Forming Property of Color-Forming Composition Film

The color-forming composition film produced was subjected to image exposure in an exposure amount of 90 μJ/cm² and resolution of 2,438 dpi (dpi indicating a number of dots per 2.54 cm). As the exposure pattern, a 50% square dot was used. As the exposure device, a violet semiconductor laser Vx9600 (InGaN semiconductor laser, emission: 405 nm±10 nm/output: 30 mW) produced by FUJIFILM Electronic Imaging Ltd. was used. The exposure was conducted under conditions of 25° C. and 50% RH.

The color formation was measured in the same manner as in the color-forming composition film described above. As the value of ΔL is larger, it is meant that the color-forming property is more excellent. The results are shown in Table 8.

TABLE 8

| | Color-forming Composition | Specific Compound | Radical Generator | Color-forming Property (ΔL) | | |
|---|---|---|---|---|---|---|
| | | | | Just after Exposure | After 2 Hours Lapse | After Forced Time Lapse Test |
| Example 27 | B-1 | 1 | 3 | 5 | 4.5 | 4.5 |
| Example 28 | B-2 | 2 | 3 | 5 | 4.5 | 4.5 |
| Example 29 | B-3 | 3 | 3 | 7 | 6.5 | 6.5 |
| Example 30 | B-4 | 4 | 3 | 6.5 | 6 | 6 |
| Example 31 | B-5 | 13 | 3 | 5.5 | 5 | 5 |
| Example 32 | B-6 | 15 | 3 | 7 | 6.5 | 6.5 |
| Example 33 | B-7 | 16 | 3 | 7 | 6.5 | 6.5 |
| Example 34 | B-8 | 35 | 3 | 7.5 | 7 | 7 |
| Example 35 | B-9 | 36 | 3 | 7.5 | 7 | 7 |
| Example 36 | B-10 | 47 | 3 | 7 | 6.5 | 6.5 |
| Example 37 | B-11 | 48 | 3 | 9 | 8.5 | 8.5 |
| Example 38 | B-12 | 59 | 3 | 7 | 6.5 | 6.5 |
| Example 39 | B-13 | 60 | 3 | 10 | 9.5 | 9.5 |
| Example 40 | B-14 | 79 | 3 | 7 | 6.5 | 6.5 |
| Example 41 | B-15 | 80 | 3 | 10 | 9.5 | 9.5 |
| Example 42 | B-16 | 90 | 3 | 11 | 10.5 | 10.5 |
| Example 43 | B-17 | 91 | 3 | 11.5 | 11 | 11 |
| Example 44 | B-18 | 92 | 3 | 10.5 | 10 | 10 |
| Example 45 | B-19 | 103 | 1 | 12 | 11.5 | 11.5 |
| Example 46 | B-20 | 103 | 2 | 12.5 | 12 | 12 |
| Example 47 | B-21 | 103 | 3 | 13 | 12.5 | 12.5 |
| Example 48 | B-22 | 104 | 3 | 11 | 10.5 | 10.5 |
| Example 49 | B-23 | 107 | 3 | 12 | 11.5 | 11.5 |
| Example 50 | B-24 | 108 | 3 | 11 | 10.5 | 10.5 |
| Example 51 | B-25 | 123 | 3 | 12 | 11.5 | 11.5 |
| Example 52 | B-26 | 124 | 3 | 11 | 10.5 | 10.5 |
| Comparative Example 4 | B'-1 | | 3 | 0.5 | 0 | 0 |
| Comparative Example 5 | B'-2 | Comparative Compound (1) | 3 | 0.5 | 0 | 0 |
| Comparative Example 6 | B'-3 | Comparative Compound (2) | — | 4.5 | 4 | 4 |

From the results shown in Table 8, it can be seen that the long wavelength responding color-forming composition film according to the invention exhibits the good color-forming property.

IV. Infrared Color-Forming Composition Film

IV-1. Production of Color-Forming Composition Films C-1, C-2 and C-5

Color-forming composition solution (5) shown below was prepared, coated on a polyester film having a thickness of 0.18 mm using a bar so as to have a dry coating amount of 1.0 g/m² and dried in an oven at 100° C. for 60 seconds to produce Color-forming composition films C-1, C-2 and C-5 (for Examples 53, 54 and 57), respectively.

<Color-Forming Composition Solution (5)>

| | |
|---|---|
| Binder polymer (1) shown above | 0.240 g |
| Infrared absorbing agent (1) having structure shown below | 0.020 g |
| Specific compound according to invention (compound shown in Table 9) | 0.030 g |
| Radical generator (compound shown in Table 9) | 0.162 g |
| Fluorine-based surfactant (1) shown above | 0.008 g |
| Trinormalbutylamine | 0.052 g |
| 2-Butanone | 1.091 g |
| 1-Methoxy-2-propanol | 8.609 g |

The structures of Infrared Absorbing agent (1) and Radical generator (4) are shown below.

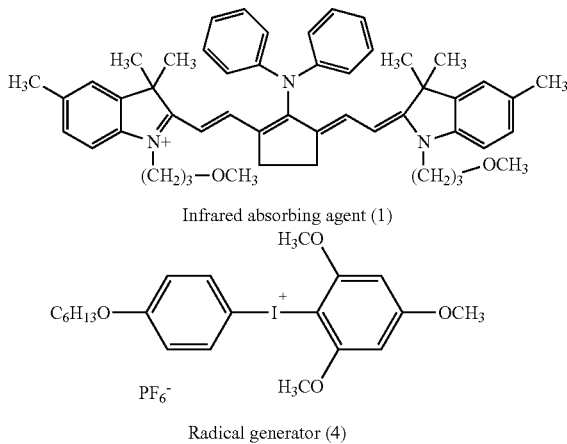

Infrared absorbing agent (1)

Radical generator (4)

IV-2. Production of Color-Forming Composition Films C-3, C-4 and C-6 to C-25

Color-forming composition films C-3, C-4 and C-6 to C-25 (for Examples 55, 56 and 58 to 77) were produced in the same manner as above except for using a color-forming composition solution in which the trinormalbutylamine in Color-forming composition solution (5) was not added, respectively.

IV-3. Production of Color-Forming Composition Film C'-1

Color-forming composition film C'-1 (for Comparative Example 7) was produced in the same manner as above except for not adding the specific compound according to the invention in Color-forming composition film C-3.

IV-4. Production of Color-Forming Composition Film C'-2

Color-forming composition film C'-2 (for Comparative Example 8) was produced in the same manner as above except for not adding the radical generator in Color-forming composition film C-3.

IV-5. Production of Color-Forming Composition Film C'-3

Color-forming composition film C'-3 (for Comparative Example 9) was produced in the same manner as above except for using Comparative compound (1) in place of the specific compound according to the invention in Color-forming composition film C-3.

IV-6. Production of Color-Forming Composition Film C'-4

Color-forming composition solution (6) shown below was prepared, coated on a polyester film having a thickness of 0.18 mm using a bar so as to have a dry coating amount of 1.0 g/m² and dried in an oven at 100° C. for 60 seconds to produce Color-forming composition film C'-4 (for Comparative Example 10).

<Color-Forming Composition Solution (6)>

| | |
|---|---|
| Binder polymer (1) shown above | 0.636 g |
| Comparative compound (2) shown above | 0.030 g |
| Infrared absorbing agent (1) shown above | 0.020 g |
| Fluorine-based surfactant (1) shown above | 0.008 g |
| 2-Butanone | 1.091 g |
| 1-Methoxy-2-propanol | 8.609 g |

IV-7. Evaluation of Color-Forming Property of Infrared Color-Forming Composition Film The infrared color-forming composition film produced was exposed by TRENDSETTER 3244VX (produced by Creo Co.) equipped with a water-cooled 40 W infrared semiconductor laser under the conditions of output of 11.7 W, a rotational number of an external drum of 250 rpm and resolution of 2,400 dpi. The evaluation of color formation of infrared color-forming composition film was conducted by measuring the color formation just after the exposure and at 2 hours lapse after the exposure kept in a dark place under room temperature condition. Also, the color-forming composition film was subjected to a forced time lapse test under conditions of 60° C. and 70% RH for 3 days and the color formation thereof just after the exposure was measured.

The color formation was measured in the same manner as in the color-forming composition film described above. As the value of ΔL is larger, it is meant that the color-forming property is more excellent. The results are shown in Table 9.

TABLE 9

| | Infrared Color-forming Composition Fim | Specific Compound | Radical Generator | Color-forming Property (ΔL) | | |
|---|---|---|---|---|---|---|
| | | | | Just after Exposure | After 2 Hours Lapse | After Forced Time Lapse Test |
| Example 53 | C-1 | 1 | 3 | 6.5 | 5.5 | 5.5 |
| Example 54 | C-2 | 2 | 3 | 6.5 | 5.5 | 5.5 |
| Example 55 | C-3 | 3 | 3 | 8.5 | 7.5 | 7.5 |
| Example 56 | C-4 | 4 | 3 | 8 | 7 | 7 |
| Example 57 | C-5 | 13 | 3 | 7 | 6 | 6 |

TABLE 9-continued

| | Infrared Color-forming Composition Fim | Specific Compound | Radical Generator | Color-forming Property (ΔL) | | |
|---|---|---|---|---|---|---|
| | | | | Just after Exposure | After 2 Hours Lapse | After Forced Time Lapse Test |
| Example 58 | C-6 | 15 | 3 | 8.5 | 7.5 | 7.5 |
| Example 59 | C-7 | 16 | 3 | 8.5 | 7.5 | 7.5 |
| Example 60 | C-8 | 35 | 3 | 9 | 8 | 8 |
| Example 61 | C-9 | 36 | 3 | 9 | 8 | 8 |
| Example 62 | C-10 | 47 | 3 | 8.5 | 7.5 | 7.5 |
| Example 63 | C-11 | 48 | 3 | 10.5 | 9.5 | 9.5 |
| Example 64 | C-12 | 59 | 3 | 8.5 | 7.5 | 7.5 |
| Example 65 | C-13 | 60 | 3 | 11.5 | 10.5 | 10.5 |
| Example 66 | C-14 | 79 | 3 | 8.5 | 7.5 | 7.5 |
| Example 67 | C-15 | 80 | 3 | 11.5 | 10.5 | 10.5 |
| Example 68 | C-16 | 90 | 3 | 12.5 | 11.5 | 11.5 |
| Example 69 | C-17 | 91 | 3 | 13 | 12 | 12 |
| Example 70 | C-18 | 92 | 3 | 12 | 11 | 11 |
| Example 71 | C-19 | 103 | 3 | 14.5 | 13.5 | 13.5 |
| Example 72 | C-20 | 103 | 4 | 14.0 | 13.0 | 13.0 |
| Example 73 | C-21 | 104 | 3 | 14.5 | 13.5 | 13.5 |
| Example 74 | C-22 | 107 | 3 | 13.5 | 12.5 | 12.5 |
| Example 75 | C-23 | 108 | 3 | 12.5 | 11.5 | 11.5 |
| Example 76 | C-24 | 123 | 3 | 13.5 | 12.5 | 12.5 |
| Example 77 | C-25 | 124 | 3 | 12.5 | 11.5 | 11.5 |
| Comparative Example 7 | C'-1 | — | 3 | 4.0 | 2.0 | 2.0 |
| Comparative Example 8 | C'-2 | 3 | — | 0.5 | 0.5 | 0.5 |
| Comparative Example 9 | C'-3 | Comparative Compound (1) | 3 | 4.0 | 2.0 | 2.0 |
| Comparative Example 10 | C'-4 | Comparative Compound (2) | — | 3.5 | 3.0 | 3.0 |

From the results shown in Table 9, it is apparent that the infrared color-forming composition film according to the invention exhibits the good color-forming property and the high color formation is maintained even with the laps of time after the color formation by exposure. Further, the preservation stability is good and the color-forming composition film after coating exhibits the high color formation even when it is exposed after the forced time lapse test.

V Infrared Color-Forming Curable Composition

V-1. Production of Infrared Color-Forming Curable Composition Films D-1, D-2 and D-5

Infrared color-forming curable composition solution (1) shown below was prepared, coated on a polyester film having a thickness of 0.18 mm using a bar so as to have a dry coating amount of 1.0 g/m² and dried in an oven at 100° C. for 60 seconds to produce Infrared color-forming curable composition films D-1, D-2 and D-5 (for Examples 78, 79 and 82), respectively.

<Infrared Color-Forming Curable Composition Solution (1)>

| | |
|---|---|
| Binder polymer (1) shown above | 0.240 g |
| Infrared absorbing agent (1) shown above | 0.020 g |
| Specific compound according; to invention (compound shown in Table 10) | 0.030 g |
| Radical generator (compound shown in Table 10) | 0.162 g |
| Trinormalbutylamine | 0.052 g |
| Polymerizable compound | 0.192 g |
| Tris(acryloyloxyethyl) isocyanurate (NK ESTER A-9300, produced by Shin-Nakamura Chemical Co., Ltd.) | |
| Fluorine-based surfactant (1) shown above | 0.008 g |
| 2-Butanone | 1.091 g |
| 1-Methoxy-2-propanol | 8.609 g |

V-2. Production of Infrared Color-Forming Curable Composition Films D-3, D-4 and D-6 to C-26

Infrared color-forming curable composition films D-3, D-4 and D-6 to C-26 (for Examples 80, 81 and 83 to 102) were produced in the same manner as above except for using an infrared color-forming curable composition solution in which the trinormalbutylamine in Infrared color-forming curable composition solution (1) was not added, respectively.

V-3. Production of Infrared Color-Forming Curable Composition Film D'-1

Infrared color-forming curable composition film D'-1 (for Comparative Example 11) was produced in the same manner as above except for not adding the specific compound according to the invention in Infrared color-forming curable composition film D-3.

V-4. Production of Infrared Color-Forming Curable Composition Film D'-2

Infrared color-forming curable composition film D'-2 (for Comparative Example 12) was produced in the same manner as above except for using Comparative compound (1) in place of the specific compound according to the invention in Infrared color-forming curable composition film D-3.

V-5. Production of Color-Forming Composition Film D'-3

Infrared color-forming curable composition film D'-3 (for Comparative Example 13) was produced in the same manner as above except for using Comparative compound (2) in place of the specific compound according to the invention in Infrared color-forming curable composition film D-3.

V-6. Evaluation of Color-Forming Property of Infrared Color-Forming Curable Composition Film The infrared color-forming curable composition film produced was exposed by TRENDSETTER 3244VX (produced by Creo Co.) equipped with a water-cooled 40 W infrared semiconductor laser under the conditions of output of 11.7

W, a rotational number of an external drum of 250 rpm and resolution of 2,400 dpi. The evaluation of color formation of infrared color-forming curable composition film was conducted by measuring the color formation just after the exposure and at 2 hours lapse after the exposure kept in a dark place under room temperature condition. Also, the color-forming curable composition film was subjected to a forced time lapse test under conditions of 60° C. and 70% RH for 3 days and the color formation just after the exposure was measured. The color formation was measured in the same manner as in the color-forming composition film described above. As the value of ΔL is larger, it is meant that the color-forming property is more excellent. The results are shown in Table 10.

V-7. Evaluation of Sensitivity of Infrared Color-Forming Curable Composition Film The infrared color-forming curable composition film produced was exposed by TRENDSETTER 3244VX (produced by Creo Co.) equipped with a water-cooled 40 W infrared semiconductor laser under the conditions of a rotational number of an external drum of 250 rpm and resolution of 2,400 dpi while varying the output value. The minimum exposure amount capable of forming a tack-free curd layer was determined in a unit of mJ/cm$^2$ and the reciprocal thereof was used as an index of the sensitivity. As to the evaluation result, the sensitivity of Infrared color-forming curable composition film (D'-1) obtained in Comparative Example 11 was taken as 100 and the sensitivities of other infrared color-forming curable composition films were relatively evaluated. As the value is larger, it is meant that the sensitivity is more excellent. The results are shown in Table 10.

From the results shown in Table 10, it is apparent that the infrared color-forming curable composition film according to the invention exhibits the good color-forming property without decrease in the sensitivity and the high color formation is maintained even with the laps of time after the color formation by exposure. Further, the preservation stability is good and the color-forming curable composition film after coating exhibits the high color formation even when it is exposed after the forced time lapse test.

VI. Lithographic Printing Plate Precursor of on-Press Development Type

VI-1. Production of Lithographic Printing Plate Precursors E-1, E-2 and E-5

[Production of Support]

An aluminum plate (material: JIS A 1050) having a thickness of 0.3 mm was subjected to a degreasing treatment at 50° C. for 30 seconds using a 10% by weight aqueous sodium aluminate solution in order to remove rolling oil on the surface thereof and then grained the surface thereof using three nylon brushes embedded with bundles of nylon bristle having a diameter of 0.3 mm and an aqueous suspension (specific gravity: 1.1 g/cm$^3$) of pumice having a median size of 25 μm, followed by thorough washing with water. The plate was subjected to etching by immersing in 25% by weight aqueous sodium hydroxide of 45° C. for 9 seconds, washed with water, then immersed in a 20% by weight nitric acid solution at 60° C. for 20 seconds, and washed with water. The etching amount of the grained surface was about 3 g/m$^2$.

Then, using an alternating current of 60 Hz, an electrochemical roughening treatment was continuously carried out on the plate. The electrolytic solution used was a 1% by

TABLE 10

| | Infrared Color-forming Curable Composition | Specific Compound | Radical Generator | Color-forming Property (ΔL) | | | Sensitivity |
| --- | --- | --- | --- | --- | --- | --- | --- |
| | | | | Just after Exposure | After 2 Hours Lapse | After Forced Time Lapse Test | |
| Example 78 | D-1 | 1 | 3 | 6.5 | 5.5 | 5.5 | 100 |
| Example 79 | D-2 | 2 | 3 | 6.5 | 5.5 | 5.5 | 100 |
| Example 80 | D-3 | 3 | 3 | 8.5 | 7.5 | 7.5 | 100 |
| Example 81 | D-4 | 4 | 3 | 8 | 7 | 7 | 100 |
| Example 82 | D-5 | 13 | 3 | 7 | 6 | 6 | 100 |
| Example 83 | D-6 | 15 | 3 | 8.5 | 7.5 | 7.5 | 100 |
| Example 84 | D-7 | 16 | 3 | 8.5 | 7.5 | 7.5 | 100 |
| Example 85 | D-8 | 35 | 3 | 9 | 8 | 8 | 100 |
| Example 86 | D-9 | 36 | 3 | 9 | 8 | 8 | 100 |
| Example 87 | D-10 | 47 | 3 | 8.5 | 7.5 | 7.5 | 100 |
| Example 88 | D-11 | 48 | 3 | 10.5 | 9.5 | 9.5 | 100 |
| Example 89 | D-12 | 59 | 3 | 8.5 | 7.5 | 7.5 | 100 |
| Example 90 | D-13 | 60 | 3 | 11.5 | 10.5 | 10.5 | 100 |
| Example 91 | D-14 | 79 | 3 | 8.5 | 7.5 | 7.5 | 100 |
| Example 92 | D-15 | 80 | 3 | 11.5 | 10.5 | 10.5 | 100 |
| Example 93 | D-16 | 90 | 3 | 12.5 | 11.5 | 11.5 | 100 |
| Example 94 | D-17 | 91 | 3 | 13 | 12 | 12 | 100 |
| Example 95 | D-18 | 92 | 3 | 12 | 11 | 11 | 100 |
| Example 96 | D-19 | 103 | 3 | 14.5 | 13.5 | 13.5 | 100 |
| Example 97 | D-20 | 103 | 4 | 14.0 | 13.0 | 13.0 | 100 |
| Example 98 | D-21 | 104 | 3 | 14.5 | 13.5 | 13.5 | 100 |
| Example 99 | D-22 | 107 | 3 | 13.5 | 12.5 | 12.5 | 100 |
| Example 100 | D-23 | 108 | 3 | 12.5 | 11.5 | 11.5 | 100 |
| Example 101 | D-24 | 123 | 3 | 13.5 | 12.5 | 12.5 | 100 |
| Example 102 | D-25 | 124 | 3 | 12.5 | 11.5 | 11.5 | 100 |
| Comparative Example 11 | D'-1 | — | 3 | 4.0 | 2.0 | 2.0 | 100 |
| Comparative Example 12 | D'-2 | Comparative Compound (1) | 3 | 4.0 | 2.0 | 2.0 | 100 |
| Comparative Example 13 | D'-3 | Comparative Compound (2) | 3 | 3.5 | 3.0 | 3.0 | 90 | weight aqueous nitric acid solution (containing 0.5% by weight of aluminum ion) and the temperature of electrolytic solution was 50° C. The electrochemical roughening treatment was conducted using a rectangular alternating current having a trapezoidal waveform such that the time TP necessary for the current value to reach the peak from zero was 0.8 msec and the duty ratio was 1:1, and using a carbon electrode as a counter electrode. A ferrite was used as an auxiliary anode. The current density was 30 A/dm² in terms of the peak value of the electric current, and 5% of the electric current flowing from the electric source was divided to the auxiliary anode. The quantity of electricity in the nitric acid electrolysis was 175 C/dm² in terms of the quantity of electricity when the aluminum plate functioned as an anode. The plate was then washed with water by spraying.

The plate was further subjected to an electrochemical roughening treatment in the same manner as in the nitric acid electrolysis above using as an electrolytic solution, a 0.5% by weight aqueous hydrochloric acid solution (containing 0.5% by weight of aluminum ion) having temperature of 50° C. and under the condition that the quantity of electricity was 50 C/dm² in terms of the quantity of electricity when the aluminum plate functioned as an anode. The plate was then washed with water by spraying.

The plate was then subjected to an anodizing treatment using as an electrolytic solution, 15% by weight sulfuric acid (containing 0.5% by weight of aluminum ion) at a current density of 15 A/dm² to form a direct current anodized film of 2.5 g/m², washed with water and dried to produce Support A.

Thereafter, in order to ensure the hydrophilicity of the non-image area, Support A was subjected to silicate treatment using a 2.5% by weight aqueous sodium silicate No. 3 solution at 60° C. for 10 seconds and then was washed with water to obtain Support B. The adhesion amount of Si was 10 mg/m². The center line average roughness (Ra) of the support was measured using a stylus having a diameter of 2 μm and found to be 0.51 μm.

[Formation of Undercoat Layer]

Coating solution for undercoat layer shown below was coated on Support B described above so as to have a dry coating amount of 20 mg/m² to produce a support having an undercoat layer shown below.

<Coating Solution for Undercoat Layer>

| Compound (1) for undercoat layer having structure shown below | 0.18 g |
|---|---|
| Hydroxyethyliminodiacetic acid | 0.10 g |
| Methanol | 55.24 g |
| Water | 6.15 g |

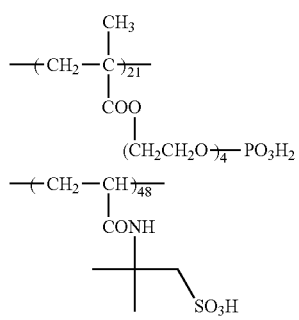

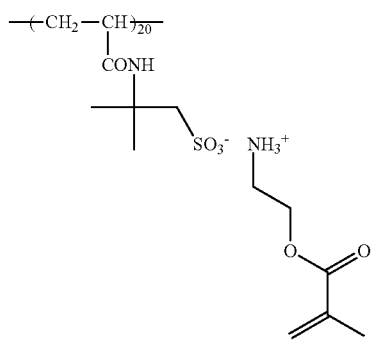

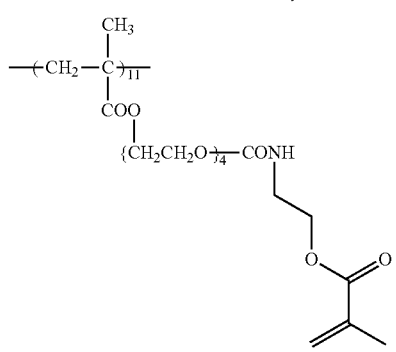

(Mw: 100,000)

Compound (1) for undercoat layer

[Formation of Image-Recording Layer]

Coating solution (1) for image-recording layer having the composition shown below was coated on the undercoat layer formed as described above by a bar and dried in an oven at 100° C. for 60 seconds to form an image-recording layer having a dry coating amount of 1.0 g/m².

Coating solution (1) for image-recording layer was prepared by mixing the photosensitive solution shown below with the microgel solution shown below just before the coating, followed by stirring.

<Photosensitive Solution>

| Binder polymer (1) shown above | 0.240 g |
|---|---|
| Infrared absorbing agent (1) shown above | 0.030 g |
| Specific compound according to invention (compound shown in Table 11) | 0.030 g |
| Radical generator (compound shown in Table 11) | 0.162 g |
| Trinormalbutylamine | 0.052 g |
| Polymerizable compound Tris(acryloyloxyethyl) isocyanurate (NK ESTER A-9300, produced by Shin-Nakamura Chemical Co., Ltd.) | 0.192 g |
| Hydrophilic low molecular weight compound Tris(2-hydroxyethyl) isocyanurate | 0.062 g |
| Hydrophilic low molecular weight compound (1) having structure shown below | 0.050 g |
| Oil-sensitizing agent (Phosphonium compound (1) having structure shown below) | 0.055 g |
| Oil-sensitizing agent Benzyl dimethyl octyl ammonium PF₆ salt | 0.018 g |
| Oil-sensitizing agent (Ammonium group-containing polymer having structure shown below (reduced specific viscosity: 44 ml/g) | 0.035 g |
| Fluorine-based surfactant (1) shown above | 0.008 g |
| 2-Butanone | 1.091 g |
| 1-Methoxy-2-propanol | 8.609 g |

79

<Microgel Solution>

| Microgel | 2.640 g |
|---|---|
| Distilled water | 2.425 g |

The structures of Hydrophilic low molecular weight compound (1), Phosphonium compound (1) and Ammonium group-containing polymer, and the synthesis method of microgel are shown below.

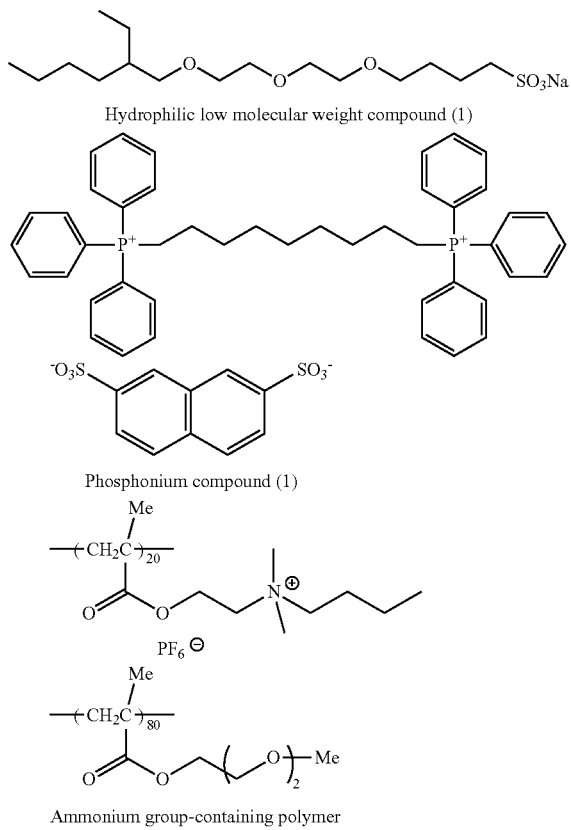

Hydrophilic low molecular weight compound (1)

Phosphonium compound (1)

Ammonium group-containing polymer

<Synthesis of Microgel>

An oil phase component was prepared by dissolving 10 g of adduct of trimethylolpropane and xylene diisocyanate (TAKENATE D-110N, produced by Mitsui Chemicals Inc.), 3.15 g of pentaerythritol triacrylate (SR444, produced by Nippon Kayaku Co., Ltd.) and 0.1 g of an alkylbenzenesulfonate (PIONIN A-41C, produced by Takemoto Oil & Fat Co., Ltd.) in 17 g of ethyl acetate. As an aqueous phase component, 40 g of an aqueous 4% by weight solution of polyvinyl alcohol (PVA-205, produced by Kuraray Co., Ltd) was prepared. The oil phase component and the aqueous phase component were mixed and the mixture was emulsified using a homogenizer at 12,000 rpm for 10 minutes. The resulting emulsion was added to 25 g of distilled water and stirred at room temperature for 30 minutes and then at 50° C. for 3 hours. The microgel liquid thus-obtained was diluted using distilled water so as to have the solid content concentration of 15% by weight to prepare the microgel. The average particle size of the microgel was measured by a light scattering method and found to be 0.2 μm.

[Formation of Protective Layer]

Coating solution for protective layer having the composition shown below was further coated on the image-recording layer described above by a bar and dried in an oven at 120° C. for 60 seconds to form a protective layer having a dry coating amount of 0.15 g/m², thereby producing Lithographic printing plate precursors E-1, E-2 and E-5 (for Examples 103, 104 and 107), respectively.

<Coating Solution for Protective Layer>

| Dispersion of inorganic stratiform compound (1) | 1.5 g |
|---|---|
| Aqueous 6% by weight solution of polyvinyl alcohol (CKS 50, sulfonic acid-modified, saponification degree: 99% by mole or more, polymerization degree: 300, produced by Nippon Synthetic Chemical Industry Co., Ltd.) | 0.55 g |
| Aqueous 6% by weight solution of polyvinyl alcohol (PVA-405, saponification degree: 81.5% by mole, polymerization degree: 500, produced by Kuraray Co., Ltd.) | 0.03 g |
| Aqueous 1% by weight solution of surfactant (EMALEX 710, produced by Nihon Emulsion Co., Ltd.) | 0.86 g |
| Ion-exchanged water | 6.0 g |

<Preparation of Dispersion of Inorganic Stratiform Compound (1)>

To 193.6 g of ion-exchanged water was added 6.4 g of synthetic mica (SOMASIF ME-100, produced by CO-OP Chemical Co., Ltd.) and the mixture was dispersed using a homogenizer until an average particle size (according to a laser scattering method) became 3 μm. The aspect ratio of the inorganic particle thus-dispersed was 100 or more.

VI-2. Production of Lithographic Printing Plate Precursors E-3, E-4 and E-6 to E-25

Lithographic printing plate precursors E-3, E-4 and E-6 to E-25 (for Examples 105, 106 and 108 to 127) were produced in the same manner as above except for using a coating solution for image recording layer in which the trinormalbutylamine in Coating solution (1) for image-recording layer was not added, respectively.

VI-3. Production of Lithographic printing plate precursor E-26 (for Example 128)

Coating solution (2) for image-recording layer shown below was coated on the support having the undercoat layer same as in Lithographic printing plate precursor E-1 by a bar and dried in an oven at 82° C. for 90 seconds to form an image-recording layer having a dry coating amount of 1.2 g/m² to produce Lithographic printing plate precursor E-26 (for Example 128).

<Coating Solution (2) for Image-Recording Layer>

| Aqueous dispersion (1) of polymer fine particle (by synthesis method shown below) | 20.0 g |
|---|---|
| Infrared absorbing agent (2) (compound shown below) | 0.020 g |
| Specific compound according to invention (compound shown in Table 11) | 0.030 g |
| Radical generator (5) IRGACURE 250 | 0.30 g |
| Monomer having ethylenically unsaturated group SR-399 (produced by Sartomer Co., Inc.) | 1.50 g |
| Mercapto-3-triazole | 0.2 g |
| Binder polymer | 0.4 g |
| BYK 336 (produced by BYK-Chimie GmbH) | |
| KLUCEL M (produced by Hercules Chemical Co., Inc.) | 4.8 g |
| ELVACITE 4026 (produced by Ineos Acrylica Inc.) | 2.5 g |
| n-Propanol | 55.0 g |
| 2-Butanone | 17.0 g |

The compounds indicated using their trade names in the composition described above are shown below.

IRGACURE 250: (4-Methoxyphenyl)[4-(2-methylpropyl)phenyl]iodonium hexafluorophosphate (75% by weight propylene carbonate solution)

SR-399: Dipentaerythritol pentaacrylate

BYK 336: Modified dimethylpolysiloxane copolymer (25% by weight xylene/methoxypropyl acetate solution)
KLUCEL M: Hydroxypropyl cellulose (2% by weight aqueous solution)
ELVACITE 4026: Highly branched polymethyl methacrylate (10% by weight 2-butanone solution)

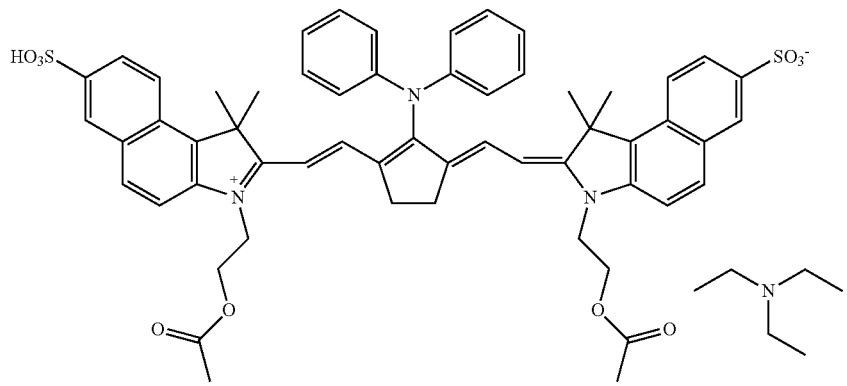

Infrared absorbing agent (2)

<Synthesis of Aqueous Dispersion (1) of Polymer Fine Particle>

A stirrer, a thermometer, a dropping funnel, a nitrogen inlet tube and a reflux condenser were attached to a 1,000 ml four-neck flask and while carrying out deoxygenation by introduction of nitrogen gas, 10 g of polyethylene glycol methyl ether methacrylate (PEGMA, average repeating unit number of ethylene glycol: 50), 200 g of distilled water and 200 g of n-propanol were charged therein and heated until the internal temperature reached 70° C.

Then, a mixture of 10 g of styrene (St), 80 g of acrylonitrile (AN) and 0.8 g of 2,2'-azobisisobutyronitrile previously mixed was dropwise added to the flask over a period of one hour. After the completion of the dropwise addition, the mixture was continued to react as it was for 5 hours. Then, 0.4 g of 2,2'-azobisisobutyronitrile was added and the internal temperature was raised to 80° C. Thereafter, 0.5 g of 2,2'-azobisisobutyronitrile was added over a period of 6 hours. At the stage after reacting for 20 hours in total, the polymerization proceeded 98% or more to obtain Aqueous dispersion (1) of polymer fine particle of PEGMA/St/AN (10/10/80 in a weight ratio). The particle size distribution of the polymer fine particle had the maximum value at the particle size of 150 nm.

The particle size distribution was determined by taking an electron microphotograph of the polymer fine particle, measuring particle sizes of 5,000 fine particles in total on the photograph, and dividing a range from the largest value of the particle size measured to 0 on a logarithmic scale into 50 parts to obtain occurrence frequency of each particle size by plotting. With respect to the aspherical particle, a particle size of a spherical particle having a particle area equivalent to the particle area of the aspherical particle on the photograph was defined as the particle size.

VI-4. Production of Lithographic Printing Plate Precursor E'-1

Lithographic printing plate precursors E'-1 (for Comparative Example 14) was produced in the same manner as above except for not adding the specific compound according to the invention in Lithographic printing plate precursor E-3.

VI-5. Production of Lithographic Printing Plate Precursor E'-2

Lithographic printing plate precursors E'-2 (for Comparative Example 15) was produced in the same manner as above except for using Comparative compound (1) in place of the specific compound according to the invention in Lithographic printing plate precursor E-3.

VI-6. Production of Lithographic Printing Plate Precursor E'-3

Lithographic printing plate precursors E'-3 (for Comparative Example 16) was produced in the same manner as above except for using Comparative compound (2) in place of the specific compound according to the invention in Lithographic printing plate precursor E-3.

VI-7. Evaluation of Lithographic Printing Plate Precursor
(i) Color-Forming Property The lithographic printing plate precursor obtained was exposed by TRENDSETTER 3244VX (produced by Creo Co.) equipped with a water-cooled 40 W infrared semiconductor laser under the conditions of output of 11.7 W, a rotational number of an external drum of 250 rpm and resolution of 2,400 dpi.

The color formation were measured just after the exposure and at 2 hours lapse after the exposure kept in a dark place under room temperature condition. Also, the lithographic printing plate precursor was subjected to a forced time lapse test under conditions of 60° C. and 70% RH for 3 days and the color formation thereof just after the exposure was measured.

The color formation was measured in the same manner as in the color-forming composition film described above. As the value of ΔL is larger, it is meant that the color-forming property is more excellent. The results are shown in Table 11.

(ii) On-Press Development Property

The lithographic printing plate precursor obtained was exposed by LUXEL PLATESETTER T-6000III equipped with an infrared semiconductor laser (produced by Fujifilm Corp.) under the conditions of a rotational number of an external drum of 1,000 rpm, laser output of 70% and resolution of 2,400 dpi. The exposed image contained a solid image and a 50% halftone dot chart of a 20 μm-dot FM screen.

The exposed lithographic printing plate precursor was mounted without undergoing development processing on a plate cylinder of a printing machine (LITHRONE 26, produced by Komori Corp.). Using dampening water (ECOLITY-2 (produced by Fujifilm Corp.)/tap water=2/98 (by volume ratio)) and SPACE COLOR FUSION-G (N) Black Ink (produced by DIC Graphics Corp.), the dampening water and ink were supplied according to the standard automatic printing start method of LITHRONE 26 to conduct on-press development and then printing on 100 sheets of TOKUBISHI art paper (76.5 kg) at a printing speed of 10,000 sheets per hour.

A number of the printing papers required until the on-press development of the unexposed area of the image-recording layer on the printing machine was completed to reach a state where the ink was not transferred to the printing paper in the non-image area was measured to evaluate the on-press development property. The results are shown in Table 11.

(iii) Printing Durability

After performing the evaluation for the on-press development property described above, the printing was continued. As the increase in a number of printing papers, the image-recording layer was gradually abraded to cause decrease in the ink density on a printed material. A number of printed materials wherein a value obtained by measuring a halftone dot area rate of the 50% halftone dot of FM screen on the printed material using a Gretag densitometer decreased by 5% from the value measured on the 100th paper of the printing was regarded as a number of printed materials at the completion of printing to evaluate the printing durability. As to the evaluation result, the number of printed materials at the completion of printing of the lithographic printing plate precursor obtained in Comparative Example 14 was taken as 100 and the number of printed materials at the completion of printing of other lithographic printing plate precursors were relatively evaluated. As the value is larger, it is meant that the printing durability is more excellent. The results are shown in Table 11.

TABLE 11

| | Lithographic Printing Plate Precursor | Specific Compound | Radical Generator | Color-forming Property (ΔL) | | | On-press Development Property (sheets) | Printing Durability |
|---|---|---|---|---|---|---|---|---|
| | | | | Just after Exposure | After 2 Hours Lapse | After Forced Time Lapse Test | | |
| Example 103 | E-1 | 1 | 3 | 6.5 | 5.5 | 5.5 | 30 | 100 |
| Example 104 | E-2 | 2 | 3 | 6.5 | 5.5 | 5.5 | 30 | 100 |
| Example 105 | E-3 | 3 | 3 | 8.5 | 7.5 | 7.5 | 30 | 100 |
| Example 106 | E-4 | 4 | 3 | 8 | 7 | 7 | 30 | 100 |
| Example 107 | E-5 | 13 | 3 | 7 | 6 | 6 | 30 | 100 |
| Example 108 | E-6 | 15 | 3 | 8.5 | 7.5 | 7.5 | 30 | 100 |
| Example 109 | E-7 | 16 | 3 | 8.5 | 7.5 | 7.5 | 30 | 100 |
| Example 110 | E-8 | 35 | 3 | 9 | 8 | 8 | 30 | 100 |
| Example 111 | E-9 | 36 | 3 | 9 | 8 | 8 | 30 | 100 |
| Example 112 | E-10 | 47 | 3 | 8.5 | 7.5 | 7.5 | 30 | 100 |
| Example 113 | E-11 | 48 | 3 | 10.5 | 9.5 | 9.5 | 30 | 100 |
| Example 114 | E-12 | 59 | 3 | 8.5 | 7.5 | 7.5 | 30 | 100 |
| Example 115 | E-13 | 60 | 3 | 11.5 | 10.5 | 10.5 | 30 | 100 |
| Example 116 | E-14 | 79 | 3 | 8.5 | 7.5 | 7.5 | 30 | 100 |
| Example 117 | E-15 | 80 | 3 | 11.5 | 10.5 | 10.5 | 30 | 100 |
| Example 118 | E-16 | 90 | 3 | 12.5 | 11.5 | 11.5 | 30 | 100 |
| Example 119 | E-17 | 91 | 3 | 13 | 12 | 12 | 30 | 100 |
| Example 120 | E-18 | 92 | 3 | 12 | 11 | 11 | 30 | 100 |
| Example 121 | E-19 | 103 | 3 | 14.5 | 13.5 | 13.5 | 30 | 100 |
| Example 122 | E-20 | 103 | 4 | 14.0 | 13.0 | 13.0 | 30 | 100 |
| Example 123 | E-21 | 104 | 3 | 14.5 | 13.5 | 13.5 | 30 | 100 |
| Example 124 | E-22 | 107 | 3 | 13.5 | 12.5 | 12.5 | 30 | 100 |
| Example 125 | E-23 | 108 | 3 | 12.5 | 11.5 | 11.5 | 30 | 100 |
| Example 126 | E-24 | 123 | 3 | 13.5 | 12.5 | 12.5 | 30 | 100 |
| Example 127 | E-25 | 124 | 3 | 12.5 | 11.5 | 11.5 | 30 | 100 |
| Example 128 | E-26 | 103 | 5 | 12.5 | 11.5 | 11.5 | 30 | 100 |
| Comparative Example 14 | E'-1 | — | 3 | 4.0 | 2.0 | 2.0 | 30 | 100 |
| Comparative Example 15 | E'-2 | Comparative Compound (1) | 3 | 4.0 | 2.0 | 2.0 | 30 | 100 |
| Comparative Example 16 | E'-3 | Comparative Compound (2) | 3 | 3.5 | 3.0 | 3.0 | 30 | 90 |

From the results shown in Table 11, it is apparent that the lithographic printing plate precursor according to the invention exhibits the good color-forming property without decrease in the printing aptitude represented by the on-press development property and printing durability, and the high color formation is maintained even with the laps of time after the color formation by exposure. Further, the preservation stability is good and the lithographic printing plate precursor produced exhibits the high color formation even when it is exposed after the forced time lapse test.

INDUSTRIAL APPLICABILITY

According to the invention, a color-forming composition and a color-forming curable composition each of which forms high color upon exposure to light and has small fading after the color formation is obtained. Also, a lithographic printing plate precursor, particularly, a lithographic printing plate precursor capable of undergoing on-press development, which forms high color upon exposure to light, which has small fading after the color formation, which has a high plate inspection property, and which provides a lithographic printing plate of high printing durability by plate making, and a plate making method thereof are obtained. Further, a novel color-forming compound is provided.

Although the invention has been described in detail and by reference to specific embodiments, it is apparent to those skilled in the art that it is possible to add various alterations and modifications insofar as the alterations and modifications do not deviate from the spirit and the scope of the invention.

This application is based on a Japanese patent application filed on Feb. 23, 2012 (Japanese Patent Application No. 2012-037653), and the contents thereof are incorporated herein by reference.

The invention claimed is:

1. A color-forming composition containing (A) a radical generator, (B) a compound represented by the following formula (1) and (C) a binder polymer:

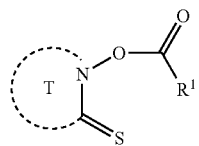

(1)

wherein, in the formula (1), $R^1$ represents a group which reacts with a radical generated from the radical generator (A) to be released and forms a dye after the release, and T represents a nitrogen-containing hetero ring.

2. The color-forming composition as claimed in claim 1, wherein $R^1$ in the compound represented by the formula (1) has a structure represented by the following formula (2) or (3):

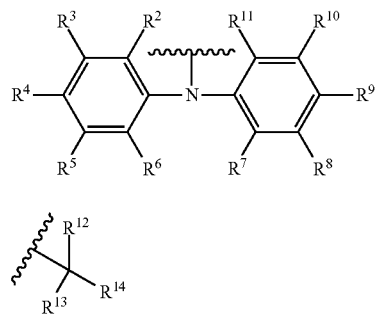

wherein, in the formulae (2) and (3), $R^2, R^3, R^5, R^6, R^7, R^8, R^{10}$ and $R^{11}$ each independently represents a hydrogen atom, an alkyl group, $OR^{15}$, $NR^{16}R^{17}$, $SR^{18}$ or a halogen atom, or $R^5$ and $R^6$, $R^7$ and $R^8$ or $R^6$ and $R^7$ may be connected with each other to form a condensed ring structure, $R^4$ and $R^9$ each independently represents any one of $OR^{15}$, $NR^{19}R^{20}$ and $SR^{18}$ each independently represents an alkyl group, $R^{16}$ and $R^{17}$ each independently represents a hydrogen atom or an alkyl group, or $R^{16}$ and $R^{17}$ may form a ring structure, $R^{19}$ and $R^{20}$ each independently represents a hydrogen atom, an alkyl group, an aryl group, an alkylcarbonyl group, an arylcarbonyl group, an aryloxycarbonyl group, an alkoxycarbonyl group, an aminocarbonyl group or an alkylsulfonyl group, or $R^{19}$ and $R^{20}$ may form a ring structure, and $R^{12}$, $R^{13}$ and $R^{14}$ each independently represents an aryl group.

3. The color-forming composition as claimed in claim 1, wherein a maximum absorption wavelength (λmax) of the dye which is formed by releasing from the compound represented by formula (1) is from 500 to 600 nm.

4. The color-forming composition as claimed in claim 1, wherein the compound represented by the formula (1) is a compound represented by the following formula (4) or (5):

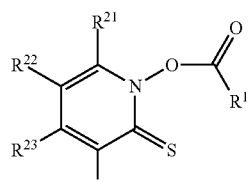

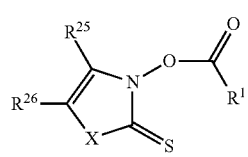

wherein, in the formulae (4) and (5), $R^{21}$, $R^{22}$, $R^{23}$, $R^{24}$, $R^{25}$ and $R^{26}$ each independently represents a hydrogen atom, an alkyl group, an aryl group, $OR^{15}$, $NR^{16}R^{17}$, $SR^{18}$ or a halogen atom, or $R^{21}$ and $R^{22}$, $R^{22}$ and $R^{23}$, $R^{23}$ and $R^{24}$ or $R^{25}$ and $R^{26}$ may be connected with each other to form a condensed ring structure, $R^{15}$ and $R^{18}$ each independently represents an alkyl group, $R^{16}$ and $R^{17}$ each independently represents a hydrogen atom or an alkyl group, or $R^{16}$ and $R^{17}$ may form a ring structure, X represents a dialkylmethylene group, O, $NR^{27}$ or S, $R^{27}$ represents a hydrogen atom, an alkyl group or an aryl group, and $R^1$ has the same meaning as $R^1$ defined in formula (1).

5. The color-forming composition as claimed in claim 1, which further contains (D) a sensitizing dye.

6. The color-forming composition as claimed in claim 5, wherein the sensitizing dye (D) is an infrared sensitizing dye.

7. The color-forming composition as claimed in claim 1, wherein the radical generator (A) is an iodonium salt or a sulfonium salt.

8. A color-forming curable composition, wherein the color-forming composition as claimed in claim 1 further contains (E) a polymerizable compound.

9. A lithographic printing plate precursor comprising an image-recording layer containing the color-forming curable composition as claimed in claim 8 on a support.

10. The lithographic printing plate precursor as claimed in claim 9, which further comprises a protective layer.

11. The lithographic printing plate precursor as claimed in claim 10, wherein the protective layer contains an inorganic stratiform compound.

12. The lithographic printing plate precursor as claimed in claim 9, wherein the image-recording layer contains a hydrophobizing precursor.

13. A plate making method comprising conducting on-press development processing by any one of a method comprising image-exposing the lithographic printing plate precursor as claimed in claim 9 to form color in an exposed area, mounting the image-exposed lithographic printing plate precursor on a printing machine and supplying printing ink and dampening water, and a method comprising mounting the lithographic printing plate precursor as claimed in claim 9 on a printing machine, image-exposing the lithographic printing plate precursor to form color in an exposed area and supplying printing ink and dampening water.

14. A compound represented by the following formula (4) or (5) shown below:

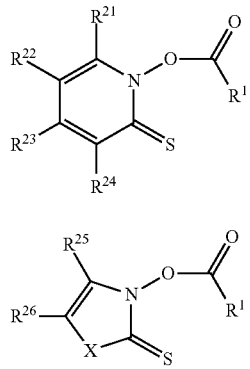

wherein, in the formulae (4) and (5), $R^1$ represents a structure represented by the following formula (2) or (3), $R^{21}$, $R^{22}$, $R^{23}$ and $R^{26}$ each independently represents a hydrogen atom, $R^{24}$ represents a hydrogen atom or a chlorine atom, $R^{25}$ represents a hydrogen atom or a phenyl group, X represents a dialkylmethylene group, O, $NR^{27}$ or S, and $R^{27}$ represents a hydrogen atom, an alkyl group or an aryl group;

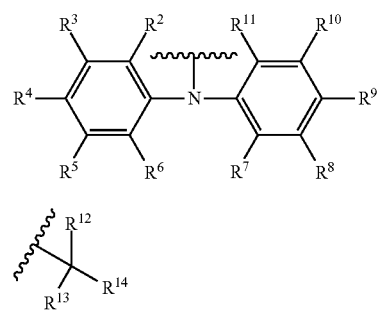

wherein, in the formulae (2) and (3), $R^2$, $R^3$, $R^5$, $R^6$, $R^7$, $R^8$, $R^{10}$ and $R^{11}$ each independently represents a hydrogen atom or an alkyl group, or $R^5$ and $R^6$, $R^7$ and $R^8$ or $R^6$ and $R^7$ may be connected with each other to form a condensed ring structure, $R^4$ and $R^9$ each independently represents $NR^{18}R^{19}$, $R^{18}$ and $R^{19}$ each independently represents a hydrogen atom, an alkyl group or an alkylsulfonyl group, and $R^{12}$, $R^{13}$ and $R^{14}$ each independently represents a phenyl group having a dialkylamino group in its 4-position.

15. The compound as claimed in claim 14, wherein $R^1$ in formula (4) represents a structure represented by the formula (2) or (3), and at least one of $R^2$, $R^3$, $R^5$, $R^6$, $R^7$, $R^8$, $R^{10}$ and $R^{11}$ is an alkyl group having from 1 to 20 carbon atoms.

16. The compound as claimed in claim 14, wherein $R^1$ in formula (4) represents a structure represented by the formula (3).

* * * * *